United States Patent
Aricha et al.

(10) Patent No.: US 12,233,092 B2
(45) Date of Patent: Feb. 25, 2025

(54) MSC-NTF SPECIFIC EXOSOMES AND USE THEREOF

(71) Applicant: BRAINSTORM CELL THERAPEUTICS LTD., Petach Tikva (IL)

(72) Inventors: Revital Aricha, Giv'at Shmuel (IL); Haggai Kaspi, Ganei Tikva (IL); Jonathan Semo, Giv'atayim (IL); Yael Gothelf, Kiryat Ono (IL)

(73) Assignee: BRAINSTORM CELL THERAPEUTICS LTD., Petach Tikva (IL)

( * ) Notice: Subject to any disclaimer, the term of this patent is extended or adjusted under 35 U.S.C. 154(b) by 0 days.

(21) Appl. No.: 16/981,757

(22) PCT Filed: Apr. 10, 2019

(86) PCT No.: PCT/IL2019/050401
§ 371 (c)(1),
(2) Date: Sep. 17, 2020

(87) PCT Pub. No.: WO2019/198077
PCT Pub. Date: Oct. 17, 2019

(65) Prior Publication Data
US 2021/0030807 A1  Feb. 4, 2021

Related U.S. Application Data

(60) Provisional application No. 62/665,558, filed on May 2, 2018, provisional application No. 62/655,249, filed on Apr. 10, 2018.

(51) Int. Cl.
| | |
|---|---|
| *A61K 35/28* | (2015.01) |
| *C07K 14/475* | (2006.01) |
| *C07K 14/49* | (2006.01) |
| *C07K 14/52* | (2006.01) |
| *C07K 14/54* | (2006.01) |
| *A61K 38/00* | (2006.01) |
| *A61P 25/16* | (2006.01) |

(52) U.S. Cl.
CPC ............ *A61K 35/28* (2013.01); *C07K 14/475* (2013.01); *C07K 14/49* (2013.01); *C07K 14/521* (2013.01); *C07K 14/5415* (2013.01); *C07K 14/5437* (2013.01); *A61K 38/00* (2013.01); *A61P 25/16* (2018.01)

(58) Field of Classification Search
None
See application file for complete search history.

(56) References Cited

U.S. PATENT DOCUMENTS

| | | | |
|---|---|---|---|
| 8,647,874 B2 | 2/2014 | Offen et al. | |
| 8,663,987 B2 | 3/2014 | Kadouri et al. | |
| 8,900,574 B2 | 12/2014 | Kadouri et al. | |
| 9,474,787 B2 | 10/2016 | Kadouri et al. | |
| 9,877,989 B2 | 1/2018 | Beelen et al. | |
| 10,564,149 B2 * | 2/2020 | Gothelf | A61K 35/28 |
| 10,624,929 B2 | 4/2020 | Mitsialis et al. | |
| 2017/0258843 A1 | 9/2017 | Ichim et al. | |
| 2017/0296588 A1 | 10/2017 | Ichim et al. | |
| 2018/0036348 A1 | 2/2018 | Riordan | |
| 2021/0283183 A1 | 9/2021 | Cho et al. | |

FOREIGN PATENT DOCUMENTS

| | | | | |
|---|---|---|---|---|
| EP | 1893747 B1 | 9/2014 | | |
| IL | 209604 A | 5/2015 | | |
| WO | WO-2009105044 A1 | 8/2009 | | |
| WO | WO-2014024183 A1 * | 2/2014 | ............ | A61K 35/28 |
| WO | WO-2014110094 A1 | 7/2014 | | |
| WO | WO-2015121859 A1 | 8/2015 | | |
| WO | WO-2016082882 A1 * | 6/2016 | ............ | A61K 35/12 |
| WO | WO-2016083500 A1 | 6/2016 | | |
| WO | WO-2017117585 A1 * | 7/2017 | ............ | A61K 35/28 |
| WO | WO-2018015945 A2 | 1/2018 | | |
| WO | WO 2018/062973 A1 | 4/2018 | | |

OTHER PUBLICATIONS

Phinney (Stem Cells 2017;35:851-858) (Year: 2017).*
Allodi, I., Comley. L., Nichterwitz, S., Nizzardo, M., Simone, C., Benitez, J. A., . . . & Hedlund, E. (2016). Differential neuronal vulnerability identifies IGF-2 as a protective factor in ALS. Scientific reports, 6, 25960.
Alvarez-Erviti, L., Seow, Y., Schapira, A. H., Gardiner, C., Sargent, I. L., Wood, M. J., & Cooper, J. M. (2011). Lysosomal dysfunction increases exosome-mediated alpha-synuclein release and transmission. Neurobiology of disease, 42(3), 360-367.
Alvarez-Erviti, L., Seow, Y., Yin, H., Betts, C., Lakhal, S., & Wood, M. J. (2011). Delivery of siRNA to the mouse brain by systemic injection of targeted exosomes. Nature biotechnology, 29(4), 341-345.
Berry, J. D., Cudkowicz, M. E., Windebank, A. J., Staff, N. P., Owegi, M., Nicholson, K., . . . & Mehra, M. (2019). NurOwn, phase 2, randomized, clinical trial in patients with ALS: Safety, clinical, and biomarker results. Neurology, 93(24), e2294-e2305.
Bonafede, R., Scambi, I., Peroni, D., Potrich, V., Boschi, F., Benati, D., . . . & Mariotti, R. (2016). Exosome derived from murine adipose-derived stromal cells: Neuroprotective effect on in vitro model of amyotrophic lateral sclerosis. Experimental cell research, 340(1), 150-158.

(Continued)

*Primary Examiner* — Brian Gangle
*Assistant Examiner* — Andrea K McCollum
(74) *Attorney, Agent, or Firm* — Mark S Cohen; PEARL COHEN ZEDEK LATZER BARATZ LLP

(57) ABSTRACT

Provided herein are highly-characterized isolated exosomes, methods to produce such exosomes, and methods for the use of such exosomes in treating diseases such as neurodegenerative diseases.

9 Claims, 11 Drawing Sheets

(56) References Cited

OTHER PUBLICATIONS

Braccioli, L., Van Velthoven, C., & Heijnen, C. J. (2014). Exosomes: a new weapon to treat the central nervous system. Molecular neurobiology, 49(1), 113-119.

Didiot, M. C., Hall, L. M., Coles, A. H., Haraszti, R. A., Godinho, B. M., Chase, K., . . . & Echeverria, D. (2016). Exosome-mediated delivery of hydrophobically modified siRNA for huntingtin mRNA silencing. Molecular Therapy, 24(10), 1836-1847.

Dominici, M. L. B. K., Le Blanc, K., Mueller, I., Slaper-Cortenbach, I., Marini, F. C., Krause, D. S., . . . & Horwitz, E. M. (2006). Minimal criteria for defining multipotent mesenchymal stromal cells. The International Society for Cellular Therapy position statement. Cytotherapy, 8(4), 315-317.

Eirin, A., Zhu, X. Y., Puranik, A. S., Woollard, J. R., Tang, H., Dasari, S., . . . & Lerman, L. O. (2016). Comparative proteomic analysis of extracellular vesicles isolated from porcine adipose tissue-derived mesenchymal stem/stromal cells. Scientific reports, 6, 36120.

El-Andaloussi, S., Lee, Y., Lakhal-Littleton, S., Li, J., Seow, Y., Gardiner, C., . . . & Wood, M. J. (2012). Exosome-mediated delivery of siRNA in vitro and in vivo. Nature protocols, 7(12), 2112.

Fischer, L. R., Culver, D. G., Tennant, P., Davis, A. A., Wang, M., Castellano-Sanchez, A., . . . & Glass, J. D. (2004). Amyotrophic lateral sclerosis is a distal axonopathy: evidence in mice and man. Experimental neurology, 185(2), 232-240.

Fontanilla, C. V., Gu, H., Liu, Q., Zhu, T. Z., Zhou, C., Johnstone, B. H., . . . & Du, Y. (2015). Adipose-derived stem cell conditioned media extends survival time of a mouse model of amyotrophic lateral sclerosis. Scientific reports, 5, 16953.

Frakes, A. E., Ferraiuolo, L., Haidet-Phillips, A. M., Schmelzer, L., Braun, L., Miranda, C. J., . . . & Popovich, P. G. (2014). Microglia Induce motor neuron death via the classical NF-κB pathway in amyotrophic lateral sclerosis. Neuron, 81(5), 1009-1023.

Frey, D., Laux, T., Xu, L., Schneider, C., & Caroni, P. (2000). Shared and unique roles of CAP23 and GAP43 in actin regulation, neurite outgrowth, and anatomical plasticity. The Journal of cell biology, 149(7), 1443-1454.

Gomzikova, M. O., & Rizvanov, A. A. (2017). Current trends in regenerative medicine: from cell to cell-free therapy. BioNanoScience, 7(1), 240-245.

Gothelf, Y., Abramov, N., Harel, A., & Offen, D. (2014). Safety of repeated transplantations of neurotrophic factors-secreting human mesenchymal stromal stem cells. Clinical and Translational Medicine, 3(1), 21.

Gothelf, Y., Kaspi, H., Abramov, N., & Aricha, R. (2017). miRNA profiling of NurOwn®: mesenchymal stem cells secreting neurotrophic factors. Stem Cell Research & Therapy, 8(1), 1-9.

Ha, D., Yang, N., & Nadithe, V. (2016). Exosomes as therapeutic drug carriers and delivery vehicles across biological membranes: current perspectives and future challenges. Acta Pharmaceutica Sinica B, 6(4), 287-296.

Haney, M. J., Klyachko, N. L., Zhao, Y., Gupta, R., Plotnikova, E. G., He, Z., . . . & Batrakova, E. V. (2015). Exosomes as drug delivery vehicles for Parkinson's disease therapy. Journal of Controlled Release, 207, 18-30.

Ho, R., Sances, S., Gowing, G., Amoroso, M. W., O'Rourke, J. G., Sahabian, A., . . . & Svendsen, C. N. (2016). ALS disrupts spinal motor neuron maturation and aging pathways within gene co-expression networks. Nature neuroscience, 19(9), 1256-1267.

International Search Report and Written Opinion dated Jun. 11, 2019, issued for PCT International Application No. PCT/IL2019/050401, filed Apr. 10, 2019.

Jarmalaviciute, A., & Pivoriūnas, A. (2016). Neuroprotective properties of extracellular vesicles derived from mesenchymal stem cells. Neural regeneration research, 11(6), 904.

Kalra, H., Adda, C. G., Liem, M., Ang, C. S., Mechler, A., Simpson, R. J., . . . & Mathivanan, S. (2013). Comparative proteomics evaluation of plasma exosome isolation techniques and assessment of the stability of exosomes in normal human blood plasma. Proteomics, 13(22), 3354-3364.

Kaplan, A., Spiller, K. J., Towne, C., Kanning, K. C., Choe, G. T., Geber, A., . . . & Henderson, C. E. (2014). Neuronal matrix metalloproteinase-9 is a determinant of selective neurodegeneration. Neuron, 81(2), 333-348.

Kaspar, B. K., Lladó, J., Sherkat, N., Rothstein, J. D., & Gage, F. H. (2003). Retrograde viral delivery of IGF-1 prolongs survival in a mouse ALS model. Science, 301(5634), 839-842.

Kassis, I., Zangi, L., Rivkin, R., Levdansky, L., Samuel, S., Marx, G., & Gorodetsky, R. (2006). Isolation of mesenchymal stem cells from G-CSF-mobilized human peripheral blood using fibrin microbeads. Bone marrow transplantation, 37(10), 967-976.

Katsuda, T., Tsuchiya, R., Kosaka, N., Yoshioka, Y., Takagaki, K., Oki, K., . . . & Ochiya, T. (2013). Human adipose tissue-derived mesenchymal stem cells secrete functional neprilysin-bound exosomes. Scientific reports, 3, 1197.

Kawasaki, Y., Xu, Z. Z., Wang, X., Park, J. Y., Zhuang, Z. Y., Tan, P. H., . . . & Ji, R. R. (2008). Distinct roles of matrix metalloproteases in the early-and late-phase development of neuropathic pain. Nature medicine, 14(3), 331-336.

Kern, S., Eichler, H., Stoeve, J., Klüter, H., & Bieback, K. (2006). Comparative analysis of mesenchymal stem cells from bone marrow, umbilical cord blood, or adipose tissue. Stem cells, 24(5), 1294-1301.

Knippenberg, S., Thau, N., Dengler, R., Brinker, T., & Petri, S. (2012). Intracerebroventricular injection of encapsulated human mesenchymal cells producing glucagon-like peptide 1 prolongs survival in a mouse model of ALS. PloS one, 7(6), e36857.

Koprich, J. B., Johnston, T. H., Huot, P., Reyes, M. G., Espinosa, M., & Brotchie, J. M. (2011). Progressive neurodegeneration or endogenous compensation in an animal model of Parkinson's disease produced by decreasing doses of alpha-synuclein. PloS one, 6(3), e17698.

Lai, R. C., Arslan, F., Lee, M. M., Sze, N. S. K., Choo, A., Chen, T. S., . . . & Pasterkamp, G. (2010). Exosome secreted by MSC reduces myocardial ischemia/reperfusion injury. Stem cell research, 4(3), 214-222.

Lai, R. C., Yeo, R. W. Y., & Lim, S. K. (Apr. 2015). Mesenchymal stem cell exosomes. In Seminars in cell & developmental biology (vol. 40, pp. 82-88). Academic Press.

Lamichhane, T. N., Raiker, R. S., & Jay, S. M. (2015). Exogenous DNA loading into extracellular vesicles via electroporation is size-dependent and enables limited gene delivery. Molecular pharmaceutics, 12(10), 3650-3657.

Lamparski, H. G., Metha-Damani, A., Yao, J. Y., Patel, S., Hsu, D. H., Ruegg, C., & Le Pecq, J. B. (2002). Production and characterization of clinical grade exosomes derived from dendritic cells. Journal of immunological methods, 270(2), 211-226.

Liu, C., Cui, G., Zhu, M., Kang, X., & Guo, H. (2014). Neuroinflammation in Alzheimer's disease: chemokines produced by astrocytes and chemokine receptors. International journal of clinical and experimental pathology, 7(12), 8342.

Lo Furno, D., Mannino, G., & Giuffrida, R. (2018). Functional role of mesenchymal stem cells in the treatment of chronic neurodegenerative diseases. *Journal of cellular physiology*, 233(5), 3982-3999.

Luan, X., Sansanaphongpricha, K., Myers, I., Chen, H., Yuan, H., & Sun, D. (2017). Engineering exosomes as refined biological nanoplatforms for drug delivery. Acta Pharmacologica Sinica, 38(6), 754-763.

Mirzayans, R., Andrais, B., & Murray, D. (2017). Impact of premature senescence on radiosensitivity measured by high throughput cell-based assays. International journal of molecular sciences, 18(7), 1460.

Petrou, P., Argov, A., Lennon, V. A., Gotkine, M., Kassis, I., Vaknin-Dembinsky, A., . . . & Karussis, D. (2014). Rare combination of myasthenia and motor neuronopathy, responsive to Msc-Ntf stem cell therapy. Muscle & Nerve, 49(3), 455-457.

Petrou, P., Gothelf, Y., Argov, Z., Gotkine, M., Levy, Y. S., Kassis, I., . . . & Melamed, E. (2016). Safety and clinical effects of mesenchymal stem cells secreting neurotrophic factor transplantation in patients with amyotrophic lateral sclerosis: results of phase 1/2 and 2a clinical trials. JAMA neurology, 73(3), 337-344.

Philips, T., & Rothstein, J. D. (2014). Glial cells in amyotrophic lateral sclerosis. Experimental neurology, 262, 111-120.

(56) References Cited

OTHER PUBLICATIONS

Pun, S., Santos, A. F., Saxena, S., Xu, L., & Caroni, P. (2006). Selective vulnerability and pruning of phasic motoneuron axons in motoneuron disease alleviated by CNTF. Nature neuroscience, 9(3), 408-419.

Quesenberry, P. J., Goldberg, L. R., Aliotta, J. M., Dooner, M. S., Pereira, M. G., Wen, S., & Camussi, G. (2014). Cellular phenotype and extracellular vesicles: basic and clinical considerations. Stem cells and development, 23(13), 1429-1436.

Sances, S., Bruijn, L. I., Chandran, S., Eggan, K., Ho, R., Klim, J. R., . . . & Sadegh, C. (2016). Modeling ALS with motor neurons derived from human induced pluripotent stem cells. Nature neuroscience, 19(4), 542-553.

Semenov, O. V., Koestenbauer, S., Riegel, M., Zech, N., Zimmermann, R., Zisch, A. H., & Malek, A. (2010). Multipotent mesenchymal stem cells from human placenta: critical parameters for isolation and maintenance of stemness after isolation. American journal of obstetrics and gynecology, 202(2), 193-e1.

Shtam, T. A., Kovalev, R. A., Varfolomeeva, E. Y., Makarov, E. M., Kil, Y. V., & Filatov, M. V. (2013). Exosomes are natural carriers of exogenous siRNA to human cells in vitro. Cell Communication and Signaling, 11(1), 1-10.

Uccelli, A., Milanese, M., Principato, M. C., Morando, S., Bonifacino, T., Vergani, L., . . . & Caponnetto, C. (2012). Intravenous mesenchymal stem cells improve survival and motor function in experimental amyotrophic lateral sclerosis. Molecular Medicine, 18(5), 794-804.

Weydt, P., Hong, S. Y., Kliot, M., & Möller, T. (2003). Assessing disease onset and progression in the SOD1 mouse model of ALS. Neuroreport, 14(7), 1051-1054.

Bonafede, R. et al. (2017). ALS pathogenesis and therapeutic approaches: the role of mesenchymal stem cells and extracellular vesicles. Frontiers in cellular neuroscience, 11, 80.

Braccioli, L. et al. (2014). Exosomes: a new weapon to treat the central nervous system. Molecular neurobiology, 49(1), 113-119.

Chang, Y. H. et al. (2018). Exosomes and stem cells in degenerative disease diagnosis and therapy. Cell Transplantation, 27(3), 349-363.

Fragkouli, A. et al. (2014). miR-7 and miR-153 protect neurons against MPP+-induced cell death via upregulation of mTOR pathway. Frontiers in cellular neuroscience, 8, 182.

Gimona, M. et al. (2017). Manufacturing of human extracellular vesicle-based therapeutics for clinical use. International journal of molecular sciences, 18(6), 1190.

Jaumotte, J. D. et al. (2014). Comparison of GDF5 and GDNF as neuroprotective factors for postnatal dopamine neurons in ventral mesencephalic cultures. Journal of neuroscience research, 92(11), 1425-1433.

Junn, E. et al. (2009). Repression of α-synuclein expression and toxicity by microRNA-7. Proceedings of the National Academy of Sciences, 106(31), 13052-13057.

Lekishvili, T. et al. (2006). Mouse galectin-1 inhibits the toxicity of glutamate by modifying NR1 NMDA receptor expression. European Journal of Neuroscience, 24(11), 3017-3025.

Liew, L. C. et al. (2017). Mesenchymal stem cell-derived extracellular vesicles: a glimmer of hope in treating Alzheimer's disease. International immunology, 29(1), 11-19.

McMillan, K. J. et al. (2017). Loss of microRNA-7 regulation leads to α-synuclein accumulation and dopaminergic neuronal loss in vivo. Molecular Therapy, 25(10), 2404-2414.

Miura, T. et al. (2004). Galectin-1β, a natural monomeric form of galectin-1 lacking its six amino-terminal residues promotes axonal regeneration but not cell death (Doctoral dissertation). Cell Death Differ, 11(10):1076-83.

Oh, S. H. et al. (2016). Mesenchymal stem cells inhibit transmission of α-synuclein by modulating clathrin-mediated endocytosis in a parkinsonian model. Cell reports, 14(4), 835-849.

Perillo, N. L. et al. (1998). Galectins: versatile modulators of cell adhesion, cell proliferation, and cell death. Journal of molecular medicine, 76(6), 402-412.

Phinney, D. G. et al. (2017). Concise review: MSC-derived exosomes for cell-free therapy. Stem cells, 35(4), 851-858.

Vizoso, F. J. et al. (2017). Mesenchymal stem cell secretome: toward cell-free therapeutic strategies in regenerative medicine. International journal of molecular sciences, 18(9), 1852.

Zhou, Y. et al. (2016). MicroRNA-7 targets Nod-like receptor protein 3 inflammasome to modulate neuroinflammation in the pathogenesis of Parkinson's disease. Molecular neurodegeneration, 11(1), 1-15.

\* cited by examiner

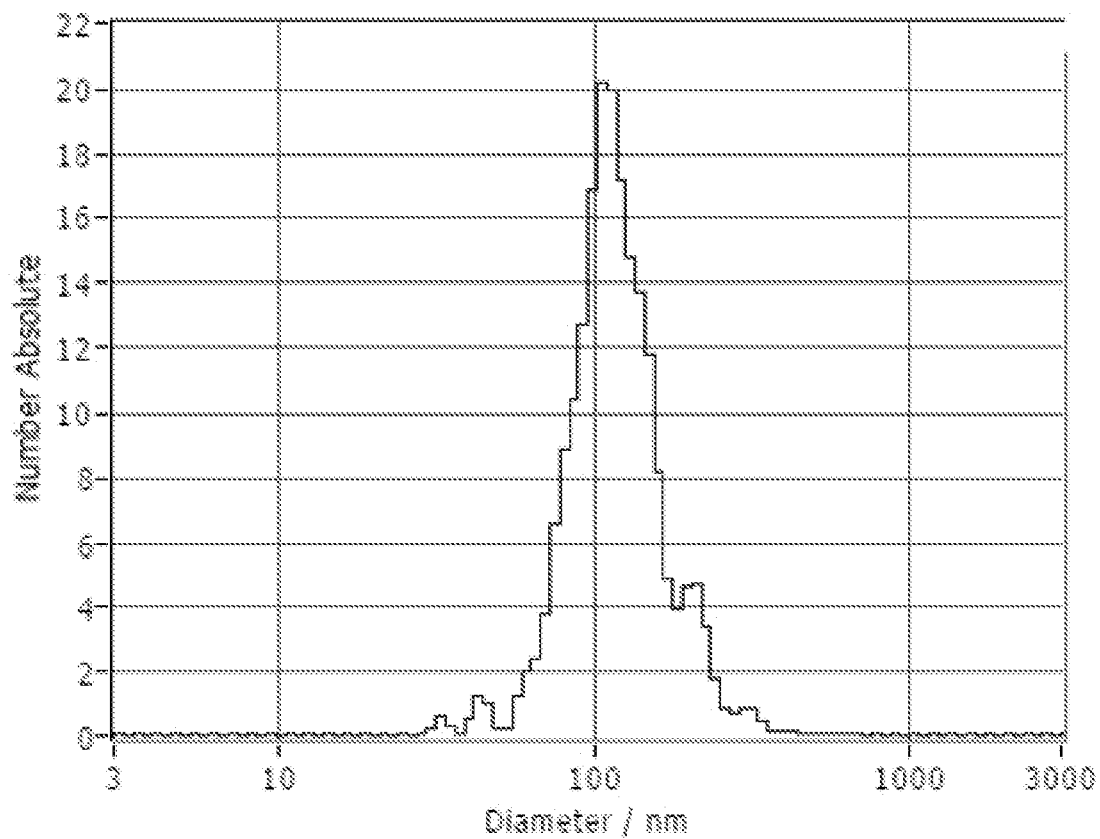
Figure 1
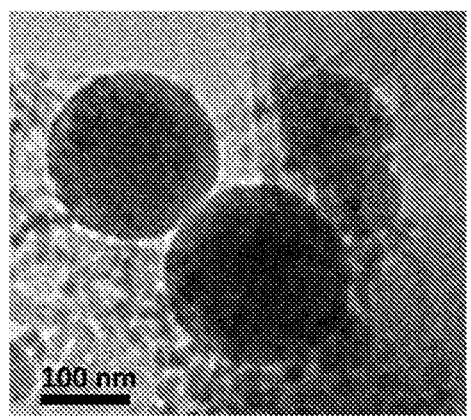 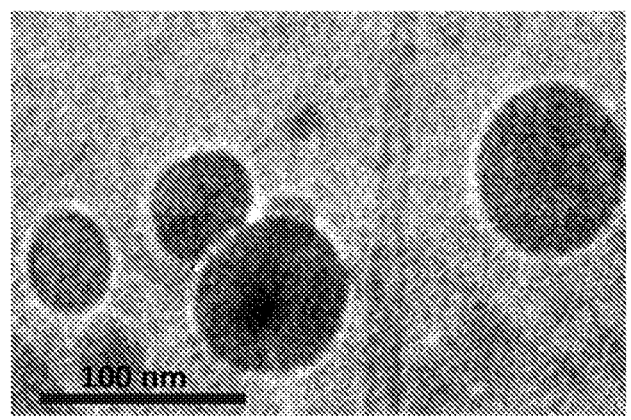
Figure 2A        Figure 2B

MSC-NTF SPECIFIC EXOSOMES AND USE THEREOF

CROSS REFERENCE TO RELATED APPLICATIONS

This application is a National Phase Application of PCT International Application No. PCT/IL2019/050401, International Filing Date Apr. 10, 2019, which claims the benefit of U.S. Provisional Application No. 62/665,558, filed May 2, 2018, and U.S. Provisional Application No. 62/655,249, filed Apr. 10, 2018, which are hereby incorporated by reference.

FIELD OF DISCLOSURE

The disclosure relates to isolated cell-type specific exosomes, wherein said cell-type comprises differentiated mesenchymal stem cells (MSC) that have been induced to secrete at least one neurotrophic factor (NTF). The differentiated cells are designated "MSC-NTF", MSC-NTF cells or NurOwn®. In addition, disclosed herein are modified isolated exosomes derived from MSC, wherein the exosomes comprise specific beneficial molecules. These isolated MSC-NTF exosomes and modified MSC exosomes may be used for treating neurodegenerative diseases, including amyotrophic lateral sclerosis (ALS) disease, frontotemporal dementia (FTD), Parkinson's Disease (PD), multiple system atrophy (MSA), spinal muscular atrophy (SMA), multiple sclerosis (MS), Alzheimer's Disease (AD), Rett Syndrome, Cerebral Palsy (CP), Autism Spectrum Disorder (ASD), and Epilepsy.

BACKGROUND

Neurodegenerative diseases are characterized by dysfunction associated with loss of neural cells in the brain and/or spinal cord. Acute neurodegeneration may result from a temporally discrete insult, such as stroke or trauma, leading to a localized loss of neurons at the site of injury. Chronic neurodegeneration may develop over a long period of time and results in the loss of a particular neuronal subtype or generalized loss of neuronal populations. In the brain, Alzheimer disease (AD) and Frontotemporal dementia (FTD) result in widespread loss of neurons, whereas Parkinson disease (PD) involves the specific and localized loss of dopaminergic (DA) neurons in the substantia nigra. In the brainstem and spinal cord, amyotrophic lateral sclerosis (ALS) and spinal muscular atrophy (SMA) involve the degeneration and loss of motor neurons (MNs). Multiple sclerosis (MS) is a demyelinating disease in which nerve cells in the brain and spinal cord are damaged. Additional neurodegenerative diseases include Alzheimer's Disease (AD), Rett Syndrome, Cerebral Palsy (CP), Autism Spectrum Disorder (ASD), and epilepsy. AD is a progressive brain disorder that damages and eventually destroys brain cells, leading to memory loss and changes in thinking and other brain functions. Rett Syndrome is a neurodevelopmental condition, most often caused by mutations in the gene MECP2 located on the X chromosome. CP is considered a neurological disorder caused by a non-progressive brain injury or malformation that occurs while the child's brain is under development. ASD is considered the most heritable of psychiatric disorders. Examination of ASD brains has revealed global changes including disorganized gray and white matter, increased number of neurons, decreased volume of neuronal soma, and increased neuropil, the last reflecting changes in densities of dendritic spines, cerebral vasculature and glia. Epilepsy is a disorder of the central nervous system characterized by recurrent seizures unprovoked by an acute systemic or neurologic insult.

Although these conditions all exhibit unique neuronal pathologies and the exact mechanisms for neuronal loss are complex, many neurodegenerative diseases display common pathophysiological processes including protein accumulation, mitochondrial dysfunction, oxidative stress, inflammation and apoptotic death. Current treatments are often symptomatic and do not stop or slow neurodegenerative processes. Interestingly, MSC cells have been investigated in the treatment of many different neurodegenerative diseases (Lo Furno et al (2018) J Cell Physiol. 233:3982-3999).

Mesenchymal stem cells (MSCs) are the most common type of adult stem cells used in clinical trials owing to their neuroprotective and immunomodulatory effects via a dynamic, paracrine interaction with host cells. Characteristics of MSC may include a lack of expression of cell surface membrane markers selected from the group CD45, CD34, CD14 or CD11b, CD79a or CD19, and HLA-DR; (Dominici M, Le Blanc K, Mueller I et al Minimal criteria for defining multipotent mesenchymal stromal cells. The International Society for Cellular Therapy position statement. Cytotherapy 2006; 8:315-317.) Thus, MSC may be defined by an absence of markers on their cell surface (negative markers).

NurOwn®, also known as MSC-NTF cells, are autologous bone marrow derived MSCs, induced under proprietary culture conditions to produce high levels of neurotrophic factors (NTFs) that support neuronal growth and survival including VEGF, HGF, GDNF and BDNF among others. MSC-NTF cells also secrete high levels of NTFs that are very low or not expressed by MSC, such as: LIF, G-CSF, BMP-2 and TSG-6. Furthermore, MSC-NTF cells express a unique gene, protein and miRNA pattern compared to undifferentiated MSCs that may regulate neurogenesis and modulate neuro-inflammation.

The MSC-NTF cell therapy has been evaluated in Phase I and Phase IIa, open-label trials in ALS patients and more recently in a US Phase 2 multicenter, randomized double-blind placebo-controlled study. These trials confirmed the safety and tolerability of MSC-NTF cells administered either intrathecally (IT) or intramuscularly (IM) or by a combination of the two routes. Significant clinical efficacy was observed, more notably in rapidly progressing ALS participants after a single administration of MSC-NTF cells. In addition, 2-weeks post transplantation, a significant increase in MSC-NTF cell-specific NTFs was detected in the cerebrospinal fluid (CSF) of treated but not of placebo patients. Furthermore, a statistically significant inverse correlation was identified between increased NTFs and a reduction in inflammatory markers in the CSF of MSC-NTF cells-treated patients but not in placebo-treated patients. Moreover, analyses of cell-specific and ALS characteristic miRNAs identified in the CSF of study participants supported the proposed anti-inflammatory and neurotrophic mechanism of action. A multicenter ALS phase 3 double-blind placebo controlled multidose study of MSC-NTF cells is currently underway at six US medical centers.

It would be of benefit to those suffering neurodegenerative diseases such as ALS, Parkinson's Disease, and Multiple Sclerosis to have a therapy that maintains the therapeutic potential of MSC-NTF cells, while improving the therapy by providing practical advantages to MSC-NTF cells.

SUMMARY

Exosomes are nano-sized (usually 30-150 nm in diameter) cell-secreted vesicles that are released by different cell types, including MSCs. Exosomes originate in multivesicular bodies and are released into the extracellular environment after fusion with the plasma membrane. Exosomes participate in cell-to-cell communication by delivering their cargo that may include miRNA, mRNA, lipids, and proteins from their cells of origin, ultimately providing regulatory functions for many cell processes, including modulating inflammation, angiogenesis and neuronal survival and differentiation.

The use of exosome-based therapy over cell-based therapy (e.g. MSCs therapy) has several practical advantages. One of the advantages is that exosomes readily cross the blood brain barrier (BBB) and penetrate into deep CNS tissues (Alvarez-Erviti, 2011 Neurobiol Dis. 42 (3):360-7), while intact cells do not. Another advantage of exosomes is that they have high product stability as they are inert in nature, while living cells have a short shelf-life and necessitate constant regulation. Another advantage of exosomes is that they are very easy to formulate for dosing, e.g. in high dosages and high concentration, which enhances their therapeutic effects (Kalra, 2013 Proteomics. 13(22):3354-64). Another advantage of exosomes is that they possess low immunogenicity, e.g. exhibit an increased capacity to escape degradation or clearance by the immune system, allowing repeated administrations (Luca, 2014 Mol Neurobiol 49(1) 113-119). It is important to note that the non-to-low immunogenicity of exosomes provides, in stark contrast to cell therapy, the option to commercially pre-produce, characterize, test and store large quantities of therapeutic products, and that these products can further be administered to any recipient without the need for immunological-matching. An omni-donor-omni-recipient therapeutics represents a huge advantage over all cell-based therapies, which necessitate a closed "patient administered with his own cells" system.

Further, and in contrast to cells, exosomes have no potential to trans-differentiate into cells of different lineages and no potential for DNA transformation. In addition, exosomes possess ideal innate structural and biocompatible nanocarrier properties for a functional transport of low molecular-weight therapeutics, nucleic acids, and proteins.

Disclosed herein, in one aspect is an isolated exosome population derived from mesenchymal stem cells secreting-neurotrophic factors (MSC-NTF cells), said isolated exosomes comprising an increased quantity of at least one cargo protein comprising a neurotrophic factor (NTF), compared with the quantity of said at least one cargo protein in an isolated exosome population derived from control MSCs.

In a related aspect, the NTF comprises a leukemia inhibitory factor (LIF) protein, a vascular endothelial growth factor A (VEGFA) protein, or a growth differentiation factor 15 (GDF15) protein, or any combination thereof. In another related aspect, an at least one cargo protein comprises an NTF and at least one an additional protein. In a further related aspect, the addition protein comprises a chemokine (C-X-C Motif) Ligand 1 (CXCL1) protein or an interleukin 13 (IL13) protein, or a combination thereof. In another related aspect, the quantity of LIF protein is increased at least 50-fold, or the quantity of CXCL1 protein is increased at least 30-fold, or the quantity of IL13 protein is increased at least 5-fold, or the quantity of VEGFA is increased at least 5-fold, or the quantity of GDF15 is increased at least 2-fold, or any combination thereof. In another related aspect, the at least one additional protein comprises a IL36A, a CCL7, a MMP10, a PIFG, a CXCL8, a LTA, a CXCL6, an MMP3, a CHI3L1, an IL11, a FGF2, a CXCL5, a GAS1, a JAML, a TGFBR3, a MEPE, a IL6, a PDGFA, a CCL4, a CCL21, a CCL2, a MIF, a PLAU, an ANGPTL4, a CTSB, a BSG, a CCL5, a TPO, a IL23, a IL1RL1, a SPP1, a F11R, an INHBA, a FAP, a SPINT2, a IL36G, a TNFRSF10B or a TNFSF14 protein, or any combination thereof.

In another aspect, the isolated, exosome population further comprises one or more markers selected from the group consisting of cluster of differentiation (CD)9, CD29, CD63, CD81, CD44, CD49, CD73, CD90, CD105, CD61, CD271, ALIX, tumor susceptibility gene (TSG)101, and any combination thereof; or is devoid of one or more markers selected from the group consisting of CD3, CD5, CD14, CD19, CD20, CD34, CD45, CD11B, FMC7, calnexin, human leukocyte antigen-antigen D related (HLA-DR), and any combination thereof; or any combination thereof.

In a related aspect, the MSCs are selected from the group consisting of bone marrow MSCs, adipocyte MSCs, dental pulp MSCs, placenta MSCs, synovial membrane MSCs, peripheral blood MSCs, oral mucosa MSCs, periodontal ligament MSCs, endometrium MSCs, umbilical cord MSCs, and umbilical cord blood MSCs.

In another related aspect, the isolated exosome population further comprises one or more neurotrophic factors (NTF) selected from the group consisting of a hepatocyte growth factor (HGF), a granulocyte stimulating factor (G-CSF), a brain-derived neurotrophic factor (BDNF), a tumor necrosis factor-inducible gene 6 protein (TSG-6; also known as TNF-stimulated gene 6 protein), a bone morphogenetic protein 2 (BMP2), and a fibroblast growth factor 2 (FGF2), and any combination thereof. In a further related aspect, the isolated exosome population further comprises one or more miRNA molecule selected from the group consisting of miRNA (miR)-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, and miR-4324, and any combination thereof; or wherein the isolated exosome population is devoid of one or more miRNA molecule selected from the group consisting of miR-503, miR-3659, miR-3529-3p, miR-320b, miR-1275, miR-3132, miR-320a, miR-495, miR-181b-5p, miR-222-3p, miR-424-5p, miR-4284, miR-574-5p, miR-143-3p, miR-106a-5p, miR-455-3p, miR-20a-5p, miR-145-5p, miR-324-3p, miR-130b-3p, miR-1305, and miR-140-3p, and any combination thereof; or any combination thereof.

The disclosure herein describes in one aspect, a pharmaceutical composition comprising an isolated exosome population derived from mesenchymal stem cells secreting-neurotrophic factors (MSC-NTF cells), said isolated exosomes comprising an increased quantity of at least one cargo protein comprising a neurotrophic factor (NTF), compared with the quantity of said at least one cargo protein in an isolated exosome population derived from control MSCs, and a pharmaceutically acceptable carrier.

In one aspect, disclosed herein is a pharmaceutical composition for use in a method of treating a neurodegenerative disease, said pharmaceutical composition comprising an isolated exosome population derived from mesenchymal stem cells secreting-neurotrophic factors (MSC-NTF cells), said isolated exosomes comprising an increased quantity of at least one cargo protein comprising a neurotrophic factor (NTF), compared with the quantity of said at least one cargo protein in an isolated exosome population derived from control MSCs.

In a related aspect, the method of use comprises an immunomodulatory effect selected from the group consisting of decreasing $CD4^+$ T-cell proliferation, inducing of T regulatory (T-reg) cells, decreasing IFN-γ secretion, decreasing TNF-α secretion, and any combination thereof.

In a related aspect, the neurodegenerative disease is selected from the group consisting of Amyotrophic Lateral Sclerosis (ALS), frontotemporal dementia (FTD), Parkinson's disease, Multiple System Atrophy (MSA), Spinal Muscular Atrophy (SMA), Multiple Sclerosis (MS), Alzheimer's Disease (AD), Rett Syndrome, Cerebral Palsy (CP), Autism Spectrum Disorder (ASD), and Epilepsy.

In one aspect, disclosed herein is a method of producing an isolated exosome population comprising an increased quantity of at least one cargo protein, said cargo protein comprising an NTF, the method comprising the steps of: (a) obtaining human mesenchymal stem cells (MSCs), (b) isolating adherent mesenchymal stem cells (MSCs), (c) culturing the adherent mononuclear cells with a serum free DMEM medium supplemented with dibutyryl cyclic adenosine monophosphate, human basic fibroblast growth factor, human platelet-derived growth factor, and of human heregulin-β1, and (d) isolating an exosome population from the serum free DMEM medium; wherein said increased quantity is compared with the quantity of said at least one cargo protein in an isolated exosome population derived from undifferentiated MSCs.

In a related aspect, the MSCs are selected from the group consisting of bone marrow MSCs, adipocyte MSCs, dental pulp MSCs, placenta MSCs, synovial membrane MSCs, peripheral blood MSCs, oral mucosa MSCs, periodontal ligament MSCs, endometrium MSCs, umbilical cord MSCs, and umbilical cord blood MSCs. In a further related aspect, when said MSC comprise bone marrow MSCs, peripheral blood MSCs, or umbilical cord blood MSCs, said step (a) further comprises separating human mononuclear cells from said bone marrow or said blood, and step (b) further comprises isolated adherent MSC from the mononuclear population.

In a related aspect, wherein step (b) further comprises propagating the adherent mononuclear cells in low glucose DMEM supplemented with 200 mM L-Glutamine, 100 mM Sodium Pyruvate, 2 IU/ml Heparin and 10% platelet lysate.

In a related aspect, wherein the serum free DMEM medium in step (c) is supplemented with 1 mM of dibutyryl cyclic adenosine monophosphate, 20 ng/mL of human basic fibroblast growth factor, 5 ng/mL of human platelet-derived growth factor, and 50 ng/mL of human heregulin-β1.

In a related aspect, wherein step (d) is performed 3 days after step (c).

In one aspect, disclosed herein is an isolated exosome population derived from mesenchymal stem cells secreting neurotrophic factors (MSC-NTF cells), said isolated exosomes comprising an increased quantity of at least one cargo protein compared with the quantity of said at least one cargo protein in an isolated exosome population derived from control MSCs, said cargo protein comprising an NTF, said isolated exosome population produced by a method comprising the steps of: (a) obtaining human mesenchymal stem cells (MSCs), (b) isolating adherent mesenchymal stem cells (MSCs), (c) culturing the adherent mononuclear cells with a serum free DMEM medium supplemented with dibutyryl cyclic adenosine monophosphate, human basic fibroblast growth factor, human platelet-derived growth factor, and of human heregulin-β1, and d) isolating an exosome population from the serum free DMEM medium.

BRIEF DESCRIPTION OF THE DRAWINGS

The subject matter of the isolated exosomes, methods of isolation and uses thereof, is particularly pointed out and distinctly claimed in the concluding portion of the specification. However, objects, features, and advantages of the isolated exosome, methods of isolation and uses thereof, may best be understood by reference to the following detailed description when read with the accompanying drawings in which:

FIG. 1 is a line graph showing exosome size (diameter, nm) and number distribution. Exosomes size and number were measured by nanoparticle tracking analysis. The mean diameter of exosomes isolated from MSC-NTF cells was about 130 nm.

FIGS. 2A-2B are two electron micrographs showing exosomes isolated from MSC-NTF cell culture medium by Tangential Flow Filtration (TFF). Exosomes were fixed in 2% paraformaldehyde and 2% glutaraldehyde, loaded onto a 200 mesh lacey Formvar carbon-coated grids and immediately frozen in ethane (gas).

FIG. 4D is an illustration of an increase of CD4$^+$CD25$^+$FoxP3$^+$ T-reg levels in PBMCs from two different healthy donors co-cultured for 3 days with MSC-NTF exosomes in at two different doses ($4.6 \times 10^9$ and $2.3 \times 10^9$) as determined by flow cytometry. FIG. 4E is an illustration of a correlation between MSC-NTF exosomes and induction of CD4$^+$CD25$^+$FoxP3$^+$ (T-reg) cells from PBMCs. The dot plot shows the distribution of FoxP3 and CD25 positive cells. Exosomes at two different doses ($4.6 \times 10^9$ and $2.3 \times 10^9$) were co-cultured with PBMC for 3 days and the phenotype of T-regs was evaluated. Control is PBS+PBMC. All the cells are CD4$^+$.

FIG. 5A shows the results of experiments examining induction of neurite outgrowth as determined by the change in length of the neurites, monitored at 6 hours intervals, on DCX-GFP neural precursors to which either 1, 10 or 20 μl of MSC-NTF exosomes were added (Cells with PBS—control). FIG. 5B is an illustration of a neuroprotective effect of MSC-NTF exosomes. Neural progenitor cells derived from iPSCs were differentiated into mature neurons for 14 days using neuron differentiation and maturation medium. On day 15 medium was changed to neurotrophic factor-deprived medium supplemented with exosomes (2-4×10$^9$ particles) or PBS (control). Cells were maintained in culture for 7 additional days. Cells were imaged during this time at 6 hours intervals. Neurite length change was calculated using the Neurotrack module. FIG. 5C is an illustration of a neurite outgrowth effect of MSC exosomes and MSC-NTF exosomes. SH-SY5Y cells were seeded in 96 well plates in DMEM F12 supplemented with 10% FBS at a cell density of 35,000 cells/cm$^2$. 24 hours later medium was replaced with serum free DMEM F12, and exosomes (~2×10$^9$ particles) were added to each well. Control was PBS. Cells were imaged at 2 hours intervals. Neurite length was calculated by using the Neurotrack module.

DETAILED DESCRIPTION

Figure 3A:
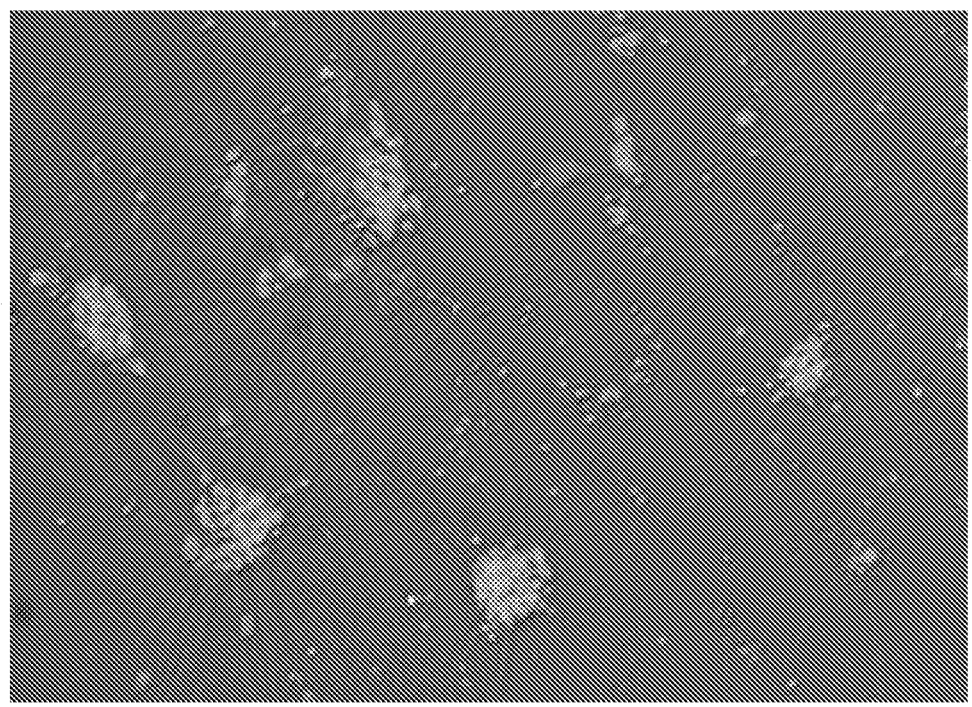
FIGS. 3A-3B present the results of uptake of exosomes by cultured neurons. Exosomes were stained with an RNA selective dye (FIG. 3A) or by membrane staining (FIG. 3B) and co-cultured with iPSC human neurons for 12 hours. Uptake was assessed by Fluorescence Microscopy (FIG. 3A, magnification ×10) and FACS analysis (FIG. 3B; SS is Side Scatter and FL1 refers to fluorescence channel 1-480 nm).

In the following detailed description, numerous specific details are set forth in order to provide a thorough understanding of the isolated exosomes, methods of isolation and uses thereof. In other instances, well-known methods, procedures, and components have not been described in detail so as not to obscure the isolated exosomes, methods of isolation and uses thereof.

Described herein are isolated "cell-type specific" exosomes, wherein the cell-type comprises differentiated mesenchymal stem cells (MSC) that have been induced to secrete at least one neurotrophic factor (NTF). Such cells are designated herein "MSC-NTF" or "MSC-NTF cells". A skilled artisan would appreciate that the term "MSC-NTF cells" is used herein interchangeably with "MSC-NTF" or "NurOwn®" having all the same qualities and meanings.

Specifically, described herein are methods of producing exosomes from MSC-NTF cells. Exosomes isolated from MSC-NTF cells may be used, even without the MSC-NTF cells, for treating neurodegenerative diseases, including amyotrophic lateral sclerosis (ALS) disease, frontotemporal dementia (FTD), Parkinson's Disease (PD), multiple system atrophy (MSA), spinal muscular atrophy (SMA), multiple sclerosis (MS), Alzheimer's Disease (AD), Rett Syndrome, Cerebral Palsy (CP), Autism Spectrum Disorder (ASD), and epilepsy.

Characterization of the isolated MSC-NTF exosomes includes at least a subset of the markers that define and characterize MSC-NTF cells. These markers may include membrane markers, NTF, and miRNAs. Further, those markers may be altered in MSC-NTF compared with non-differentiated MSC, and may also be altered in the isolated exosomes of MSC-NTF compared with isolated exosomes of MSC. Additionally, the exosomes may be modified by loading them with beneficial "cargo" factors, for example insulin-like growth factor (IGF)-1 and -2, or GDF-5, or galectin-1. Other exemplary "cargo" factors may be siRNA or miRNA that target molecules known to target vulnerable motor neurons, for example matrix metalloproteinase-9 (MMP-9) and miR-7.

Further described herein are exosomes isolated from mesenchymal stem cells (MSCs) that have been modified to comprise at least one molecule beneficial for the treatment of neurodegenerative diseases. These isolated MSC exosomes may be loaded to include beneficial molecules including but not limited to any of IGF-1, IGF-2, GDF-5, galectin-1, siRNA encoding a nucleotide sequence complementary to MM9 mRNA or a portion thereof, or miR-7, or any combination thereof. These modified MSC exosomes may also be used for treating neurodegenerative diseases, including amyotrophic lateral sclerosis (ALS) disease, frontotemporal dementia (FTD), Parkinson's Disease (PD), multiple system atrophy (MSA), spinal muscular atrophy (SMA), multiple sclerosis (MS), Alzheimer's Disease (AD), Rett Syndrome, Cerebral Palsy (CP), Autism Spectrum Disorder (ASD), and epilepsy. Specifically, described herein are methods of producing modified MSC exosomes comprising at least one beneficial molecule.

An advantage of loading MSC-NTF or MSC derived exosomes with beneficial molecules may be that these loaded exosomes provide both the benefit of the cell type from which they have been isolated and the benefit of the specifically selected molecules with which they have been loaded (and thus have been modified). Loading of exosomes may be directly at the level of the isolated exosome using methods known in the art, for example, electroporation, or the MSC or MSC-NTF cells may be modified to highly express or express at least one beneficial molecule prior to exosome isolation, so that the isolated exosome would then include the beneficial molecule upon formation.

In some embodiments, disclosed herein is an isolated cell-type specific exosome, wherein said cell-type comprises differentiated MSC that have been induced to secrete at least one neurotrophic factor (NTF), MSC-NTF cells, and wherein the basal secretion of said at least one NTF is greater in said MSC-NTF compared with the basal secretion of said at least one NTF in a non-differentiated MSC. An advantage of isolating cell-type specific exosome is the benefit provided from the components present in the MSC-NTF, that in some embodiments may also be present in exosome isolated from these cells, thus producing a therapy comprising beneficial components and lacking the issues that may arise with cell therapies.

As used herein the term "basal secretion" refers to a secretion which does not involve addition of stimulants. MSC-NTF cells may be produced from non-differentiated MSC using methods described herein. Thus typically, the non-differentiated mesenchymal stem cell is in an identical medium to the MSC-NTF cells but without the addition of differentiating agents.

A skilled artisan would appreciate that the term "isolated" as used herein refers to a cell that has been removed from its in-vivo location (for example but not limited to bone marrow, neural tissue, adipose tissue, dental pulp, placenta, synovial membrane, peripheral blood, oral mucosa, periodontal ligament, endometrium, umbilical cord, and umbilical cord blood). In one embodiment, an isolated cell is substantially free from other substances (e.g., other cell types) that are present in its in-vivo location.

Further, the skilled artisan would appreciate that the term "isolated" is also used herein to refer to an exosome that has been isolated from a cell, for example an MSC or differentiated MSC cell. In some embodiments, there is a strong correlation between the profile of an MSC and exosomes isolated from these cells, e.g. in terms of membrane markers and internal cargo. In some embodiments, there is a strong correlation between the profile of an MSC-NTF and exosomes isolated from these cells. Most notably in some embodiments, there is a correlation between the profile of NTF and/or miRNA molecules present in the isolated or purified exosomes and the NTF and/or miRNA profile of the corresponding MSC-NTF cells, from which they have been isolated.

A skilled artisan would appreciate that that term "isolated exosome", may in some embodiments be used interchangeable with "purified exosome" or "purified fraction of exosome", having all the same meanings and qualities.

As used herein, the singular form "a", "an" and "the" include plural references unless the context clearly dictates otherwise. For example, the term "an exosome" or "at least one exosome" may include a plurality of exosomes.

In other embodiments, there is a correlation between the profile of molecules that are highly expressed in genetically modified MSC cells and the content of these molecules in exosomes isolated from the genetically modified MSC cells, for example growth factors that may be highly expressed. In other embodiments, there is a correlation between the profile of siRNA molecules that are specifically expressed in genetically modified MSCs and the content of these siRNA molecules in exosomes isolated from the genetically modified MSCs. Examples of siRNA molecules include those that could reduce target peptides or polypeptides involved in neurodegenerative diseases. In some embodiments, there is a correlation between the profile of MSC marker molecules present in the isolated or purified exosomes and the marker molecule profile of the corresponding MSCs, from which they have been isolated.

In other embodiments, there is a correlation between the profile of molecules that are highly expressed in MSC-NTF cells (MSC-NTFs) and the quantity of these molecules in exosomes isolated from the MSC-NTFs, for example growth factors that may be highly expressed in MSC-NTF cells and found in a high quantity in exosomes derived from these cells. In some embodiments, the MSC-NTFs may be genetically modified to highly express a molecule beneficial in the treatment of neurodegenerative diseases. In some embodiments, molecules beneficial in the treatment of neurodegenerative diseases are highly expressed in MSC-NTFs compared with non-differentiated MSCs. In other embodiments, there is a correlation between the profile of siRNA molecules that are specifically expressed in genetically modified MSC-NTFs and the presence of these siRNA molecules in exosomes isolated from the MSC-NTFs, for example siRNA molecules reduce target peptides of polypeptides involved in neurodegenerative diseases. In some embodiments, there is a correlation between the profile of MSC-NTF marker molecules present in the isolated or purified exosomes and the marker molecule profile of the corresponding MSC-NTFs, from which they have been isolated.

As used herein, in some embodiments, the term "express" may encompass the synthesis and/or secretion of a neurotrophic factor (NTF), a miRNA, or an siRNA, as described herein. In some embodiments, the term "express" may encompass the synthesis and/or secretion of a miRNA as described herein. In some embodiments, the term "express" may encompass the synthesis and/or secretion of an siRNA as described herein. In some embodiments, expression of an NTF, a miRNA, or a siRNA in MSC-NTFs results in an increased content of that NTF, miRNA, or siRNA in an exosome isolated from the MSC-NTFs compared with exosomes isolated from MSCs or MSC-NTFs that do not express the NTF, miRNA, or siRNA. In some embodiments, expression of a growth factor, a miRNA, or a siRNA in a genetically modified MSCs results in an increased content of that growth factor, miRNA, or siRNA in an exosome isolated from the genetically modified MSCs compared with exosomes isolated from MSCs that has not been genetically modified to express the growth factor, miRNA, or siRNA. In some embodiments, expression comprises highly expression. In some embodiments, expression comprises a high level of expression.

In some embodiments, disclosed herein are markers of MSC-NTFs and/or MSCs, wherein the markers are identified using the gene name. The skilled artisan would appreciate that while the gene name is used to identify the marker, the marker itself is a polypeptide and increases and decreases in gene expression, may result in increases and decreases of the level of the identified polypeptide, respectively.

The disclosure presented herein relates broadly to isolated exosomes, methods of producing the exosomes, compositions thereof, and methods of their use in the treatment of certain diseases or disorders, including neurodegenerative disorders.

Mesenchymal Stem Cells (MSC) &Differentiated Mesenchymal Stem Cells (MSC-NTF)

The term "mesenchymal stem cell" "mesenchymal stromal cell", "Multipotent Stromal Cells", "MSC", or "MSCs" is used interchangeably for adult cells, which are not terminally differentiated, which can divide to yield cells that are either stem cells, or which irreversibly differentiate to give rise to cells of a mesenchymal cell lineage or transdifferentiate into cells of other non-mesodermal lineages such as the neural lineage.

Figure 7:
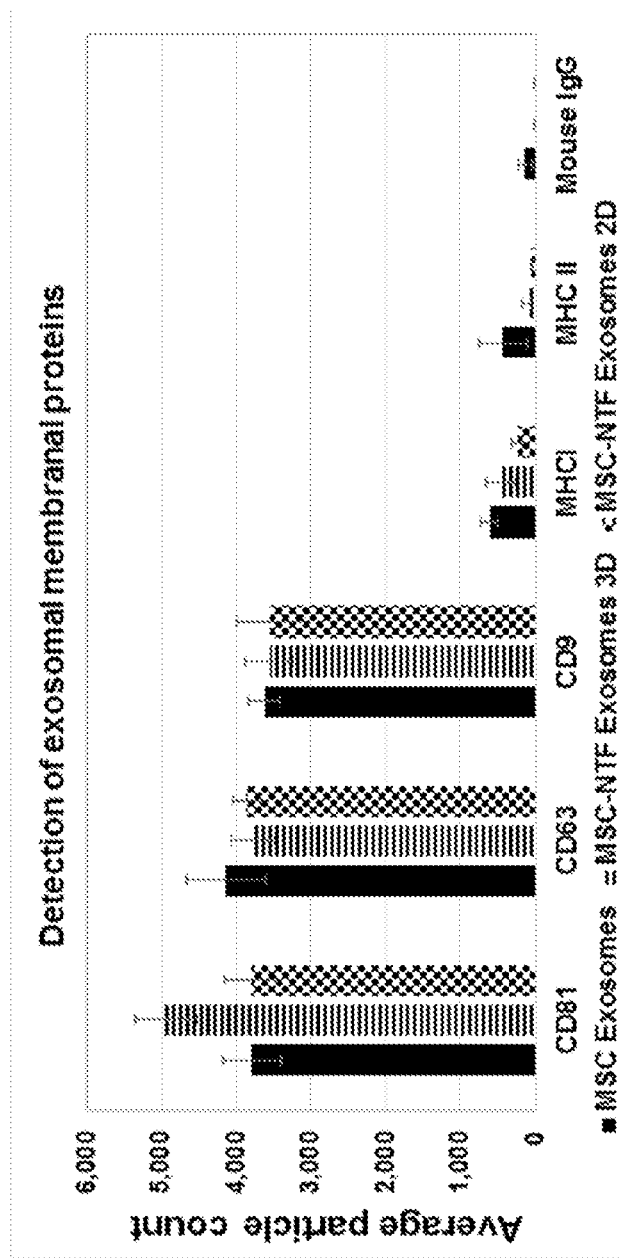
FIG. 7 shows the expression level of exosome markers CD81, CD63, and CD9 in exosomes isolated from MSC and MSC-NTF cell culture conditioned media, and of MHC-I and MHC-II molecules. Mouse IgG was used as negative control. MSC-NTF cells were grown under 2D and 3D conditions, as identified.

The source of MSCs may be from a healthy subject or may be from a subject to be treated or may be from a donor which is immunologically-matched or immunologically-unmatched with the subject to be treated. In some embodiments, the source of MSCs may be from a subject suffering from a neurodegenerative disease. In some embodiments, MSCs comprise autologous cells. In an alternative embodiment, MSCs comprise allogeneic cells. As exemplified herein, MSC exosomes and MSC-NTF exosomes barley express MHC-I and MHC-II molecules (FIG. 7), which may make immunologically-matching between exosomes and human recipients redundant.

MSCs can be found in nearly all tissues and may be isolated from various tissues. Although the bone marrow (BM) is the most widely recognized source of MSCs, recent research has identified alternative sources of MSCs, including adipose tissue (AT), placenta, dental pulp, synovial membrane, peripheral blood, oral mucosa, periodontal ligament, endometrium, umbilical cord (UC), and umbilical cord blood (UCB). In fact, evidence has suggested that MSCs may be present virtually in any vascularized tissues throughout the whole body.

In some embodiments, MSCs described herein were isolated from any tissue in which they are identified. In some embodiments, the tissue from which MSC may be isolated includes, but is not limited to, bone marrow, adipose tissue, placenta, dental pulp, synovial membrane, peripheral blood, oral mucosa, periodontal ligament, endometrium, umbilical cord, and umbilical cord blood.

A method of isolating MSCs from peripheral blood is described by Kassis et al (Bone Marrow Transplant. 2006 May; 37(10):967-76). A method of isolating MSCs from placental tissue is described by Semenov et al. (Semenov O V et al. Am J Obstet Gynecol. 2010 February; 202(2):193). Methods of isolating and culturing adipose tissue, placental and cord blood MSCs are described by Kern et al (Stem Cells, 2006; 24:1294-1301). In some embodiments, any method known in the art may be used for isolating MSCs from a tissue in which they are identified.

It will be appreciated that the MSCs described herein may be derived from any stem cell. In one embodiment, MSC cells comprise bone marrow MSCs. In another embodiment, MSC cells comprise adipocyte MSCs. In another embodiment, MSC cells comprise dental pulp MSCs. In another embodiment, MSC cells comprise MSCs obtained from tendon. In another embodiment, MSC cells comprise MSCs obtained from placenta. In another embodiment, MSC cells comprise MSCs obtained from umbilical cord. In another embodiment, MSC cells comprise MSCs obtained from adipose tissue. In another embodiment, MSC cells comprise MSCs obtained from synovial membrane. In another embodiment, MSC cells comprise MSCs obtained from peripheral blood. In another embodiment, MSC cells comprise MSCs obtained from periodontal ligament. In another embodiment, MSC cells comprise MSCs obtained from oral mucosa. In another embodiment, MSC cells comprise MSCs obtained from endometrium. In another embodiment, MSC cells comprise MSCs obtained from umbilical cord blood. In another embodiment, MSC are not derived from embryonic stem (ES) cells. In another embodiment, MSC comprise adult stem cells.

According to some embodiment, the MSCs are human. In some embodiment, the MSCs are autologous to a subject. In some embodiment, the MSCs are immunologically-matched to a subject. In other embodiments, the MSCs are non-autologous to a subject. In another embodiment, the MSCs are allogeneic to a subject.

In some embodiments, MSCs are obtained from a healthy subject. In some embodiments, MSCs are obtained from a subject suffering from a neurodegenerative disease. In some embodiments, MSCs are obtained from a subject suffering from a neurodegenerative disease comprising Amyotrophic Lateral Sclerosis (ALS), frontotemporal dementia (FTD), Parkinson's disease (PD), Multiple System Atrophy (MSA), Spinal Muscular Atrophy (SMA), Multiple Sclerosis (MS), Alzheimer's Disease (AD), Rett Syndrome, Cerebral Palsy (CP), Autism Spectrum Disorder (ASD), or epilepsy. In some embodiments, MSCs are obtained from a subject suffering from ALS. In some embodiments, MSCs are obtained from a subject suffering from FTD. In some embodiments, MSCs are obtained from a subject suffering from PD. In some embodiments, MSCs are obtained from a subject suffering from MSA. In some embodiments, MSCs are obtained from a subject suffering from MS. In some embodiments, MSCs are obtained from a subject suffering from AD. In some embodiments, MSCs are obtained from a subject suffering from Rett Syndrome. In some embodiments, MSCs are obtained from a subject suffering from CP. In some embodiments, MSCs are obtained from a subject suffering from ASD. In some embodiments, MSCs are obtained from a subject suffering from epilepsy.

In some embodiments, the MSCs are not or non-genetically modified. In some embodiments, MSCs are human cells. In one embodiment, bone marrow can be isolated from the iliac crest of an individual by aspiration. BM mononuclear cells (BMMNC) may be separated by, for example, a FICOLL-PAQUE density gradient centrifugation. In order to obtain MSCs, a cell population comprising the MSCs (e.g. BMMNC) may be cultured in a proliferating medium capable of maintaining and/or expanding the cells in the presence of, for example, platelet lysate. According to some embodiments, the populations are plated on polystyrene plastic surfaces (e.g. in a tissue culture flask) and MSCs are isolated by removing non-adherent cells. According to some embodiments, the populations are plated on polymeric surfaces present within a chamber of a bioreactor, and MSCs are isolated by removing non-adherent cells from within the bioreactor chamber. According to some embodiments, the populations are plated on surfaces able to accommodate adherent cell growth, wherein said surfaced are within a chamber of a bioreactor, and MSCs are isolated by removing non-adherent cells from within the bioreactor chamber. Alternatively, MSC may be isolated by FACS sorting using antibodies to MSC markers.

In some embodiments, MSCs are modified to express at least one molecule beneficial to the treatment of neurodegenerative diseases. Methods to express exogenous molecules in cells are well known in the art. In some embodiments, MSCs are genetically modified to express at least one molecule beneficial to the treatment of neurodegenerative diseases. In some embodiments, MSCs may be genetically modified to highly express at least one molecule beneficial to the treatment of neurodegenerative diseases. In some embodiments, molecules beneficial to the treatment of neurodegenerative diseases include growth factors, miRNA, and/or siRNA.

According to another embodiment, the MSC and/or MSC-NTF cells are grown in 3D cultures in bioreactors. An example of a bioreactor that may be used for MSC-NTF cell growth is the PBS Vertical-Wheel Bioreactor. PBS Vertical-Wheel Bioreactor has a vertical-agitation technology which results in homogenous mixing of the microcarriers beads. PBS Vertical-Wheel Bioreactor allows scaling of production from an adherent cell population in a controlled environment, and the highly integrated single-use equipment can be adapted to meet current good manufacturing practices requirements.

According to another embodiment, the MSC and/or MSC-NTF cells are grown in a bioreactor designed for high-density growth of adherent cells. In some embodiments, high density growth comprises a system having low shear stress, or zero foaming and bubbling, or no oxygen limitations, or any combination thereof an example of a bioreactor designed for high-density growth and high-productivity is a CelCradle™ (single-use, closed, and automated bioreactor) by VacciXcell (bioprocessing division of Esco Group of Companies). In some embodiments, a high-density bioreactor system comprises a single use bioreactor.

In some embodiments, the yield of purified exosomes is increased when MSC and/or MSC-NTF cells are grown in a high-density bioreactor system. In some embodiments, the yield of purified exosomes is increased when MSC and/or MSC-NTF cells are grown in a bioreactor system comprising three-dimensional growth (3D growth). In some embodiments, the yield of purified exosomes is increased when MSC and/or MSC-NTF cells are grown in a high-density bioreactor system comprising three-dimensional growth. In some embodiments, the exosomes isolated from MSC-NTF grown under 2D growth conditions and 3D growth conditions have a similar cargo profile. In some embodiments, the exosomes isolated from MSC-NTF grown under 2D growth conditions and 3D growth conditions have similar functional properties.

In some embodiments, there is an increased yield of purified exosomes when the cells from which the exosomes are secreted, are grown under conditions of three-dimensional growth, as compared with two-dimensional growth conditions (See, Example 1). In some embodiments, there is an increased secretion of exosomes from cells that are cultured under conditions of three-dimensional growth as compared with two-dimensional growth conditions.

In some embodiments, a method of large-scale production and purification of exosomes comprises a step of growing MSC-NTF cells in a high-density bioreactor system, or a step of three-dimensional growth of MSC-NTF cells, or a step of growing MSC-NTF cells in a high-density bioreactor system comprising three-dimensional growth of the cells.

In some embodiments, a method of large-scale production and purification of exosomes comprises a step of growing MSC in a high-density bioreactor system. In some embodiments, a method of large-scale production and purification of exosomes comprises a step of three-dimensional growth of MSC. In some embodiments, a method of large-scale production and purification of exosomes comprises a step of growing MSC in a high-density bioreactor system comprising three-dimensional growth of the cells.

In some embodiments, providing a cell sample for production and purification of exosomes comprises a step of growing the cells in a high-density bioreactor system. In some embodiments, providing the sample of cells comprises a step of three-dimensional growth of the cells. In some embodiments, providing a cell sample comprises a step of growing the cells in a high-density bioreactor system comprising three-dimensional growth of the cells. In some embodiments, the cell sample provided comprises differentiated MSC cells, or undifferentiated MSC cells, or genetically modified and differentiated MSC cells, or genetically modified undifferentiated MSCs.

In some embodiments, bioreactors are used to expand and propagate cells prior to the differentiation step. Bioreactors may be used for cultivation of cells, in which bioreactor conditions are suitable for high cell concentrations. In another embodiment, a bioreactor provides a closed system for expansion of cells. In another embodiment, multiple bioreactors are used in a series for cell expansion steps. In another embodiment, a bioreactor is used in methods of propagating genetically modified MSCs. In another embodiment, a bioreactor used in the methods disclosed herein is a single use bioreactor. In another embodiment, a bioreactor used is a multi-use bioreactor. In yet another embodiment, a bioreactor comprises a control unit for monitoring and controlling parameters of the process. In some embodiments, MSCs and/or genetically modified MSCs are expanded and propagated in a bioreactor. In some embodiments, MSC-NTF cells and/or genetically modified MSC-NTF cells are induced to differentiate in a bioreactor. In some embodiments, genetically modified MSCs are expanded and induced to differentiate into genetically modified MSC-NTFs.

In some embodiments, expansion and/or induction to differentiate is carried out in a bioreactor. Following isolation, the cells are typically expanded by culturing in a proliferation medium capable of maintaining and/or expanding the isolated cells ex vivo in the presence of, for example, platelet lysate. In some embodiments, the proliferation medium may include DMEM, alpha-MEM or DMEM/F12.

In one embodiment, when the MSCs are human, and the platelet lysate is also obtained from human cells. According to one embodiment, the medium is devoid of xeno contaminants i.e. is free of animal derived components. MSC isolation and propagation protocols are well known in the art, for example see Example 1 of International publication WO 2018/015945, which is incorporated herein in its entirety.

Verification that the isolated (and optionally propagated) cell population comprises MSCs may be performed by identification of phenotypic and functional criteria. The phenotypic criteria may include the expression of specific surface antigens: CD73, CD90 and CD105 (≥95% positive) and the absence (<2%) of at least one marker selected from the group including CD-3 (T-cells surface marker), CD14 (Monocyte surface marker), CD19 (B cells), CD34 (Hematopoietic stem cells), CD45 (Hematopoietic cells), CD5, CD11B, CD20, FMC7, and HLA-DR (Human Class II Histocompatibility antigen). In some embodiments, MSCs lack CD3, CD14, CD19, CD34, CD45, CD5, CD11B, CD20, FMC7, or HLA-DR, or any combination thereof. In some embodiments, MSC cells lack at least one of the markers CD3, CD14, CD19, CD34, CD45, CD5, CD11B, CD20, FMC7, or HLA-DR. In some embodiments, MSC cells lack at least two of the markers CD3, CD14, CD19, CD34, CD45, CD5, CD11B, CD20, FMC7, or HLA-DR. In some embodiments, MSC cells lack at least three of the markers CD3, CD14, CD19, CD34, CD45, CD5, CD11B, CD20, FMC7, or HLA-DR. In some embodiments, MSC cells lack at least four of the markers CD3, CD14, CD19, CD34, CD45, CD5, CD11B, CD20, FMC7, or HLA-DR. In some embodiments, MSC cells lack at least five of the markers CD3, CD14, CD19, CD34, CD45, CD5, CD11B, CD20, FMC7, or HLA-DR. In some embodiments, MSC cells lack at least six of the markers CD3, CD14, CD19, CD34, CD45, CD5, CD11B, CD20, FMC7, or HLA-DR. In some embodiments, MSC cells lack at least seven of the markers CD3, CD14, CD19, CD34, CD45, CD5, CD11B, CD20, FMC7, or HLA-DR. In some embodiments, MSC cells lack at least eight of the markers CD3, CD14, CD19, CD34, CD45, CD5, CD11B, CD20, FMC7, or HLA-DR. In some embodiments, MSC cells lack at least nine of the markers CD3, CD14, CD19, CD34, CD45, CD5, CD11B, CD20, FMC7, or HLA-DR. In some embodiments, MSC cells lack all of the markers CD3, CD14, CD19, CD34, CD45, CD5, CD11B, CD20, FMC7, or HLA-DR. In some embodiments, MSC cells lack 1-3 of the markers CD3, CD14, CD19, CD34, CD45, CD5, CD11B, CD20, FMC7, or HLA-DR. In some embodiments, MSC cells lack 1-4 of the markers CD3, CD14, CD19, CD34, CD45, CD5, CD11B, CD20, FMC7, or HLA-DR. In some embodiments, MSC cells lack 1-5 of the markers CD3, CD14, CD19, CD34, CD45, CD5, CD11B, CD20, FMC7, or HLA-DR. In some embodiments, MSC cells lack 2-4 of the markers CD3, CD14, CD19, CD34, CD45, CD5, CD11B, CD20, FMC7, or HLA-DR. In some embodiments, MSC cells lack 3-5 of the markers CD3, CD14, CD19, CD34, CD45, CD5, CD11B, CD20, FMC7, or HLA-DR. The surface expression of these cells may be analyzed using methods known in the art, for example by Flow Cytometry.

The phenotypes of MSC and MSC-NTF cells may in some embodiments, comprise similar morphological and/or component phenotypes. For example, the MSC-NTF cells described herein may show a morphology similar to that of MSCs (a spindle-like morphology). In some embodiments, MSC-NTFs comprise a morphology different from the source MSCs from which they were derived. Alternatively, or additionally the cells described herein may express a marker (e.g. surface marker) typical to MSCs but atypical to native astrocytic cells. Examples of MSC-NTF cell surface markers include but are not limited to CD105, CD29, CD44, CD90, CD73, CD271, and CD49. In some embodiments, MSC-NTF cells comprise at least one cell surface marker including but not limited to CD105, CD29, CD44, CD90, CD73, CD271, or CD49, or any combination thereof. In some embodiments, MSC-NTF cells lack a cell surface marker or markers selected from the group including CD34, CD45, CD19, CD5, CD20, CD11B, CD3, CD14, HLA-DR, or FMC7, or any combination thereof. In some embodiments, MSC lack a cell surface marker or markers selected from the group including CD34, CD45, CD19, CD5, CD20, CD11B, CD3, CD14, HLA-DR, or FMC7, or any combination thereof.

In some embodiments, MSC-NTFs comprise one or more membrane markers selected from the group comprising CD105, CD29, CD44, CD90, CD73, CD271, or CD49, or any combination thereof; and do not comprise at least one marker or a combination of markers selected from the group including CD34, CD45, CD19, CD5, CD20, CD11B, CD3, CD14, HLA-DR, and FMC7, or any combination thereof. In some embodiments, genetically modified MSCs retain MSC membrane markers. In some embodiments, genetically modified MSCs lack at least one cell surface marker or a combination of markers selected from the group including CD34, CD45, CD19, CD5, CD20, CD11B, CD3, CD14, HLA-DR, and FMC7, or any combination thereof.

Examples of antibodies that may be used to verify the presence or absence of MSCs include, for example, but not limited to, CD73 PE (Phycoerythrin) conjugated (BD Pharmingen), CD90 PE-Cy5 (a traditional far-red-fluorescent label for protein and nucleic acid conjugates used for imaging, flow cytometry, and genomic applications)_conjugated (eBioscience) CD105 PE conjugated (Beckman Coulter) CD14 FITC conjugated (eBioscience) CD19 PE-Cy5 conjugated (eBioscience) CD34 FITC conjugated (Beckman Coulter), CD45 PE conjugated (eBioscience) and HLA-DR PE-Cy5 conjugated (BD Pharmingen).

Another method for verifying the presence of MSCs is by showing that the cells are capable of differentiating into multi-lineages such as for example adipocytes, osteocytes and chondrocytes. This may be performed, for example, by using Human MSC Functional Identification Kit (R&D Systems).

As described herein, following propagation of MSCs in a platelet lysate containing medium, the cells may be differentiated in a differentiating medium for generating cells useful for treating a neurodegenerative disorder.

Differentiating media and their components are well known in the art. It will be appreciated that the components of the differentiating medium are selected according to the cell phenotype required.

In some embodiments, MSC-NTFs comprise one or more membrane markers selected from the group comprising CD105, CD29, CD44, CD90, CD73, CD271, or CD49, or any combination thereof; and do not comprise at least one of the markers or any combination thereof of markers selected from the group comprising CD34, CD45, CD19, CD5, CD20, CD11B, CD3, CD14, HLA-DR, and FMC7. Exosomes isolated from differentiated MSCs would thus be expected to comprise one or more membrane markers selected from the group comprising CD105, CD29, CD44, CD90, CD73, CD271, or CD49, or any combination thereof; and do not comprise at least one of the markers or any combination thereof of markers selected from the group comprising CD34, CD45, CD19, CD5, CD20, CD11B, CD3, CD14, HLA-DR, calnexin, and FMC7.

In some embodiments, MSCs are induced to secrete at least one neurotrophic factor (NTF), wherein said cell population is demoted "MSC-NTF cells" or "MSC-NTFs".

As used herein, the term "neurotrophic factor" ("NTF") refers to a cell-secreted factor that acts on the central nervous system comprising growth, differentiation, functional maintenance and/or survival effects on neurons. Examples of neurotrophic factors include, for example, but are not limited to, a vascular endothelial growth factor (VEGF), a hepatocyte growth factor (HGF), a leukemia inhibitory factor (LIF), a glial derived neurotrophic factor (GDNF), a neurotrophin-3 (NT-3), a neurotrophin-4/5, a Neurturin (NTN), a Neurotrophin-4, a Persephin, artemin (ART), a ciliary neurotrophic factor (CNTF), an insulin growth factor-I (IGF-1), Growth and differentiation Factor (GDF-15), Granulocyte Stimulating factor (G-CSF), a Brain-derived neurotrophic factor (BDNF), a Tumor necrosis factor-inducible gene 6 protein (TSG-6; also known as TNF-stimulated gene 6 protein), Bone morphogenetic protein 2 (BMP2), and Fibroblast Growth Factor 2 (FGF2).

A skilled artisan would appreciate that the terms "protein" and "polypeptide" may be used interchangeably herein having all the same meanings and qualities. In some embodiments, "polypeptide" or "protein" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides even more stable while in a body or more capable of penetrating into cells. In some embodiments, proteins are not limited to a minimum length unless otherwise defined or indicated. In some embodiments, a protein comprises a peptide, for example naturally occurring peptides present in a cell that may themselves be a target of a neurodegenerative disease.

In one embodiment, an NTF is selected from the group comprising a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and (FGF2, or any combination thereof.

In another embodiment, an NTF is a VEGF. In another embodiment, an NTF is a HGF. In another embodiment, an NTF is a LIF. In another embodiment, an NTF is a GDNF. In another embodiment, an NTF is a NT-3. In another embodiment, an NTF is a neurotrophin-4/5. In another embodiment, an NTF is a NTN. In another embodiment, an NTF is a Neurotrophin-4. In another embodiment, an NTF is a Persephin, or an ART. In another embodiment, an NTF is a CNTF. In another embodiment, an NTF is an IGF-1. In another embodiment, an NTF is GDF-15. In another embodiment, an NTF is a G-CSF. In another embodiment, an NTF is a BDNF. In another embodiment, an NTF is a TSG-6. In another embodiment, an NTF is a BMP2. In another embodiment, an NTF is a FGF2.

In another embodiment, a MSC-NTF cell secretes at least one NTF, wherein said NTF is selected from the group comprising a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and (FGF2, or any combination thereof.

In another embodiment, an MSC-NTF cell secretes a VEGF. In another embodiment, an MSC-NTF cell secretes a HGF. In another embodiment, an MSC-NTF secretes a LIF. In another embodiment, an MSC-NTF cell secretes a GDNF. In another embodiment, an MSC-NTF cell secretes a NT-3. In another embodiment, an MSC-NTF cell secretes a neurotrophin-4/5. In another embodiment, an MSC-NTF cell secretes a NTN. In another embodiment, an MSC-NTF cell secretes a Neurotrophin-4. In another embodiment, an MSC-NTF cell secretes a Persephin. In another embodiment, an MSC-NTF cell secretes an ART. In another embodiment, an MSC-NTF cell secretes a CNTF. In another embodiment, an MSC-NTF cell secretes an IGF-1. In another embodiment, an MSC-NTF cell secretes a GDF-15. In another embodiment, an MSC-NTF cell secretes a G-CSF. In another embodiment, an MSC-NTF cell secretes a BDNF. In another embodiment, an MSC-NTF cell secretes a TSG-6. In another embodiment, an MSC-NTF cell secretes a BMP2. In another embodiment, an MSC-NTF cell secretes a FGF2.

In another embodiment, an MSC-NTF cell secretes at least 2 NTFs. In another embodiment, an MSC-NTF cell secretes at least 3 NTFs. In another embodiment, an MSC-NTF cell secretes at least 4 NTFs. In another embodiment, an MSC-NTF cell secretes at least 5 NTFs.

Neurotrophic factors-secreting human mesenchymal stromal stem cells are well known in the art and fully described in PCT International Patent Application Publication Nos. WO 2014/024183 and WO 2015/121859; Gothelf et al., 2014, Clin Transl Med., 3:21; Petrou et al. 2014; Muscle & Nerve. 49(3):455-457 and Petrou et al., 2016, JAMA Neurol. 73(3):337-44; all of which are incorporated by reference herein in their entirety.

In one embodiment, MSC-NTF cells described herein secrete at least one NTF selected from the group comprising a vascular endothelial growth factor (VEGF), a hepatocyte growth factor (HGF), a leukemia inhibitory factor (LIF), a Brain-derived neurotrophic factor (BDNF), a Tumor necrosis factor-inducible gene 6 protein (TSG-6; also known as TNF-stimulated gene 6 protein), Bone morphogenetic protein 2 (BMP2), Fibroblast Growth Factor 2 (FGF2), or Granulocyte Stimulating factor (G-CSF), or any combination thereof.

In another embodiment, MSC-NTF cells described herein secrete NTF selected from the group comprising a vascular endothelial growth factor (VEGF), a hepatocyte growth factor, and a leukemia inhibitory factor (LIF). In another embodiment, MSC-NTF cells described herein secrete NTF selected from the group consisting of a vascular endothelial growth factor (VEGF), a hepatocyte growth factor, a leukemia inhibitory factor (LIF), a Brain-derived neurotrophic factor (BDNF), a Tumor necrosis factor-inducible gene 6 protein (TSG-6; also known as TNF-stimulated gene 6 protein), Bone morphogenetic protein 2 (BMP2), Fibroblast Growth Factor 2 (FGF2), and Granulocyte Stimulating factor (G-CSF).

In some embodiments, at least 50%, at least 60%, at least 70%, at least 80%, at least 90% or more of a population of the MSC-NTF cells described herein express at least one NTF. In some embodiments, at least 50%, at least 60%, at least 70%, at least 80%, at least 90% or more of a population of the MSC-NTF cells described herein secrete at least one NTF. In some embodiments, exosomes isolated from MSC-NTF cells comprise at least one of the NTFs secreted by MSC-NTF cells.

In some embodiments, MSC-NTF cells described herein, express at least one miRNA molecule. In some embodiments, MSC-NTF cells described herein, express and secrete at least one miRNA molecule. In some embodiments, miRNA describe herein are present in a biological sample. Human MSC-NTF cells secreting specific Micro-RNAs are well known in the art and fully described in Gothelf et al., (2017) Stem Cell Research & Therapy 8:249.

In certain embodiments, a control MSC cell is a non-differentiated MSC. In certain embodiments, a control MSC cell does not secrete increased amounts of an NTF.

In some embodiments, expression of an at least one miRNA molecule in MSC-NTF cells is greater than that observed in control MSCs. In some embodiments, the level of an at least one miRNA molecule in a biological sample from a subject administered with MSC-NTFs, for example a CSF biological sample, is greater than that observed in an equivalent control biological sample. In some embodiments, the level of an at least one miRNA molecule in a biological sample from a subject administered with MSC-NTFs, for example a urine biological sample, is greater than that observed in an equivalent control biological sample. In some embodiments, the level of an at least one miRNA molecule in a biological sample from a subject administered with MSC-NTFs, for example a blood biological sample, is greater than that observed in an equivalent control biological sample. In some embodiments, the level of an at least one miRNA molecule in a biological sample from a subject administered with MSC-NTFs, for example a blood serum biological sample, is greater than that observed in an equivalent control biological sample. In some embodiments, miRNAs may be excreted from MSC-NTF cells, for example by way of an exosome. In some embodiments, the expression and/or secretion of an at least one miRNA molecule from MSC-NTF cells is greater than that observed in control MSCs. In some embodiments, exosomes isolated from MSC-NTF cells comprise one or more of the miRNA molecules expressed in MSC-NTF cells.

In some embodiments, MSC-NTF cells described herein have reduced or no expression of at least one miRNA, compared with control MSCs. In some embodiments, MSC-NTF cells described herein have reduced or no secretion of at least one miRNA, compared with control MSCs. In some embodiments, MSC-NTF cells described herein have reduced or no expression or secretion of at least one miRNA, compared with control MSCs.

In some embodiments, MSC-NTF cells described herein, are able to induce expression of at least one miRNA molecule in another cell. In some embodiments, MSC-NTF cells described herein, are able to induce expression of at least one miRNA molecule in another cell. Cell-to-cell communication in which a cell produces a signal to induce changes in nearby cells, altering the behavior of those cells, may, in some embodiments, be referred to as a "paracrine response".

A skilled artisan would appreciate that the terms "miRNA", "miR", and "micro RNA" may be used interchangeably having all the same meanings and qualities and encompass short non-coding RNAs. In some embodiments, miRNAs comprise about 21-25 nucleotides. In some embodiments, miRNAs comprise about 21-24 nucleotides. In some embodiments, miRNAs comprise 21, 22, 23, 24, or 25 nucleotides. In some embodiments, miRNAs may play an important role in the regulation of cellular gene expression by either suppressing translation of protein coding genes or by cleaving target mRNA to induce their degradation. In some embodiments, miRNAs may serve as paracrine signaling mediators. In some embodiments, miRNAs may be increased or decreased in MSC-NTF cells.

Examples of miRNAs that may be increased in MSC-NTF cells compared to non-differentiated MSCs include, for example, but are not limited to miR-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, or miR-4324, or any combination thereof. Examples of miRNAs that may be decreased in MSC-NTF cells compared to non-differentiated MSCs include, for example, but are not limited to miR-503, miR-3659, miR-3529-3p, miR-320b, miR-1275, miR-3132, miR-320a, miR-495, miR-181b-5p, miR-222-3p, miR-424-5p, miR-4284, miR-574-5p, miR-143-3p, miR-106a-5p, miR-455-3p, miR-20a-5p, miR-145-5p, miR-324-3p, miR-130b-3p, miR-1305, or miR-140-3p, or any combination thereof.

In some embodiments, MSC-NTF cells described herein express at least one miRNAs selected from the group comprising miR-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, or miR-4324, miR-503, miR-3659, miR-3529-3p, miR-320b, miR-1275, miR-3132, miR-320a, miR-495, miR-181b-5p, miR-222-3p, miR-424-5p, miR-4284, miR-574-5p, miR-143-3p, miR-106a-5p, miR-455-3p, miR-20a-5p, miR-145-5p, miR-324-3p, miR-130b-3p, miR-1305, or miR-140-3p or any combination thereof, wherein said expression is either increased or decreased compared with non-differentiated MSCs.

In some embodiments, MSC-NTFs are genetically modified to express an miRNA in an effort to increase the amount of that miRNA in exosomes isolated from said MSC-NTF. In some embodiments, the MSCs may be genetically modified to express an miRNA. In some embodiments, the MSC-NTFs are genetically modified to express an miRNA. In some embodiments, the miRNA is miR-7.

In some embodiments, MSCs are genetically modified to express an miRNA in an effort to increase the amount of that miRNA in exosomes isolated from said MSCs. In some embodiments, the miRNA is miR-7.

In some embodiments, miRNA expression in genetically-modified MSCs is elevated compared to non-genetically modified MSCs.

In some embodiments, exosomes isolated from genetically-modified MSC cells comprise an increased amount of an miRNA compared with exosomes isolated from non-genetically modified MSCs.

In some embodiments, miRNA expression in MSC-NTF cells is elevated compared to non-differentiated MSCs. In some embodiments, miRNA expression in MSC-NTF cells is reduced compared to non-differentiated MSCs. In some embodiments, miRNA expression in MSC-NTF cells is absent compared to non-differentiated MSCs.

In some embodiments, exosomes isolated from MSC-NTF cells comprise an increased amount of an miRNA compared with exosomes isolated from non-differentiated MSCs. In other embodiments, exosomes isolated from MSC-NTF cells comprise a decreased amount of an miRNA compared with exosomes isolated from non-differentiated MSCs.

In some embodiments, an MSC-NTF cell or exosome comprises an increased amount of an miR-3663-3p. In some embodiments, an MSC-NTF cell or exosome comprises an increased amount of an miR-132-3p. In some embodiments, an MSC-NTF cell or exosome comprises an increased amount of an miR-150-3p. In some embodiments, an MSC-NTF cell or exosome comprises an increased amount of an miR-762. In some embodiments, an MSC-NTF cell or exosome comprises an increased amount of an miR-4327. In some embodiments, an MSC-NTF cell or exosome comprises an increased amount of an miR-3665. In some embodiments, an MSC-NTF cell or exosome comprises an increased amount of an miR-34a-5p. In some embodiments, an MSC-NTF cell or exosome comprises an increased amount of an miR-1915. In some embodiments, an MSC-NTF cell or exosome comprises an increased amount of an miR-34a-39. In some embodiments, an MSC-NTF cell or exosome comprises an increased amount of an miR-34b-5p. In some embodiments, an MSC-NTF cell or exosome comprises an increased amount of an miR-874. In some embodiments, an MSC-NTF cell or exosome comprises an increased amount of an miR-4281. In some embodiments, an MSC-NTF cell or exosome comprises an increased amount of an miR-1207-5p. In some embodiments, an MSC-NTF cell or exosome comprises an increased amount of an miR-30b-5p. In some embodiments, an MSC-NTF cell or exosome comprises an increased amount of an miR-29b-3p. In some embodiments, an MSC-NTF cell or exosome comprises an increased amount of an miR-199b-5p. In some embodiments, an MSC-NTF cell or exosome comprises an increased amount of an miR-30e-5p. In some embodiments, an MSC-NTF comprises an increased amount of an miR-26a-5p. In some embodiments, an MSC-NTF cell or exosome comprises an increased amount of an miR-4324.

In some embodiments, MSC-NTF cells do not express or have low expression of at least one miRNA compared with non-differentiated MSCs. In some embodiments, MSC-NTFs comprise a decreased amount of an at least one miRNA molecule compared with a non-differentiated MSCs, wherein said at least one miRNA molecule is selected from the group comprising miR-503, miR-3659, miR-3529-3p, miR-320b, miR-1275, miR-3132, miR-320a, miR-495, miR-181b-5p, miR-222-3p, miR-424-5p, miR-4284, miR-574-5p, miR-143-3p, miR-106a-5p, miR-455-3p, miR-20a-5p, miR-145-5p, miR-324-3p, miR-130b-3p, miR-1305, or miR-140-3p, or any combination thereof. In some embodiments, MSC-NTF cells do not express or have low expression of miR-503. In some embodiments, MSC-NTF cells do not express or have low expression of miR-3659. In some embodiments, MSC-NTF cells do not express or have low expression of miR-3529-3p. In some embodiments, MSC-NTF cells do not express or have low expression of miR-320b. In some embodiments, MSC-NTF cells do not express or have low expression of miR-1275. In some embodiments, MSC-NTF cells do not express or have low expression of miR-3132. In some embodiments, MSC-NTF cells do not express or have low expression of miR-320a. In some embodiments, MSC-NTF cells do not express or have low expression of miR-495. In some embodiments, MSC-NTF cells do not express or have low expression of miR-181b-5p. In some embodiments, MSC-NTF cells do not express or have low expression of miR-222-3p. In some embodiments, MSC-NTF cells do not express or have low expression of miR-424-5p. In some embodiments, MSC-NTF cells do not express or have low expression of miR-4284. In some embodiments, MSC-NTF cells do not express or have low expression of miR-574-5p. In some embodiments, MSC-NTF cells do not express or have low expression of miR-143-3p. In some embodiments, MSC-NTF cells do not express or have low expression of miR-106a-5p. In some embodiments, MSC-NTF cells do not express or have low expression of miR-455-3p. In some embodiments, MSC-NTF cells do not express or have low expression of miR-20a-5p. In some embodiments, MSC-NTF cells do not express or have low expression of miR-145-5p. In some embodiments, MSC-NTF cells do not express or have low expression of miR-324-3p. In some embodiments, MSC-NTF cells do not express or have low expression of miR-130b-3p. In some embodiments, MSC-NTF cells do not express or have low expression of miR-1305. In some embodiments, MSC-NTF cells do not express or have low expression of miR-140-3p.

In some embodiments, miRNAs are globally down-regulated in motor neurons of ALS patients.

In one embodiment, MSC-NTF cells are ex-vivo differentiated from MSCs, expressing at least one MSC marker. In some embodiments, differentiation does not comprise genetic modification. In some embodiments, the MSCs described herein are not genetically manipulated (i.e. transformed with an expression construct) to generate the differentiated cells and cell populations described herein.

In another embodiment, an isolated human cell comprising a MSC-NTF cell comprising at least one MSC phenotype and secreting at least one NTF, for example VEGF, GDNF, LIF, G-CSF, BDNF, TGS-6, BMP2, FGF2, or HGF, or any combination thereof comprises a basal secretion of the NTF that is greater than a basal secretion of the NTF in a non-differentiated MSC (a control MSC).

In some embodiments, MSC-NTF cells induce an increase in a specific neurotrophic factor and a reduction in inflammatory biomarkers in the CSF of a treated ALS patient, in contrast to placebo. See for example International Publication No. WO 2018/015945 at Example 2, which is incorporated herein in its entirety.

In some embodiments, a biomarker expressed from MSC-NTF cells comprises any one of TOP2A, RAB27b, WNT5A, SNAP25, AREG, SLC1A1, SLC16A6, MEST, SLC1A3, PCSK1, or TUBB3, or any combination thereof. In some embodiments, MSC-NTF cells comprise decreased expression of any one of topoisomerase 2-alpha (TOP2A), fibroblast growth factor 2 (FGF2), mesoderm-specific transcript homolog (MEST), solute carrier family 1 member 1 (SLC1A1), or beta-III-tubulin (TUBB3), or any combination thereof. In some embodiments, MSC-NTF cells comprise increased expression of any one of bone morphogenetic protein 2 (BMP2), leukemia inhibitory factor (LIF), Wnt family member 5A (WNT5A), amphiregulin (AREG), hepatocyte growth factor (HGF), brain-derived neurotrophic factor (BDNF), proprotein convertase 1 (PCSK1), ras in the brain (RAB)27B, synaptosomal-associated protein 25 (SNAP25), solute carrier family 1 member 3 (SLC1A3), or solute carrier family 16, member 6 (SLC16A6), or any combination thereof.

In some embodiments, the MSCs described herein are genetically manipulated (i.e. transformed with an expression construct). Genetic modification of MSC cells prior to or following ex-vivo differentiation, may be used to increase the amount of a molecule whose presence is desired in exosomes isolated from the MSC or the differentiated MSC-NTF. In some embodiments, the molecule is beneficial in the treatment of neurodegenerative diseases. In some embodiments, the desired molecule is a growth factor. In some embodiments, the desired molecule is a galectin-1 molecule. In some embodiments, the desired molecule is an siRNA or an miRNA. In some embodiments, a growth factor comprises a growth differentiation factor (GDF) 5. In some embodiments, a growth factor comprises an insulin-like growth factor (IGF)-1. In some embodiments, a growth factor comprises an insulin-like growth factor (IGF)-2. In some embodiments a growth factor is a human growth factor. In some embodiments a galectin-1 molecule is a human galectin-1 molecule. In some embodiments, an siRNA encodes a nucleotide sequence complementary to MMP9 or a portion thereof. In some embodiments, a miRNA comprises a miR-7. In some embodiments, the desired molecule is any combination of a growth factor, an miRNA, and a siRNA.

In some embodiments, MSCs are transformed with a vector encoding the protein or polypeptide of interest operably linked to a promoter or to a promoter/enhancer combination. In some embodiments, the vector further comprises a selection marker gene operably linked to the promoter or promoter/enhancer combination. In some embodiments, the promoter is a constitutive promoter. In some embodiments, the promoter is selected from the group comprising pCAG, EFIOC, PGK, CMV and SFFV. In some embodiments, the vector further comprises pro-viral sequences.

A skilled artisan would appreciate that a transgene cassette comprising polynucleotides encoding the protein or polypeptide of interest can be integrated into various viral and non-viral vector systems for delivery and stable expression in MSCs.

In some embodiments, MSCs are genetically modified by viral transfection methods, or viral transduction. In some embodiments, a viral vector is derived from the group comprising alpha-retroviruses, gamma-retroviruses, (human and non-human) lentiviruses, and adenoviruses. In some embodiments, retroviral vector systems include the transfer vector backbone, which carries the transgene of interest, i.e. the protein or polypeptide encoding region, and all sequence elements necessary for the reverse transcription and integration of the vector DNA, but is devoid of most or all viral genes, such as gag- pol- and env-genes. In some embodiments, retroviral vectors carry special safety modifications, as self-inactivating (SIN) vectors, in which the 3' LTR-region is partially or completely removed to shut down viral promoter activity and to prevent transactivation of neighboring genes in the host cell genome.

For the production of viral particles, a variable number of helper plasmids is needed which provide the structural proteins, enzyme and envelope proteins in trans. Viral particles can be produced carrying foreign envelope glycoproteins. This process is called pseudo-typing, and it allows altering the tropism of the vector particles and, in some cases, enhances vector titer.

In some embodiments, genetic modification of MSCs is accomplished by using a non-viral vector system. In some embodiments, a non-viral vector system comprises plasmid transfer, phage integrases, and transposons.

In some embodiments, MSCs are genetically modified by chemical transfection methods. In some embodiments, a chemical transfection method is selected from the group comprising: lipofection, methods comprising use of cationic polymers, methods comprising use highly branched organic compounds, methods comprising use of calcium phosphate, and methods comprising use of Fugene non-liposomal reagents.

In some embodiments, MSCs are genetically modified by physical transfection methods. In some embodiments, a physical transfection method is selected from the group comprising: electroporation, cell squeezing, sonoroporation, optical transfection, protoplast fusion, impalefection, and hydrodynamic delivery.

In some embodiments, MSCs are genetically modified by particle-based transfection methods. In some embodiments, a particle-based transfection method is selected from the group comprising: a gene gun method, magnet-assisted transfection, and impalefection.

In some embodiments, MSCs are stably transfected, i.e. the transfected vector is integrated into the MSC genome. A skilled artisan would appreciate that integration of the transfected vector into the cell genome enables the production of genetically modified mesenchymal stems cells, which are more stable than genetically modified stem cells harboring an extra-chromosomal vector.

A skilled artisan would appreciate that following transfection, stably transfected cells can be selected by methods known in the art. In some embodiments, MSCs can further comprise a selection marker gene operably linked to a constitutive promoter or promoter/enhancer combination. The selection marker gene can comprise an antibiotic resistance gene, such as a gene conferring resistance to Puromycin, Neomycin or Ouabain. The antibiotic resistance genes can be used in order to select for genetically modified MSCs under the presence of the antibiotic. In addition, or as an alternative to, an antibiotic resistance gene, a gene encoding a surface marker protein can be used, which is only expressed on the surface of genetically modified MSCs. Magnetic beads harboring specific antibodies recognizing the surface marker proteins can be used in order to select for the genetically modified MSCs.

In some embodiments, a genetically modified MSC cell or a genetically modified MSC-NTF cell expresses a beneficial molecule of interest. In some embodiments, the beneficial molecule of interest is a protein or polypeptide. In some embodiments, the protein or polypeptide of interest comprises a neurotrophic factor. In some embodiments, the protein or polypeptide of interest comprises IGF-1. In some embodiments, the protein or polypeptide of interest comprises IGF-2. In some embodiments, the protein or polypeptide of interest comprises GDF-5. In some embodiments, the protein or polypeptide of interest comprises galectin-1. In some embodiments, the expression vector comprises a miRNA sequence. In some embodiments, the expression vector comprises a miRNA-7 sequence. In some embodiments, the expression vector comprises a siRNA sequence. In some embodiments, the expression vector comprises a MMP-9 siRNA sequence or a portion thereof.

MSC & MSC-NTF Derived Exosomes

Exosomes are nano-sized, secreted cell vesicles (extracellular vesicles). These vesicles are formed by inward budding of late endosomes and are then released to the extracellular environment upon fusion with the plasma membrane. Because exosomes naturally comprise and transfer RNA between cells, this property may be useful in gene therapy. In some embodiments, MSC-NTF-isolated exosomes may be used to transfer an RNA molecule to a cell, for example, an siRNA or an miRNA molecule. In some embodiments, modified MSC exosomes, isolated from genetically modified MSCs may be used to transfer an RNA molecule to a cell. For example, an siRNA or an miRNA molecule that is expressed or over expressed or highly expressed in the genetically modified MSCs. In some embodiments, an exosome isolated from a MSC cell may be used to transfer an RNA molecule to a cell by first modifying the MSC-derived exosome to comprise the RNA molecule, for example an siRNA or an miRNA.

A skilled artisan would appreciate that the terms "exosome" and "exosomes" as used throughout this disclosure may be used interchangeably having all the same meanings and qualities. Thus, in some embodiments, the term exosome comprises many exosomes as in describing the exosome yield was $4 \times 10^{11}$ purified exosomes versus about $7 \times 10^{10}$ purified exosomes (See, Example 1) or when describing the use of an exosome in the methods disclosed herein.

In some embodiments, isolated exosomes derived from MSC-NTF cells are termed an isolated exosome population. A skilled artisan would appreciate that the terms "isolated MSC-NTF derived exosomes", "isolated MSC-NTF cell derived exosomes", "isolated MSC-NTF derived exosome population", "isolated MSC-NTF cell derived exosome population", "isolated MSC-NTF exosomes", "isolated MSC-NTF cell exosomes", "isolated MSC-NTF exosome population", and "isolated MSC-NTF cell exosome population" may be used herein interchangeably, having all the same qualities and meanings. In the context of a description, in some embodiments, isolated MSC-NTF derived exosomes are termed "isolated exosomes". This is in contrast to exosomes isolated from control MSC cells, which in some embodiments are termed control exosomes.

The content of exosomes isolated from MSCs is not constant, but rather a product of the MSCs' tissue origin, its activities and the immediate intercellular neighbors of the MSCs. In some embodiments, the content of exosomes may be the product of genetic modification of the MSCs. MSC-derived exosomes may have a content that includes cytokines and growth factors, signaling lipids, mRNAs, and regulatory miRNAs. Further, the effects of MSCs delivered to patients and showing therapeutic benefit, may be exosome-derived because exosomes purified from MSCs may promote similar effects to MSC-based treatments.

Similarly, exosomes derived from the differentiated MSCs described herein, for example exosomes isolated from MSC-NTFs, may, in certain embodiments, comprise the same or similar content to that of the MSC-NTF cells or genetically modified MSC-NTFs. Further, delivery to patients of MSC-NTF-derived exosomes, may, in some embodiments provide the same therapeutic benefit while advantageously be able to cross the blood brain barrier, be stable, have the ability to be loaded with further beneficial factors, and have low immunogenicity.

In some embodiments, exosomes disclosed herein are between 30-300 nm in size, e.g. in diameter. In some embodiments, exosomes disclosed herein are between 30-250 nm. In some embodiments, exosomes disclosed herein are between 30-200 nm. In some embodiments, exosomes disclosed herein are between 30-175 nm. In some embodiments, exosomes disclosed herein are between 30-150 nm. In some embodiments, exosomes disclosed herein are between 40-150 nm. In some embodiments, exosomes disclosed herein are between 50-150 nm. In some embodiments, exosomes disclosed herein are between 30-100 nm. In some embodiments, exosomes disclosed herein are between 100-150 nm. In certain embodiments, the median size of a population of exosomes is about 116 nm to about 148 nm132 nm. In certain embodiments, the median size of a population of exosomes is about 132 nm. In certain embodiments, the mean size of a population of exosomes is about 117 nm to about 147 nm. In certain embodiments, the mean size of a population of exosomes is about 132 nm.

In some embodiments, disclosed herein are isolated cell-type specific exosomes, wherein said cell-type comprises differentiated MSCs (MSC) that have been induced to secrete at least one neurotrophic factor (NTF), termed MSC-NTF cells, and wherein the basal secretion of said at least one NTF is greater in said MSC-NTFs compared with the basal secretion of said at least one NTF in a non-differentiated MSCs. MSC-NTF cells have been described above in detail.

In some embodiments, an MSC-NTF cell derived exosome population comprises at least 1 NTF secreted by the MSC-NTF cell, as cargo. In some embodiments, an MSC-NTF cell derived exosome population comprises at least 2 NTFs secreted by the MSC-NTF cell, as cargo. In some embodiments, an MSC-NTF cell derived exosome population comprises at least 3 NTFs secreted by the MSC-NTF cell, as cargo. In some embodiments, an MSC-NTF cell derived exosome population comprises at least 4 NTFs secreted by the MSC-NTF cell, as cargo. In some embodiments, an MSC-NTF cell derived exosome population comprises at least 5, 6, 7, 8, 9, 10 NTFs secreted by the MSC-NTF cell, as cargo.

In some embodiments, an MSC-NTF cell derived exosome population comprises an increased quantity of at least 1 NTF as cargo, compared with exosomes isolated from control MSC. In some embodiments, an MSC-NTF cell derived exosome population comprises an increased quantity of at least 2 NTF as cargo, compared with exosomes isolated from control MSC. In some embodiments, an MSC-NTF cell derived exosome population comprises an increased quantity of at least 3 NTF as cargo, compared with exosomes isolated from control MSC. In some embodiments, an MSC-NTF cell derived exosome population comprises an increased quantity of at least 4 NTF as cargo, compared with exosomes isolated from control MSC. In some embodiments, an MSC-NTF cell derived exosome population comprises an increased quantity of at least 5, 6, 7, 8, 9, or 10 NTF as cargo, compared with exosomes isolated from control MSC.

In some embodiments, an MSC-NTF cell derived exosome population comprises an increased quantity of a LIF protein as cargo, compared with exosomes isolated from control MSC. In some embodiments, an MSC-NTF cell derived exosome population comprises an increased quantity of a GDF15 protein as cargo, compared with exosomes isolated from control MSC. In some embodiments, an MSC-NTF cell derived exosome population comprises an increased quantity of a VEGF or VEGFA protein as cargo, compared with exosomes isolated from control MSC. In some embodiments, an MSC-NTF cell derived exosome population comprises an increased quantity of a LIF protein, or a GDF15 protein, or a VEGF or VEGFA protein as cargo, compared with exosomes isolated from control MSC. In some embodiments, an MSC-NTF cell derived exosome population comprises an increased quantity of a LIF protein, and a GDF15 protein, and a VEGF or VEGFA protein as cargo, compared with exosomes isolated from control MSC. In some embodiments, an MSC-NTF cell derived exosome population comprises an increased quantity of a combination of any of a LIF protein, or a GDF15 protein, or a VEGF or VEGFA protein as cargo, compared with exosomes isolated from control MSC.

In some embodiments, exosomes isolated from MSC-NTF cells comprise an increased quantity of NTF compared to exosomes isolated from MSC control cells. For example, but not limited to, in some embodiments, exosomes isolated from MSC-NTF cells comprise an increased quantity of an NTF selected from VEGF, HGF, LIF, GDNF, NT-3, neurotrophin-4/5, NTN, Neurotrophin-4, a Persephin, ART, CNTF, IGF-1, GDF-15, G-CSF, BDNF, TSG-6, BMP2, and FGF2, or any combination thereof.

In some embodiments, disclosed herein are isolated cell-type specific exosomes, wherein said cell-type comprises MSCs or genetically modified MSCs.

In some embodiments, MSC-NTF exosomes comprise a portion of the content or membrane markers of MSC-NTF. In some embodiments, MSC-NTF exosomes comprise endosomal markers including, but not limited to, CD9, CD61, CD81, ALIX, or TSG101, or any combination thereof. It is noted that ALIX may also be known as Programmed Cell Death 6 Interacting Protein (PDCD6IP). In some embodiments, MSC-NTF exosomes comprise membrane markers of MSC-NTFs and specific exosome markers. In some embodiments, isolated exosome comprises one or more membrane markers selected from the group comprising cluster of differentiation (CD)9, CD63, CD44, CD73, CD90, CD105, CD9, CD61, CD81, ALIX, or tumor susceptibility gene (TSG)101, or any combination thereof.

In some embodiments, MSC exosomes comprise a portion of the content or membrane markers of MSCs. In some embodiments, MSC exosomes comprise endosomal markers including but not limited to CD9, CD61, CD81, ALIX, or TSG101, or any combination thereof. It is noted that ALIX may also be known as Programmed Cell Death 6 Interacting Protein (PDCD6IP). In some embodiments, MSC exosomes comprise membrane markers of MSCs and specific exosome markers. In some embodiments, isolated exosome comprises one or more membrane markers selected from the group comprising cluster of differentiation (CD)9, CD63, CD44, CD73, CD90, CD105, CD61, CD81, ALIX, or tumor susceptibility gene (TSG)101, or any combination thereof.

Calnexin is an integral membrane protein of the endoplasmic reticulum and would not be expected to be present within the exosome membrane. Similarly, membrane markers not present in MSCs or MSC-NTFs would not be expected to be present within the exosome membrane. In some embodiments, isolated MSC or MSC-NTF exosomes do not comprise at least one marker selected from the group including CD34, CD45, CD19, CD5, CD20, CD11B, CD3, CD14, HLA-DR, calnexin, and FMC7. In some embodiments, isolated MSC or MSC-NTF exosomes do not comprise any combination of markers selected from the group including CD34, CD45, CD19, CD5, CD20, CD11B, CD3, CD14, HLA-DR, calnexin, and FMC7.

In some embodiments, isolated MSC-NTF exosomes comprise one or more membrane markers selected from the group comprising cluster of differentiation (CD)9, CD63, CD44, CD73, CD90, CD105, CD61, CD81, ALIX, or tumor susceptibility gene (TSG)101, or any combination thereof; and does not comprise at least one marker selected from the group including CD34, CD45, CD19, CD5, CD20, CD11B, CD3, CD14, HLA-DR, calnexin, and FMC7. In some embodiments, isolated MSC-NTF exosomes do not comprise any combination of markers selected from the group including CD34, CD45, CD19, CD5, CD20, CD11B, CD3, CD14, HLA-DR, calnexin, and FMC7.

In some embodiments, isolated MSC exosomes comprise one or more membrane markers selected from the group comprising cluster of differentiation (CD)9, CD63, CD44, CD73, CD90, CD105, CD61, CD81, ALIX, or tumor susceptibility gene (TSG)101, or any combination thereof; and does not comprise one or more markers selected from the group including CD34, CD45, CD19, CD5, CD20, CD11B, CD3, CD14, HLA-DR, calnexin, and FMC7, or any combination thereof.

Similar to the pattern of markers, membrane and otherwise, found in MSC exosome populations, the content of exosome populations may, in some embodiments, mirror that of the MSCs from which they were isolated.

Similar to the pattern of markers, membrane and otherwise, found in MSC-NTF exosomes, the content of exosome populations may, in some embodiments, mirror that of the MSC-NTF cells from which they were isolated. In some embodiments, an isolated exosome comprises an increased amount of said at least one NTF that is increased in MSC-NTFs compared with an exosome isolated from non-differentiated MSCs. Neurotrophic factors (NTF) that in some embodiments are increased in MSC-NTF exosomes comprise a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and (FGF2, or any combination thereof. In some embodiments, an MSC-NTF exosome comprises VEGF. In some embodiments, an MSC-NTF exosome comprises an HGF. In some embodiments, an MSC-NTF exosome comprises a LIF. In some embodiments, an MSC-NTF exosome comprises a G-CSF. In some embodiments, an MSC-NTF exosome comprises a BDNF. In some embodiments, an MSC-NTF exosome comprises a TSG-6; also known as TNF-stimulated gene 6 protein. In some embodiments, an MSC-NTF exosome comprises a BMP2. In some embodiments, an MSC-NTF exosome comprises a FGF2.

In some embodiments, an isolated exosome population derived from MSC-NTF cells comprises an increased amount of any of VEGF, HGF, LIF, G-CSF, BDNF, TSG-6, BMP2, and FGF2, compared with exosomes isolated from control MSC. In some embodiments, additional cargo may be comprised within MSC-NTF derived exosomes. (See for example, Table 1 of Example 4).

In some embodiments, an isolated exosome comprises an increased amount of said at least one miRNA that is increased in MSC-NTFs compared with an exosome isolated from non-differentiated MSCs. In some embodiments, isolated exosome comprises a decreased amount of at least one miRNA that is decreased in MSC-NTFs compared with an exosome isolated from non-differentiated MSC.

In some embodiments, an isolated exosome comprises an increased amount of said at least one miRNA that is increased in a genetically-modified MSC cell compared with an exosome isolated from non-genetically modified MSC cell.

In some embodiments, an isolated MSC-NTF exosome comprises an increased amount of at least one micro-RNA (miRNA) molecule compared with an exosome isolated from non-differentiated MSCs. In some embodiments, an isolated MSC-NTF exosome comprises an increased amount of at least one micro-RNA (miRNA) molecule compared with an exosome isolated from non-differentiated MSCs, wherein said at least one miRNA molecule is selected from the group comprising miRNA (miR)-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, or miR-4324, or any combination thereof. In some embodiments, an isolated MSC-NTF exosome comprises an increased amount of an miR-3663-3p. In some embodiments, an isolated MSC-NTF exosome comprises an increased amount of an miR-132-3p. In some embodiments, an isolated MSC-NTF exosome comprises an increased amount of an miR-150-3p. In some embodiments, an isolated MSC-NTF exosome comprises an increased amount of an miR-762. In some embodiments, an isolated MSC-NTF exosome comprises an increased amount of an miR-4327. In some embodiments, an isolated MSC-NTF exosome comprises an increased amount of an miR-3665. In some embodiments, an isolated MSC-NTF exosome comprises an increased amount of an miR-34a-5p. In some embodiments, an isolated MSC-NTF exosome comprises an increased amount of an miR-1915. In some embodiments, an isolated MSC-NTF exosome comprises an increased amount of an miR-34a-39. In some embodiments, an isolated MSC-NTF exosome comprises an increased amount of an miR-34b-5p. In some embodiments, an isolated MSC-NTF exosome comprises an increased amount of an miR-874\ In some embodiments, an isolated MSC-NTF exosome comprises an increased amount of an miR-4281. In some embodiments, an isolated MSC-NTF exosome comprises an increased amount of an miR-1207-5p. In some embodiments, an isolated MSC-NTF exosome comprises an increased amount of an miR-30b-5p. In some embodiments, an isolated MSC-NTF exosome comprises an increased amount of an miR-29b-3p. In some embodiments, an isolated MSC-NTF exosome comprises an increased amount of an miR-199b-5p. In some embodiments, an isolated MSC-NTF exosome comprises an increased amount of an miR-30e-5p. In some embodiments, an isolated MSC-NTF exosome comprises an increased amount of an miR-26a-5p. In some embodiments, an isolated MSC-NTF exosome comprises an increased amount of an miR-4324.

In some embodiments, an isolated MSC-NTF exosome comprises a decreased amount of at least one micro-RNA (miRNA) molecule compared with an exosome isolated from non-differentiated MSCs. In some embodiments, an isolated MSC-NTF exosome comprises a decreased amount of at least one micro-RNA (miRNA) molecule compared with an exosome isolated from non-differentiated MSCs, wherein said at least one miRNA molecule is selected from the group comprising miR-503, miR-3659, miR-3529-3p, miR-320b, miR-1275, miR-3132, miR-320a, miR-495, miR-181b-5p, miR-222-3p, miR-424-5p, miR-4284, miR-574-5p, miR-143-3p, miR-106a-5p, miR-455-3p, miR-20a-5p, miR-145-5p, miR-324-3p, miR-130b-3p, miR-1305, or miR-140-3p, or any combination thereof. In some embodiments, an isolated MSC-NTF exosome comprises a decreased amount of an miR-503. In some embodiments, an isolated MSC-NTF exosome comprises a decreased amount of an miR-3659. In some embodiments, an isolated MSC-NTF exosome comprises a decreased amount of an miR-3529-3p. In some embodiments, an isolated MSC-NTF exosome comprises a decreased amount of an miR-320b. In some embodiments, an isolated MSC-NTF exosome comprises a decreased amount of an miR-1275. In some embodiments, an isolated MSC-NTF exosome comprises a decreased amount of an miR-3132. In some embodiments, an isolated MSC-NTF exosome comprises a decreased amount of an miR-320a. In some embodiments, an isolated MSC-NTF exosome comprises a decreased amount of an miR-495. In some embodiments, an isolated MSC-NTF exosome comprises a decreased amount of an miR-181b-5p. In some embodiments, an isolated MSC-NTF exosome comprises a decreased amount of an miR-222-3p. In some embodiments, an isolated MSC-NTF exosome comprises a decreased amount of an miR-424-5p. In some embodiments, an isolated MSC-NTF exosome comprises a decreased amount of an miR-4284. In some embodiments, an isolated MSC-NTF exosome comprises a decreased amount of an miR-574-5p. In some embodiments, an isolated MSC-NTF exosome comprises a decreased amount of an miR-143-3p. In some embodiments, an isolated MSC-NTF exosome comprises a decreased amount of an miR-106a-5p. In some embodiments, an isolated MSC-NTF exosome comprises a decreased amount of an miR-455-3p. In some embodiments, an isolated MSC-NTF exosome comprises a decreased amount of an miR-20a-5p. In some embodiments, an isolated MSC-NTF exosome comprises a decreased amount of an miR-145-5p. In some embodiments, an isolated MSC-NTF exosome comprises a decreased amount of an miR-324-3p. In some embodiments, an isolated MSC-NTF exosome comprises a decreased amount of an miR-130b-3p. In some embodiments, an isolated MSC-NTF exosome comprises a decreased amount of an miR-1305. In some embodiments, an isolated MSC-NTF exosome comprises a decreased amount of an miR-140-3p.

In some embodiments, isolated MSC exosomes may be loaded with molecules not normally or naturally present in MSCs. These MSC exosomes therefore comprise modified MSC exosomes compared with exosome isolated from the same MSCs not loaded with additional molecules. In some embodiments, isolated MSC exosomes comprise molecules beneficial in the treatment of neurodegenerative diseases. In some embodiments, isolated MSC exosomes may be loaded with molecules beneficial in the treatment of neurodegenerative diseases.

In some embodiments, the isolated exosomes disclosed herein from MSCs, genetically modified MSCs, MSC-NTFs, or genetically modified MSC-NTFs, may be loaded with exogenous cargoes, such as a therapeutic miRNA, an siRNA, and/or therapeutic factors. Loading may be through exogenous means, as known in the art, or may be the result of expressing or highly expressing the miRNA, therapeutic factor, or siRNA in the MSC or MSC-NTF cells. In some embodiments, the isolated exosomes disclosed herein may be loaded with a nucleotide sequence encoding a therapeutic factor, wherein said nucleotide sequence is translated in a target cell. In some embodiments, the nucleotide sequence comprised in a modified exosome is expressed in the target cell. In some embodiments, nucleotide sequences comprise siRNA, miRNA, or encode therapeutic factors for example but not limited to growth factors. As a person of skill in the art would understand, the term "target cell" generally refers to a cell which is contacted or will eventually be contacted with the exosomes.

In some embodiments, isolated MSC-NTF exosomes may be loaded with molecules not normally present in MSC-NTF cells. In some embodiments, isolated MSC-NTF exosomes may be loaded with molecules not naturally present in exosomes isolated from MSC-NTF. In some isolated MSC-NTF exosomes comprise molecules beneficial in the treatment of neurodegenerative diseases.

In some embodiments, isolated MSC exosomes may be loaded with molecules not normally present in MSC cells. In some embodiments, isolated MSC exosomes may be loaded with molecules not naturally present in exosomes isolated from MSC. In some embodiments, these modified isolated MSC exosomes comprise molecules beneficial in the treatment of neurodegenerative diseases.

In some embodiments, the isolated exosomes disclosed herein may be loaded with exogenous cargoes, such as a therapeutic miRNA, an siRNA, and/or therapeutic factors. Loading may be through exogenous means, as known in the art, or may be the result of expressing or highly expressing the miRNA, therapeutic factor, or siRNA in the MSC or MSC-NTF cells. In some embodiments, the isolated exosomes disclosed herein may be loaded with a nucleotide sequence encoding a therapeutic factor, wherein said nucleotide sequence is translated in a target cell.

In some embodiments, exosomes may be loaded with exogenous cargoes using electroporation protocols adapted for nanoscale applications (see, e.g., Alvarez-Erviti et al. 2011, Nat Biotechnol 29: 341). Alternatively, El-Andaloussi et al. (Nature Protocols 7, 2112-2126(2012)) discloses how exosomes derived from cultured cells can be harnessed for delivery of siRNA in vitro and in vivo. Additional methods of passive or active loading of exosomes is described throughout the literature, for example but not limited to Xin Luan et al (2017) Acta Pharmacologica Sinica volume 38, pages 754-763; Dinh Ha et al., (2016) Acta Pharmaceutica Sinica B 6(4):287-296; Lamichhane et al., Mol. Pharmaceutics 12, 10, 3650-3657; and Shtam et al., (2013) Cell Communication and Signaling 11:88.

While isolated MSC-NTF exosomes or isolated modified MSC exosomes loaded with exogenous cargos may serve as nano-carriers, MSC and MSC-NTF derived exosomes maintain the therapeutic potential of their original cell of origin. Therefore, MSC and MSC-NTF derived exosomes may offer an expanded therapeutic option to benefit a larger number of patients. In some embodiments, modified MSC exosomes (loaded with at least one exogenous cargo) are used in methods disclosed herein to treat a subject in need. In some embodiments, modified MSC-NTF exosomes (loaded with at least one exogenous cargo) are used in methods disclosed herein to treat a subject in need.

In some embodiments, exosomes are loaded with an exogenous cargo to specifically target neurodegenerative diseases. A skilled artisan would recognize that these exosomes are therefore modified in relationship with exosomes isolated from MSC or MSC-NTF, as they now comprise at least one additional cargo. In some embodiment, exosomes are loaded with an exogenous cargo for use in methods of treating a neurodegenerative disease. In some embodiment, exosomes are loaded with an exogenous cargo for use in methods of treating amyotrophic lateral sclerosis (ALS). In some embodiment, exosomes are loaded with an exogenous cargo for use in methods of treating frontotemporal dementia (FTD). In some embodiment, exosomes are loaded with an exogenous cargo for use in methods of treating Parkinson's Disease (PD). In some embodiment, exosomes are loaded with an exogenous cargo for use in methods of treating multiple system atrophy (MSA). In some embodiment, exosomes are loaded with an exogenous cargo for use in methods of treating spinal muscular atrophy (SMA). In some embodiment, exosomes are loaded with an exogenous cargo for use in methods of treating multiple sclerosis (MS). In some embodiment, exosomes are loaded with an exogenous cargo for use in methods of treating Alzheimer's Disease (AD). In some embodiment, exosomes are loaded with an exogenous cargo for use in methods of treating Rett Syndrome. In some embodiment, exosomes are loaded with an exogenous cargo for use in methods of treating Cerebral Palsy (CP). In some embodiment, exosomes are loaded with an exogenous cargo for use in methods of treating Autism Spectrum Disorder (ASD). In some embodiment, exosomes are loaded with an exogenous cargo for use in methods of treating epilepsy.

As described herein, exosomes may comprise molecules naturally present in MSCs, molecules that have been highly expressed or newly expressed in genetically modified MSCs, or exogenously loaded cargoes, or any combination thereof. One skilled in the art would appreciate that as envisioned herein, exosomes in some embodiments comprise elements present in the MSCs from which they are isolated and may also include additional elements added to the exosomes at a later stage.

Similarly, as described herein, exosomes may comprise one or more NTFs naturally present in MSC-NTF cells or exogenously loaded as cargo. One skilled in the art would appreciate that as envisioned herein, exosomes in some embodiments comprise elements present in the MSC-NTF from which they are isolated and may also include additional elements added to the exosomes at a later stage. For example, selective motor neuron (MN) vulnerability occurs at different levels in the motor system of ALS patients. Neurons of the oculomotor (OMNs; CNIII), trochlear (CNIV), and abducens (CNVI) nuclei, which are located in the midbrain and control eye movement, show marked resistance to degeneration in ALS. Spinal MNs have been found to present a gradient of vulnerability. Depending on their contractile properties, motor units are classified as fast fatigable (FF), fast-fatigue-resistant (FR), or slow (S). In ALS, S motor neurons are more resistant and undergo axonal degeneration only at later stages, whereas FF motor neurons are the most vulnerable.

The selective resistance of OMNs may denote the molecular signature that renders a specific subset of neurons to be more resistant. It was shown that neuronal vulnerability is governed both by a lack of certain intrinsic beneficial factors, as well as the presence of detrimental molecules.

Insulin-like growth factor (IGF)-1 and 2 are key molecules identified as enriched in resistant motor neurons while matrix metalloproteinase-9 (MMP-9) was identified in vulnerable motor neurons.

Insulin-like growth factor-1 (IGF-1) protects deteriorating motor nerves and promotes growth and regeneration of motor nerve axons and their innervation into muscles. Viral-mediated IGF-1 delivery increases MN numbers, improves grip strength, delays progression, and prolongs survival in ALS rodents. IGF-1 receptor (IGF-1R), which mediates survival pathways upon IGF binding, was highly expressed in oculomotor neurons and on extraocular muscle endplates. In the clinic, subcutaneous (SC) IGF-1 administration to ALS patients did not demonstrate therapeutic efficacy. However, it is known that peripheral delivery of tolerable levels of IGF-1 may fail since the bioavailability in CSF and brain parenchyma in humans treated by SC administration is very low.

Insulin-like growth factor-2 (IGF-2) was shown to protect ALS patient motor neurons in-vitro. Similar to IGF-1, viral-mediated IGF-2 delivery to muscles of SOD1G93A ALS mice extended mice life-span by 10%, while preserving motor neurons and inducing motor axon regeneration. It was shown that IGF-2 remained preferential to oculomotor neurons in end-stage ALS patient tissue, indicating that this growth factor could play a protective role in these resistant motor neurons in disease.

Growth differentiation factor-5 (GDF5) is a member of the TGFI3 superfamily, and a part of the bone morphogenetic (BMP) protein subfamily. It has neurotrophic and protective actions on nigrostriatal dopaminergic neurons in vitro and in vivo.

In some embodiments, an isolated modified MSC exosome disclosed herein comprises a growth factor. In some embodiments, an isolated modified MSC exosome disclosed herein comprises an increased amount of a growth factor compared with exosome isolated from non-genetically modified MSC.

In some embodiments, an isolated modified MSC exosome disclosed herein comprises a growth factor comprising an IGF-1, an IGF-2, or a GDF5, or any combination thereof. In some embodiments, the growth factor is a human growth factor. In some embodiments, an isolated modified MSC exosome disclosed herein comprises an increased amount of a growth factor compared with exosome isolated from non-genetically modified MSC, said growth factor comprising an IGF-1, an IGF-2, or an GDF5, or any combination thereof. In some embodiments, an isolated modified MSC exosome comprises an IGF-1. In some embodiments, an isolated modified MSC exosome comprises an increased amount of an IGF-1 compared with non-genetically modified MSC. In some embodiments, an isolated modified MSC exosome comprises an IGF-2. In some embodiments, an isolated modified MSC exosome comprises an increased amount of an IGF-2 compared with non-genetically modified MSC. In some embodiments, an isolated modified MSC exosome comprises a GDF5. In some embodiments, an isolated modified MSC exosome comprises an increased amount of a GDF5 compared with non-genetically modified MSC. In some embodiments, IGF-1, IGF-2, and GDF-5 are human IGF-1, human IGF-2, and human GDF-5, respectively.

In some embodiments, an isolated modified MSC exosome comprising IGF-1 is isolated from a genetically modified MSC expressing IGF-1. In some embodiments, an isolated modified MSC exosome comprising IGF-2 is isolated from a genetically modified MSC cell expressing IGF-2. In some embodiments, an isolated modified MSC exosome comprising GDF-5 is isolated from a genetically modified MSC expressing GDF-5.

In some embodiments, an isolated modified MSC exosome comprising IGF-1 is isolated from a genetically modified MSC highly expressing IGF-1. In some embodiments an isolated modified MSC exosome comprising IGF-2 is isolated from a genetically modified MSC highly expressing IGF-2. In some embodiments, an isolated modified MSC exosome comprising GDF-5 is isolated from a genetically modified MSC highly expressing GDF-5.

In some embodiments, an isolated modified MSC exosome comprising IGF-1 may be useful in protecting deteriorating motor nerves and used to promote growth and regeneration of motor nerve axons. In some embodiments, an isolated modified MSC exosome comprising IGF-2 may be useful in protecting motor neurons and inducing motor axon regeneration. In some embodiments, an isolated modified MSC exosome comprising GDF-5 may be useful in protecting neurons and enhancing neurogenesis.

In some embodiments, an isolated MSC-NTF exosome disclosed herein comprises a growth factor. In some embodiments, an isolated MSC-NTF exosome disclosed herein comprises an increased amount of a growth factor compared with exosome isolated from non-differentiated MSC. In some embodiments, an isolated MSC-NTF exosome disclosed herein comprises an NTF. In some embodiments, an isolated MSC-NTF exosome disclosed herein comprises an increased amount of an NTF compared with exosome isolated from non-differentiated MSCs.

In some embodiments, an isolated MSC-NTF exosome disclosed herein comprises a growth factor comprising an IGF-1, an IGF-2, or a GDF5, or any combination thereof. In some embodiments, the growth factor is a human growth factor. In some embodiments, an isolated MSC-NTF exosome disclosed herein comprises an increased amount of a growth factor compared with exosome isolated from non-differentiated MSCs, said growth factor comprising an IGF-1, an IGF-2, or an GDF5, or any combination thereof. In some embodiments, an isolated MSC-NTF exosome comprises an IGF-1. In some embodiments, an isolated MSC-NTF exosome comprises an increased amount of an IGF-1 compared with non-differentiated MSCs. In some embodiments, an isolated MSC-NTF exosome comprises an IGF-2. In some embodiments, an isolated MSC-NTF exosome comprises an increased amount of an IGF-2 compared with non-differentiated MSCs. In some embodiments, an isolated MSC-NTF exosome comprises an GDF5. In some embodiments, an isolated MSC-NTF exosome comprises an increased amount of an GDF5 compared with non-differentiated MSCs. In some embodiments, IGF-1, IGF-2, and GDF-5 are human IGF-1, human IGF-2, and human GDF-5, respectively.

In some embodiments, an isolated MSC-NTF exosome comprising IGF-1 is isolated from an MSC-NTF cell expressing IGF-1. In some embodiments, an isolated MSC-NTF exosome comprising IGF-2 is isolated from an MSC-NTF cell expressing IGF-2. In some embodiments, an isolated MSC-NTF exosome comprising GDF-5 is isolated from an MSC-NTF cell expressing GDF-5.

In some embodiments, an isolated MSC-NTF exosome comprising IGF-1 is isolated from an MSC-NTF cell highly expressing IGF-1. In some embodiments, an isolated MSC-NTF exosome comprising IGF-2 is isolated from an MSC-NTF cell highly expressing IGF-2. In some embodiments, an isolated MSC-NTF exosome comprising GDF-5 is isolated from an MSC-NTF cell highly expressing GDF-5.

In some embodiments, isolated MSC-NTF exosomes comprising IGF-1 may be useful in protecting deteriorating motor nerves and used to promote growth and regeneration of motor nerve axons. In some embodiments, isolated MSC-NTF exosomes comprising IGF-2 may be useful in protecting motor neurons and inducing motor axon regeneration. In some embodiments, isolated MSC-NTF exosomes comprising GDF-5 may be useful in protecting neurons and enhancing neurogenesis.

In some embodiments, an isolated modified MSC-NTF exosome comprises a galectin-1 molecule. In some embodiments, an isolated modified MSC exosome comprises a galectin-1 molecule.

Galectin-1 (LGALS1) is a galactose-binding lectin and is a multifunctional molecule involved in the regulation of cell adhesion, cell proliferation, and programmed cell death. In the nervous system, galectin-1 is involved in the proliferation of neural stem cells, neritic outgrowth, and cellular adaptation of redox status, as well as the regulation of glutamate toxicity via interaction with the NR1 subunit. In an α-synuclein-enriched cellular model, galectin-1 played an important role in the transmission control of aggregated a-synuclein. Galectin-1 treatment significantly decreased the expression of clathrin and EEA1 and increased the expression of NR1, with a concomitant increase in NMDA receptor binding, which led to decreased levels of internalized cytosolic a-synuclein (Oh et al., 2016, Cell Reports 14, 835-849).

In some embodiments, an isolated modified MSC exosome disclosed herein comprises a galectin-1. In some embodiments, an isolated modified MSC exosome disclosed herein comprises an increased amount of a galectin-1 compared with exosome isolated from non-genetically modified MSCs. In some embodiments, an isolated modified MSC exosome disclosed herein comprises a human galectin-1. In some embodiments, an isolated modified MSC exosome disclosed herein comprises an increased amount of a human galectin-1 compared with exosome isolated from non-genetically modified MSCs.

In some embodiments, an isolated modified MSC-NTF exosome disclosed herein comprises a galectin-1. In some embodiments, an isolated modified MSC-NTF exosome disclosed herein comprises an increased amount of a galectin-1 compared with exosome isolated from non-genetically modified MSC-NTFs. In some embodiments, an isolated modified MSC-NTF exosome disclosed herein comprises a human galectin-1. In some embodiments, an isolated modified MSC-NTF exosome disclosed herein comprises an increased amount of a human galectin-1 compared with exosome isolated from non-genetically modified MSC-NTFs.

In some embodiments, an isolated modified MSC exosome comprising galectin-1 is isolated from a genetically modified MSC expressing galectin-1. In some embodiments, the genetically modified MSC cell highly expresses galectin-1. In some embodiments, an isolated modified MSC-NTF exosome comprising galectin-1 is isolated from a genetically modified MSC-NTF cell expressing galectin-1. In some embodiments, the genetically modified MSC-NTF cell highly expresses galectin-1.

In some embodiments, an isolated modified MSC exosome comprising a galectin-1 molecule may be useful in protecting deteriorating motor nerves and used to promote growth and regeneration of motor nerve axons. In some embodiments, an isolated modified MSC-NTF exosome comprising a galectin-1 molecule may be useful in protecting motor neurons and inducing motor axon regeneration.

In some embodiments, an isolated modified MSC exosome comprising galectin-1 is isolated from a modified MSC cell expressing galectin-1. In some embodiments, an isolated MSC-NTF exosome comprising galectin-1 is isolated from an MSC-NTF cell expressing galectin-1. In some embodiments, an isolated modified MSC exosome comprising galectin-1 is isolated from a modified MSC cell highly expressing galectin-1. In some embodiments, an isolated MSC-NTF exosome comprising galectin-1 is isolated from an MSC-NTF cell highly expressing galectin-1.

miR-7, which is expressed mainly in neurons, has been shown to repress alpha-synuclein protein levels, protects cells against oxidative stress, protects neurons against MPP+ induced cell death and protects dopaminergic neurons against PD-like degeneration via suppressing nod-like receptor protein 3 (NLRP3) inflammasome-mediated neuroinflammation.

One method to decrease the amount of a target protein known to be detrimental in disease or disorders is through the use of miRNA targeted to a particular protein or peptide. Use of a miRNA molecule may downregulate expression or halt the expression of the target protein or peptide.

In some embodiments, an isolated modified MSC exosome comprises a miRNA molecule that targets a protein known to be a target of treatment in a neurodegenerative disease. In some embodiments an isolated modified MSC exosome comprises an increased amount of a miRNA molecule that targets a protein known to be a target of treatment of neurodegenerative diseases, compared with non-genetically modified MSC. In some embodiments, use of a miRNA molecule downregulates expression or inhibits the expression of the target protein.

In some embodiments, an isolated modified MSC exosome comprises an miR-7 molecule. In some embodiments, an isolated MSC-NTF exosome comprises an increased amount of an miR-7 compared with non-genetically modified MSCs.

In some embodiments, an isolated modified MSC exosome comprising miR-7 is isolated from a genetically modified MSC cell highly expressing miR-7. In some embodiments, an isolated modified MSC exosome comprising miR-7 is isolated from a genetically modified MSC cell expressing miR-7.

In some embodiments, an isolated modified MSC exosome comprising miR-7 may be useful in repressing alpha-synuclein protein levels, protecting cells against oxidative stress, protecting neurons against MPP+ induced cell death, and protecting dopaminergic neurons against PD-like degeneration via suppressing nod-like receptor protein 3 (NLRP3) inflammasome-mediated neuroinflammation.

In some embodiments an isolated MSC-NTF exosome comprises a miRNA molecule that targets a protein known to be a target of treatment in a neurodegenerative disease. In some embodiments an isolated MSC-NTF exosome comprises an increased amount of a miRNA molecule that targets a protein known to be a target of treatment of neurodegenerative diseases, compared with non-differentiated MSCs. In some embodiments, use of a miRNA molecule downregulates expression or halt the expression of the target protein.

In some embodiments, an isolated MSC-NTF exosome comprises an miR-7 molecule. In some embodiments, an isolated MSC-NTF exosome comprises an increased amount of an miR-7 compared with non-differentiated MSCs.

In some embodiments, an isolated MSC-NTF exosome comprising miR-7 is isolated from an MSC-NTF cell highly expressing miR-7. In some embodiments, an isolated MSC-NTF exosome comprising miR-7 is isolated from an MSC-NTF cell expressing miR-7.

In some embodiments, isolated MSC-NTF exosomes comprising miR-7 may be useful repressing alpha-synuclein protein levels, protecting cells against oxidative stress, protecting neurons against MPP+ induced cell death, and protecting dopaminergic neurons against PD-like degeneration via suppressing nod-like receptor protein 3 (NLRP3) inflammasome-mediated neuroinflammation.

Matrix metalloproteinase-9 (MMP-9) is a matrixin, an enzyme that is involved in the degradation of the extracellular matrix. MMP-9 is strongly expressed by most cranial and spinal motor neurons and absent from oculomotor and Onuf's nuclei (a distinct group of neurons located in the ventral part (laminae IX) of the anterior horn of the sacral region of the human spinal cord). Strikingly, it was also undetectable in S motor neurons in the spinal cord. This suggests MMP-9 as a prospective marker for all ALS-vulnerable motor neurons. Functionally, even partial reduction of MMP-9 levels in SOD1 mice leads to pronounced delay in muscle denervation and a significant extension of lifespan. Moreover, MMP-9 acts early in the disease process, facilitating the onset of subtype-specific ER stress. Selective introduction of MMP-9 into mice was shown to be sufficient to induce degeneration of fast MNs, confirming the detrimental role of this metalloproteinase. Interestingly, it was also found that MMP9 induces microglia activation. Therefore MMP-9 might be a strong candidate therapeutic target for neurodegenerative diseases, for example but not limited to ALS and PD.

MMP-9 expression is increased in the substantia nigra and striatum of PD animal models. Moreover, MMP-9-expressing microglia and astrocytes, increase concomitantly to a prominent inflammation. MMP-9 knockout lowers the number of active microglia, correlated with an increase in the number of functional dopaminergic neurons.

One method to decrease the amount of a target protein known to be detrimental in disease or disorders, is through the use of siRNA complementary to the mRNA encoding the protein. Use of an siRNA molecule may then downregulate expression or halt the expression of the target polypeptide.

In some embodiments, an isolated modified MSC exosome comprises an siRNA molecule. In some embodiments, the siRNA molecule is complementary to an mRNA encoding a known target of neurodegenerative diseases. In some embodiments, the siRNA targets the reduction or elimination of expression of a known target of neurodegenerative diseases.

In some embodiments, an isolated modified MSC exosome comprises an siRNA complementary to human metalloproteinase-9 (MMP-9). In some embodiments, an isolated modified MSC exosome comprises an siRNA complementary to a portion of a human metalloproteinase-9 (MMP-9). In some embodiments, an isolated modified MSC exosome comprising siRNA may be useful in reducing the level of MMP-9 and thereby protecting motor neurons.

In some embodiments, an isolated MSC-NTF exosome comprises an siRNA molecule. In some embodiments, the siRNA molecule is complementary to an mRNA encoding a known target of neurodegenerative diseases. In some embodiments, the siRNA targets the reduction or elimination of expression of a known target of neurodegenerative diseases.

In some embodiments, an isolated MSC-NTF exosome comprises an siRNA complementary to human metalloproteinase-9 (MMP-9). In some embodiments, an isolated MSC-NTF exosome comprises an siRNA complementary to a portion of a human metalloproteinase-9 (MMP-9). In some embodiments, isolated MSC-NTF exosomes comprising siRNA may be useful in reducing the level of MMP-9 and thereby protecting motor neurons.

In some embodiments, disclosed herein is a pharmaceutical composition comprising an isolated modified MSC exosome as described throughout, and a pharmaceutically acceptable carrier. In some embodiments, a "pharmaceutical composition" encompasses a preparation of one or more of the active ingredients described herein with other chemical components such as physiologically suitable carriers and excipients. The purpose of a pharmaceutical composition is to facilitate administration of an active ingredient to an organism.

In some embodiments, "active ingredient" refers to the isolated exosomes derived from MSC-NTF cells, which is accountable for the biological effect.

In another embodiment, the phrase "pharmaceutically acceptable carrier" encompasses a carrier or a diluent that does not cause significant irritation to an organism and does not abrogate the biological activity and properties of the administered compound.

In some embodiments, the composition comprises an isolated modified MSC exosome, wherein the composition is essentially free of extra-exosomal material. One skilled in the art would appreciate that extra-exosomal materials include, but are not limited to, nucleic acid-protein complexes, nucleic acids, and/or proteins not normally found within exosomes. In some embodiments, a composition of isolated modified MSC exosomes may be free of cells such as MSCs, or cell fragments thereof. In some embodiments, a composition may be free or substantially free of conditioned media. Typically, the isolated exosomes are provided at a higher concentration in a composition than exosomes present in unmanipulated conditioned media.

In some embodiments, a pharmaceutical composition comprising an isolated modified MSC exosome as described throughout, may be administered in combination with MSC or MSC-NTF cells.

In some embodiments, disclosed herein is a pharmaceutical composition comprising an isolated MSC-NTF exosome as described throughout. In some embodiments, the composition comprises isolated MSC-NTF exosomes, wherein the composition is essentially free of extra-exosomal material. One skilled in the art would appreciate that extra-exosomal materials include but are not limited to nucleic acid-protein complexes, nucleic acids, and/or proteins not normal found within exosomes. In some embodiments, a composition of isolated exosomes may be free of cells such as MSCs or MSC-NTF, or cell fragments thereof. In some embodiments, a composition may be free or substantially free of conditioned media. Typically, the isolated exosomes are provided at a higher concentration in a composition than exosomes present in unmanipulated conditioned media.

In some embodiments, a pharmaceutical composition comprising an isolated MSC-NTF exosome as described throughout, may be administered in combination with MSC-NTF cells. In certain embodiments, the isolated MSC-NTF exosome and the MSC-NTF cell are comprised in separate compositions. In certain embodiments, the isolated MSC-NTF exosome and the MSC-NTF cell are administered separately.

In some embodiments, a pharmaceutical composition comprises a pharmaceutically acceptable carrier or diluent. Such preparations may routinely contain pharmaceutically acceptable concentrations of salt, buffering agents, preservatives, compatible carriers, and may optionally comprise other (i.e., secondary) therapeutic agents.

In some embodiments, a pharmaceutically acceptable carrier or diluent is a pharmaceutically acceptable material, composition or vehicle, such as a liquid or solid filler, diluent, excipient, solvent or encapsulating material, involved in carrying or transporting a prophylactically or therapeutically active agent. Each carrier must be "acceptable" in the sense of being compatible with the other ingredients of the formulation and not injurious to the subject. Some examples of materials which can serve as pharmaceutically acceptable carriers include sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and other non-toxic compatible substances employed in pharmaceutical formulations.

The compositions may take such forms as water-soluble suspensions, solutions or emulsions in oily or aqueous vehicles, and may contain formulatory agents such as suspending, stabilizing and/or dispersing agents. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or agents which increase solubility. Alternatively, the exosomes may be in lyophilized or other powder or solid form for constitution with a suitable vehicle, e.g., sterile pyrogen-free water, before use.

In some embodiments, an isolated exosome population derived from MSC-NTF cells comprises an increased quantity of at least one cargo protein comprising a LIF protein, a CXCL1 protein, an IL13 protein, a VEGFA protein, or a GDF15 protein, or any combination thereof, compared with the quantity of said at least one cargo protein in an isolated exosome population derived from control MSCs.

In some embodiments, an isolated exosome population derived from MSC-NTF cells comprises an increased quantity of at least 2 cargo protein comprising a LIF protein, a CXCL1 protein, an IL13 protein, a VEGFA protein, or a GDF15 protein, or any combination thereof, compared with the quantity of said at least one cargo protein in an isolated exosome population derived from control MSCs. In some embodiments, an isolated exosome population derived from MSC-NTF cells comprises an increased quantity of at least 3, 4, or 5 cargo protein comprising a LIF protein, a CXCL1 protein, an IL13 protein, a VEGFA protein, or a GDF15 protein, or any combination thereof, compared with the quantity of said at least one cargo protein in an isolated exosome population derived from control MSCs.

The technology provided herein provides, in some embodiments, an isolated exosome comprising a protein selected from the group consisting of SPINT2, IL36G, and TNFRSF10B.

In certain embodiments, the isolated exosome comprises the protein SPINT2. In certain embodiments, the isolated exosome comprises the protein IL36G. In certain embodiments, the isolated exosome comprises the protein TNFRSF10B. In certain embodiments, the isolated exosome comprises the proteins SPINT2 and IL36G. In certain embodiments, the isolated exosome comprises the proteins IL36G and TNFRSF10B. In certain embodiments, the isolated exosome comprises the proteins SPINT2 and TNFRSF10B. In certain embodiments, the isolated exosome comprises the proteins SPINT2, IL36G, and TNFRSF10B.

In certain embodiments, an exosome comprises a protein TNFSF14.

In certain embodiments, an MSC-NTF derived exosome population further comprises at least one additional protein said protein comprising: IL36A, CCL7, MMP10, PIFG, CXCL8, LTA, CXCL6, MMP3, CHI3L1, IL11, FGF2, CXCL5, GAS1, JAML, TGFBR3, MEPE, IL6, PDGFA, CCL4, CCL21, CCL2, MIF, PLAU, ANGPTL4, CTSB, BSG, CCL5, TPO, IL23, IL1RL1, SPP1, F11R, INHBA, FAP, and any combination thereof. In some embodiments, an MSC-NTF derived exosome population further comprises at least one additional protein comprising LYVE1, FRZB, CCL11, C5a, and any combination thereof.

In certain embodiments, an exosome comprises a LIF protein. In certain embodiments, an exosome comprises a CXCL1 protein. In certain embodiments, an exosome comprises a IL36A protein. In certain embodiments, an exosome comprises a VEGFA protein. In certain embodiments, an exosome comprises a GDF15 protein. In certain embodiments, an exosome comprises a CCL7 protein. In certain embodiments, an exosome comprises a MMP10 protein. In certain embodiments, an exosome comprises a PIFG protein. In certain embodiments, an exosome comprises a CXCL8 protein. In certain embodiments, an exosome comprises a LTA protein. In certain embodiments, an exosome comprises a CXCL6 protein. In certain embodiments, an exosome comprises a MMP3 protein. In certain embodiments, an exosome comprises a CHI3L1 protein. In certain embodiments, an exosome comprises a IL11 protein. In certain embodiments, an exosome comprises a FGF2 protein. In certain embodiments, an exosome comprises a CXCL5 protein. In certain embodiments, an exosome comprises a GAS1 protein. In certain embodiments, an exosome comprises a JAML protein. In certain embodiments, an exosome comprises a TGFBR3 protein. In certain embodiments, an exosome comprises a MEPE protein. In certain embodiments, an exosome comprises a IL6 protein. In certain embodiments, an exosome comprises a PDGFA protein. In certain embodiments, an exosome comprises a CCL4 protein. In certain embodiments, an exosome comprises a CCL21 protein. In certain embodiments, an exosome comprises a IL13 protein. In certain embodiments, an exosome comprises a VEGFA protein. In certain embodiments, an exosome comprises a CCL2 protein. In certain embodiments, an exosome comprises a MIF protein. In certain embodiments, an exosome comprises a GDF15 protein. In certain embodiments, an exosome comprises a PLAU protein. In certain embodiments, an exosome comprises an ANGPTL4 protein. In certain embodiments, an exosome comprises a CTSB protein. In certain embodiments, an exosome comprises a BSG protein. In certain embodiments, an exosome comprises a CCL5 protein. In certain embodiments, an exosome comprises a TPO protein. In certain embodiments, an exosome comprises a IL23 protein. In certain embodiments, an exosome comprises a IL1RL1 protein. In certain embodiments, an exosome comprises a SPP1 protein. In certain embodiments, an exosome comprises a F11R protein. In certain embodiments, an exosome comprises a INHBA protein. In certain embodiments, an exosome comprises a FAP protein. In certain embodiments, an exosome comprises a LYVE1 protein. In certain embodiments, an exosome comprises a FRZB protein. In certain embodiments, an exosome comprises a CCL11 protein. In certain embodiments, an exosome comprises a C5a protein.

A skilled artisan would appreciate that an isolated MSC-NTF derived population of exosomes may comprise certain proteins in increased amounts compared with exosomes derived from control MSC cells. In some embodiments, a cargo protein present in an isolated MSC-NTF derived exosome population is present in an increased quantity compared with exosomes derived from control MSC cells. In some embodiments, an increased quantity comprises a fold-increase.

In some embodiments, an increased quantity of a cargo protein comprises a 2-fold-increase compared with isolated exosomes from control MSC cells. In some embodiments, an increased quantity of a cargo protein comprises a 3, 4, 5, 6, 7, 8, 9, 10, 11, 12, 13, 14, 15, 16, 17, 18, 19, 20, 21, 22, 23, 24, 25, 26, 27, 28, 29, or 30 fold-increase compared with isolated exosomes from control MSC cells. In some embodiments, an increased quantity of a cargo protein comprises at least a 2-fold-increase compared with isolated exosomes from control MSC cells. In some embodiments, an increased quantity of a cargo protein comprises at least a 3, 4, 5, 6, 7, 8, 9, 10, 11, 12, 13, 14, 15, 16, 17, 18, 19, 20, 21, 22, 23, 24, 25, 26, 27, 28, 29, or 30 fold-increase compared with isolated exosomes from control MSC cells. In some embodiments, an increased quantity of a cargo protein comprises greater than a 30-fold-increase compared with isolated exosomes from control MSC cells. In some embodiments, an increased quantity of a cargo protein comprises a 30, 31, 32, 33, 34, 35, 36, 37, 38, 39, 40, 41, 42, 43, 44, 45, 46, 47, 48, 49, or 50 fold-increase compared with isolated exosomes from control MSC cells. In some embodiments, an increased quantity of a cargo protein comprises at least a 30, 31, 32, 33, 34, 35, 36, 37, 38, 39, 40, 41, 42, 43, 44, 45, 46, 47, 48, 49, or 50 fold-increase compared with isolated exosomes from control MSC cells.

Throughout this application, various embodiments may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

In certain embodiments, the exosome further comprises one or more markers selected from the group consisting of cluster of differentiation (CD)9, CD29, CD63, CD81, CD44, CD49, CD73, CD90, CD105, CD61, CD271, ALIX, tumor susceptibility gene (TSG)101, and any combination thereof.

In certain embodiments, the exosome further comprises the marker CD9. In certain embodiments, the exosome further comprises the marker CD29. In certain embodiments, the exosome further comprises the marker CD63. In certain embodiments, the exosome further comprises the marker CD81. In certain embodiments, the exosome further comprises the marker CD44. In certain embodiments, the exosome further comprises the marker CD49. In certain embodiments, the exosome further comprises the marker CD73. In certain embodiments, the exosome further comprises the marker CD90. In certain embodiments, the exosome further comprises the marker CD105. In certain embodiments, the exosome further comprises the marker CD61. In certain embodiments, the exosome further comprises the marker CD271. In certain embodiments, the exosome further comprises the marker ALIX. In certain embodiments, the exosome further comprises the marker TSG101.

In certain embodiments, the exosome is devoid of one or more markers selected from the group consisting of CD3, CD5, CD14, CD19, CD20, CD34, CD45, CD11B, FMC7, calnexin, human leukocyte antigen-antigen D related (HLA-DR), and any combination thereof.

In certain embodiments, the exosome is devoid of the marker CD3. In certain embodiments, the exosome is devoid of the marker CD5. In certain embodiments, the exosome is devoid of the marker CD14. In certain embodiments, the exosome is devoid of the marker CD19. In certain embodiments, the exosome is devoid of the marker CD20. In certain embodiments, the exosome is devoid of the marker CD34. In certain embodiments, the exosome is devoid of the marker CD45. In certain embodiments, the exosome is devoid of the marker CD11B. In certain embodiments, the exosome is devoid of the marker FMC7. In certain embodiments, the exosome is devoid of the marker calnexin. In certain embodiments, the exosome is devoid of the marker HLA-DR.

In certain embodiments, the exosome comprises a higher level of a protein selected from the group consisting of SPINT2, TNFSF14, IL36G, TNFRSF10B, IL36A, CCL7, MMP10, PIFG, CXCL8, LTA, LIF, CXCL1, CXCL6, MMP3, CHI3L1, IL11, FGF2, CXCL5, GAS1, JAML, TGFBR3, MEPE, IL6, PDGFA, CCL4, CCL21, IL13, VEGFA, CCL2, MIF, GDF15, PLAU, ANGPTL4, CTSB, BSG, CCL5, TPO, IL23, IL1RL1, SPP1, F11R, INHBA, and FAP, and any combination thereof, compared to the level of the same protein in a corresponding exosome derived from a control MSC. In certain embodiments, the exosome comprises a lower level of a protein selected from the group consisting of LYVE1, FRZB, CCL11, C5a, and any combination thereof, compared to the level of the same protein in a corresponding exosome derived from a control MSC.

In some embodiments, the protein having increased quantity in an isolated exosome population is an NTF. In certain embodiments, an exosome comprises a higher level of a protein, for example an NTF, compared to the level of the same protein in a corresponding exosome derived from control MSC. In some embodiments, the NTF present in increased quantity comprises a LIF protein. In some embodiments, the NTF present in increased quantity comprises a VEGF protein. In some embodiments, the NTF present in increased quantity comprises a VEGFA protein. In some embodiments, the NTF present in increased quantity comprises a GDF15 protein. In some embodiments, the NTF present in increased quantity comprises a FGF2 protein.

In some embodiments, the NTF present in increased quantity comprises a combination of NTFs selected from LIF, VEGF, VEGFA, GDF15, and FGF2 proteins. In some embodiments, the NTF present in increased quantity comprises a combination of NTFs comprising LIF, VEGF, VEGFA, GDF15, and FGF2 proteins. In some embodiments, the NTF present in increased quantity comprises a combination of NTFs comprising LIF and VEGFA, and GDF15 proteins. In some embodiments, the NTF present in increased quantity comprises a combination of NTFs comprising LIF and VEGFA proteins. In some embodiments, the NTF present in increased quantity comprises a combination of NTFs comprising LIF and GDF15 proteins. In some embodiments, the NTF present in increased quantity comprises a combination of NTFs comprising VEGFA, and GDF15 proteins. The term "a corresponding exosome derived from a MSC" or "control exosome" as used herein would by understood by a person of skill in the field as an exosome secreted from a control MSC, which has not been differentiated or manipulated to comprise or be devoid of any particular protein.

In certain embodiments, the exosome comprises a higher level of SPINT2 compared to the level of the same protein in a corresponding exosome derived from a control MSC. In certain embodiments, the exosome comprises a higher level of TNFSF14 compared to the level of the same protein in a corresponding exosome derived from a control MSC. In certain embodiments, the exosome comprises a higher level of IL36G compared to the level of the same protein in a corresponding exosome derived from a control MSC. In certain embodiments, the exosome comprises a higher level of TNFRSF10B compared to the level of the same protein in a corresponding exosome derived from a control MSC. In certain embodiments, the exosome comprises a higher level of IL36A compared to the level of the same protein in a corresponding exosome derived from a control MSC. In certain embodiments, the exosome comprises a higher level of CCL7 compared to the level of the same protein in a corresponding exosome derived from a control MSC. In certain embodiments, the exosome comprises a higher level of MMP10 compared to the level of the same protein in a corresponding exosome derived from a control MSC. In certain embodiments, the exosome comprises a higher level of PIFG compared to the level of the same protein in a corresponding exosome derived from a control MSC. In certain embodiments, the exosome comprises a higher level of CXCL8 compared to the level of the same protein in a corresponding exosome derived from a control MSC. In certain embodiments, the exosome comprises a higher level of LTA compared to the level of the same protein in a corresponding exosome derived from a control MSC. In certain embodiments, the exosome comprises a higher level of LIF compared to the level of the same protein in a corresponding exosome derived from a control MSC. In certain embodiments, the exosome comprises a higher level of CXCL1 compared to the level of the same protein in a corresponding exosome derived from a control MSC. In certain embodiments, the exosome comprises a higher level of CXCL6 compared to the level of the same protein in a corresponding exosome derived from a control MSC. In certain embodiments, the exosome comprises a higher level of MMP3 compared to the level of the same protein in a corresponding exosome derived from a control MSC. In certain embodiments, the exosome comprises a higher level of CHI3L1 compared to the level of the same protein in a corresponding exosome derived from a control MSC. In certain embodiments, the exosome comprises a higher level of IL11 compared to the level of the same protein in a corresponding exosome derived from a control MSC. In certain embodiments, the exosome comprises a higher level of FGF2 compared to the level of the same protein in a corresponding exosome derived from a control MSC. In certain embodiments, the exosome comprises a higher level of CXCL5 compared to the level of the same protein in a corresponding exosome derived from a control MSC. In certain embodiments, the exosome comprises a higher level of GAS1 compared to the level of the same protein in a corresponding exosome derived from a control MSC. In certain embodiments, the exosome comprises a higher level of JAML compared to the level of the same protein in a corresponding exosome derived from a control MSC. In certain embodiments, the exosome comprises a higher level of TGFBR3 compared to the level of the same protein in a corresponding exosome derived from a control MSC. In certain embodiments, the exosome comprises a higher level of MEPE compared to the level of the same protein in a corresponding exosome derived from a control MSC. In certain embodiments, the exosome comprises a higher level of IL6 compared to the level of the same protein in a corresponding exosome derived from a control MSC. In certain embodiments, the exosome comprises a higher level of PDGFA compared to the level of the same protein in a corresponding exosome derived from a control MSC. In certain embodiments, the exosome comprises a higher level of CCL4 compared to the level of the same protein in a corresponding exosome derived from a control MSC. In certain embodiments, the exosome comprises a higher level of CCL21 compared to the level of the same protein in a corresponding exosome derived from a control MSC. In certain embodiments, the exosome comprises a higher level of IL13 compared to the level of the same protein in a corresponding exosome derived from a control MSC. In certain embodiments, the exosome comprises a higher level of VEGFA compared to the level of the same protein in a corresponding exosome derived from a control MSC. In certain embodiments, the exosome comprises a higher level of CCL2 compared to the level of the same protein in a corresponding exosome derived from a control MSC. In certain embodiments, the exosome comprises a higher level of MIF compared to the level of the same protein in a corresponding exosome derived from a control MSC. In certain embodiments, the exosome comprises a higher level of GDF15 compared to the level of the same protein in a corresponding exosome derived from a control MSC. In certain embodiments, the exosome comprises a higher level of PLAU compared to the level of the same protein in a corresponding exosome derived from a control MSC. In certain embodiments, the exosome comprises a higher level of ANGPTL4 compared to the level of the same protein in a corresponding exosome derived from a control MSC. In certain embodiments, the exosome comprises a higher level of CTSB compared to the level of the same protein in a corresponding exosome derived from a control MSC. In certain embodiments, the exosome comprises a higher level of BSG compared to the level of the same protein in a corresponding exosome derived from a control MSC. In certain embodiments, the exosome comprises a higher level of CCL5 compared to the level of the same protein in a corresponding exosome derived from a control MSC. In certain embodiments, the exosome comprises a higher level of TPO compared to the level of the same protein in a corresponding exosome derived from a control MSC. In certain embodiments, the exosome comprises a higher level of IL23 compared to the level of the same protein in a corresponding exosome derived from a control MSC. In certain embodiments, the exosome comprises a higher level of IL1RL1 compared to the level of the same protein in a corresponding exosome derived from a control MSC. In certain embodiments, the exosome comprises a higher level of SPP1 compared to the level of the same protein in a corresponding exosome derived from a control MSC. In certain embodiments, the exosome comprises a higher level of F11R compared to the level of the same protein in a corresponding exosome derived from a control MSC. In certain embodiments, the exosome comprises a higher level of INHBA compared to the level of the same protein in a corresponding exosome derived from a control MSC. In certain embodiments, the exosome comprises a higher level of FAP compared to the level of the same protein in a corresponding exosome derived from a control MSC.

In certain embodiments, the MSC is selected from the group consisting of bone marrow MSCs, adipocyte MSCs, dental pulp MSCs, placenta MSCs, synovial membrane MSCs, peripheral blood MSCs, oral mucosa MSCs, periodontal ligament MSCs, endometrium MSCs, umbilical cord MSCs, and umbilical cord blood MSCs.

In certain embodiments, the MSC is bone marrow MSCs. In certain embodiments, the MSC is adipocyte MSCs. In certain embodiments, the MSC is dental pulp MSCs. In certain embodiments, the MSC is placenta MSCs. In certain embodiments, the MSC is synovial membrane MSCs. In certain embodiments, the MSC is peripheral blood MSCs. In certain embodiments, the MSC is oral mucosa MSCs. In certain embodiments, the MSC is periodontal ligament MSCs. In certain embodiments, the MSC is endometrium MSCs. In certain embodiments, the MSC is umbilical cord MSCs. In certain embodiments, the MSC is umbilical cord blood MSCs.

In certain embodiments, the exosome further comprises one or more neurotrophic factors (NTF) selected from the group consisting of a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and a FGF2, or any combination thereof.

In certain embodiments, the exosome further comprises VEGF. In certain embodiments, the exosome further comprises an HGF. In certain embodiments, the exosome further comprises a LIF. In certain embodiments, the exosome further comprises a G-CSF. In certain embodiments, the exosome further comprises a BDNF. In certain embodiments, the exosome further comprises a TSG-6. In certain embodiments, the exosome further comprises a BMP2. In certain embodiments, the exosome further comprises a FGF2.

In certain embodiments, the exosome further comprises one or more miRNA molecule selected from the group consisting of miRNA (miR)-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, miR-4324, and any combination thereof.

In certain embodiments, the exosome further comprises miR-3663-3p. In certain embodiments, the exosome further comprises miR-132-3p. In certain embodiments, the exosome further comprises miR-150-3p. In certain embodiments, the exosome further comprises miR-762. In certain embodiments, the exosome further comprises miR-4327. In certain embodiments, the exosome further comprises miR-3665. In certain embodiments, the exosome further comprises miR-34a-5p. In certain embodiments, the exosome further comprises miR-1915. In certain embodiments, the exosome further comprises miR-34a-39. In certain embodiments, the exosome further comprises miR-34b-5p. In certain embodiments, the exosome further comprises miR-874. In certain embodiments, the exosome further comprises miR-4281. In certain embodiments, the exosome further comprises miR-1207-5p. In certain embodiments, the exosome further comprises miR-30b-5p. In certain embodiments, the exosome further comprises miR-29b-3p. In certain embodiments, the exosome further comprises miR-199b-5p. In certain embodiments, the exosome further comprises miR-30e-5p. In certain embodiments, the exosome further comprises miR-26a-5p. In certain embodiments, the exosome further comprises miR-4324.

In certain embodiments, the exosome is devoid of one or more miRNA molecule selected from the group consisting of miR-503, miR-3659, miR-3529-3p, miR-320b, miR-1275, miR-3132, miR-320a, miR-495, miR-181b-5p, miR-222-3p, miR-424-5p, miR-4284, miR-574-5p, miR-143-3p, miR-106a-5p, miR-455-3p, miR-20a-5p, miR-145-5p, miR-324-3p, miR-130b-3p, miR-1305, miR-140-3p, and any combination thereof.

In certain embodiments, the exosome is devoid of miR-503. In certain embodiments, the exosome is devoid of miR-3659. In certain embodiments, the exosome is devoid of miR-3529-3p. In certain embodiments, the exosome is devoid of miR-320b. In certain embodiments, the exosome is devoid of miR-1275. In certain embodiments, the exosome is devoid of miR-3132. In certain embodiments, the exosome is devoid of miR-320a. In certain embodiments, the exosome is devoid of miR-495. In certain embodiments, the exosome is devoid of miR-181b-5p. In certain embodiments, the exosome is devoid of miR-222-3p. In certain embodiments, the exosome is devoid of miR-424-5p. In certain embodiments, the exosome is devoid of miR-4284. In certain embodiments, the exosome is devoid of miR-574-5p. In certain embodiments, the exosome is devoid of miR-143-3p. In certain embodiments, the exosome is devoid of miR-106a-5p. In certain embodiments, the exosome is devoid of miR-455-3p. In certain embodiments, the exosome is devoid of miR-20a-5p. In certain embodiments, the exosome is devoid of miR-145-5p. In certain embodiments, the exosome is devoid of miR-324-3p. In certain embodiments, the exosome is devoid of miR-130b-3p. In certain embodiments, the exosome is devoid of miR-1305. In certain embodiments, the exosome is devoid of miR-140-3p.

The technology provided herein further provides, in another embodiment, a pharmaceutical composition comprising an isolated MSC-NTF exosomes a population as described above. In some embodiments, disclosed herein is a pharmaceutical composition comprising an isolated exosome population derived from differentiated MSC-neurotrophic factor (MSC-NTF) cells comprising an increased quantity of at least one cargo protein, wherein said cargo protein comprises a leukemia inhibitory factor (LIF) protein, a chemokine (C-X-C Motif) Ligand 1 (CXCL1) protein, an interleukin 13 (IL13) protein, an vascular endothelial growth factor A (VEGFA) protein, or a growth differentiation factor 15 (GDF15) protein, or any combination thereof, compared with the quantity of said at least one cargo protein in an isolated exosome population derived from control MSCs. In some embodiments, a pharmaceutical composition comprising an isolated exosome population derived from MSC-NTF cells comprising an increased quantity of at least 2 cargo protein, wherein said cargo protein comprises a leukemia inhibitory factor (LIF) protein, a chemokine (C-X-C Motif) Ligand 1 (CXCL1) protein, an interleukin 13 (IL13) protein, an vascular endothelial growth factor A (VEGFA) protein, or a growth differentiation factor 15 (GDF15) protein, or any combination thereof, compared with the quantity of said at least one cargo protein in an isolated exosome population derived from control MSCs. In some embodiments, a pharmaceutical composition comprising an isolated exosome population derived from MSC-NTF cells comprising an increased quantity of at least 3, 4, or 5 cargo protein, wherein said cargo protein comprises a leukemia inhibitory factor (LIF) protein, a chemokine (C-X-C Motif) Ligand 1 (CXCL1) protein, an interleukin 13 (IL13) protein, an vascular endothelial growth factor A (VEGFA) protein, or a growth differentiation factor 15 (GDF15) protein, or any combination thereof, compared with the quantity of said at least one cargo protein in an isolated exosome population derived from control MSCs. In some embodiments, a pharmaceutical composition comprising an isolated exosome population derived from MSC-NTF cells comprising an increased quantity of LIF protein, a CXCL1 protein, an IL13 protein, a VEGFA protein, and a GDF15 protein, compared with the quantity of said at least one cargo protein in an isolated exosome population derived from control MSCs.

In certain embodiments, the pharmaceutical composition is substantially devoid of intact cells, ruptured cells, intact cell organelles, and/or ruptured cell organelles. In certain embodiments, the pharmaceutical composition is devoid of intact cells, ruptured cells, intact cell organelles, and/or ruptured cell organelles. In certain embodiments, the pharmaceutical composition is devoid of intact cells. In certain embodiments, the pharmaceutical composition is devoid of ruptured cells. In certain embodiments, the pharmaceutical composition is devoid of intact cell organelles. In certain embodiments, the pharmaceutical composition is devoid of ruptured cell organelles. In certain embodiments, the pharmaceutical composition is devoid of intact cells, ruptured cells, intact cell organelles, and ruptured cell organelles.

The term "substantially devoid of" as used herein is understood by persons in the art as including "devoid of" and "containing trace amounts of".

In certain embodiments, the purity of the isolated exosome in the pharmaceutical composition is at least 50% by size. In certain embodiments, the purity of the isolated exosome in the pharmaceutical composition is at least 55% by size. In certain embodiments, the purity of the isolated exosome in the pharmaceutical composition is at least 60% by size. In certain embodiments, the purity of the isolated exosome in the pharmaceutical composition is at least 65% by size. In certain embodiments, the purity of the isolated exosome in the pharmaceutical composition is at least 70% by size. In certain embodiments, the purity of the isolated exosome in the pharmaceutical composition is at least 75% by size. In certain embodiments, the purity of the isolated exosome in the pharmaceutical composition is at least 80% by size. In certain embodiments, the purity of the isolated exosome in the pharmaceutical composition is at least 85% by size. In certain embodiments, the purity of the isolated exosome in the pharmaceutical composition is at least 90% by size. In certain embodiments, the purity of the isolated exosome in the pharmaceutical composition is at least 95% by size. In certain embodiments, the purity of the isolated exosome in the pharmaceutical composition is at least 99% by size. As a person of skill in the art would appreciate, purity by size can be determined in a variety of methods known in the art.

Methods of Producing Isolated MSC & MSC-NTF Exosomes

Methods of producing isolated modified MSC exosomes include isolation and purification of exosome derived from a single cell type such as MSCs or genetically modified MSCs.

Methods of producing isolated MSC-NTF exosome include isolation and purification of exosome derived from a single cell type such as MSC-NTFs or genetically modified MSC-NTFs, skilled artisan would appreciate the isolated exosomes encompass purified exosomes. In some embodiments, isolated exosomes comprise purified exosomes. In some embodiments, isolated exosomes comprise a composition comprising purified exosomes.

In some embodiments, an isolated exosome is one which is physically separated from its natural environment. An isolated exosome may be physically separated, in whole or in part, from tissue or cells with which it naturally exists, including MSCs or MSC-NTFs. In some embodiments, a composition of isolated exosomes may be free of cells such as MSCs or MSC-NTFs, or it may be free or substantially free of conditioned media.

In some embodiments, exosomes may be isolated from conditioned media from cultures of MSC-NTF cells. In some embodiments, exosomes may be isolated from conditioned media from cultures of MSCs. Methods of isolating and/or harvesting exosomes are well known in the art. Methods may include use of differential filtration, through nylon membrane filters of defined pore size. A first filtration though a large pore size will retain cellular fragments and debris. A subsequent filtration through a smaller pore size will retain exosomes and purify them from smaller size contaminants.

In some embodiments, a method of producing isolated exosomes produces exosome having a size between 30-300 nm. In some embodiments, exosomes produced are between 30-250 nm. In some embodiments, exosomes produced are between 30-200 nm. In some embodiments, exosomes produced are between 30-175 nm. In some embodiments, exosomes produced are between 30-150 nm. In some embodiments, exosomes produced are between 40-150 nm. In some embodiments, exosomes produced are between 50-150 nm. In some embodiments, exosomes produced are between 30-100 nm. In some embodiments, exosomes produced are between 100-150 nm.

In some embodiments, the exosomes are isolated from bone marrow MSCs, adipocyte MSCs, dental pulp MSCs, placenta MSCs, synovial membrane MSCs, peripheral blood MSCs, oral mucosa MSCs, periodontal ligament MSCs, endometrium MSCs, umbilical cord MSCs, or umbilical cord blood MSCs.

In some embodiments, the exosomes are isolated from bone marrow MSC-NTFs, adipocyte MSC-NTFs, dental pulp MSC-NTFs, placenta MSC-NTFs, synovial membrane MSC-NTFs, peripheral blood MSC-NTFs, oral mucosa MSC-NTFs, periodontal ligament MSC-NTFs, endometrium MSC-NTFs, umbilical cord MSC-NTFs, or umbilical cord blood MSC-NTFs.

Example 4 below clearly shows production of isolated exosomes from MSC-NTF wherein the cargo between the two exosomes population differs. In some embodiments, methods producing an isolated exosome population from MSC-NTF cells, produces an isolated exosome population comprising increased quantity of at least one cargo protein compared with isolated exosomes produced from control MSC. In some embodiments, methods producing an isolated exosome population from MSC-NTF cells, produces an isolated exosome population comprising increased quantity of at least 2 cargo protein compared with isolated exosomes produced from control MSC. In some embodiments, methods producing an isolated exosome population from MSC-NTF cells, produces an isolated exosome population comprising increased quantity of at least 3, 4, or 5 cargo protein compared with isolated exosomes produced from control MSC.

In some embodiments, the MSCs are human MSCs. In some embodiments, the human MSCs are not genetically modified. In some embodiments, the human MSCs are genetically modified. In some embodiments, the MSCs were obtained from a healthy subject. In some embodiments, the differentiated MSC were obtained from a subject suffering from a neurodegenerative disease. In some embodiments, the neurodegenerative disease is selected from ALS, FTD, MSA, SMA, MS, PD. AD, Rett Syndrome, CP, ASD, and epilepsy.

In some embodiments, the MSC-NTFs are human MSC-NTFs. In some embodiments, the human MSC-NTFs are not genetically modified. In some embodiments, the human MSC-NTFs are genetically modified. In some embodiments, the differentiated MSCs were obtained from a healthy subject. In some embodiments, the differentiated MSCs were obtained from a subject suffering from a neurodegenerative disease. In some embodiments, the neurodegenerative disease is selected from ALS, FTD, MSA, SMA, MS, PD. AD, Rett Syndrome, CP, ASD, and epilepsy.

Methods known in the art include, but are not limited to, those described in US Publication No. 20170258840 (Examples section), Lamparski et al., J Immunol Methods. 2002; 270:211-226; U.S. Pat. No. 9,877,989 (Examples section), Corso et al., Sci Rep 7, 11561 (2017), and Lai et al., (2015) Semin Cell Dev Bio. 140:82-88.

Methods of isolating exosomes from MSCs conditioned media, may, in some embodiments, comprise a step of providing a sample comprising the MSC cells conditioned mediaconditioned media. In some embodiments, the MSCs used in the methods of isolation disclosed herein include a genetically modified MSC cell as described herein. In some embodiments, the MSCs are not genetically modified. In some embodiments, the MSCs are genetically modified to expression or highly express or highly express a growth factor, an miRNA, or an siRNA, or a combination thereof, as has been disclosed herein.

Once the MSCs conditioned media conditioned mediasample is provided, methods of isolating exosomes comprise a further step of isolating a fraction enriched with exosomes from the MSCs (purified exosomes). In some embodiments, a purified fraction of exosome is isolated from MSCs conditioned mediaconditioned media. In some embodiments, a purified fraction of exosome is isolated from MSCs conditioned media conditioned mediafrom which cell debris and large vesicles have been removed, e.g. by filtration. In some embodiments, a cell conditioned media conditioned mediais filtered through a 0.22 μm filter. Further filtration may, in some embodiments, comprise use of tangential flow filtration (TFF). The collected filtrate comprises a purified fraction of exosomes.

In some embodiments, the purified fraction of exosomes is analyzed for MSC markers.

Methods of isolating exosomes from MSC-NTFS, may, in some embodiments, comprise a step of providing a sample comprising the differentiated MSC cells. In some embodiments, the differentiated MSC cells (MSC-NTFs) used in the methods of isolation disclosed herein include all differentiated MSC-NTFs described herein. In some embodiments, the MSC-NTFs are not genetically modified. In some embodiments, the MSC-NTFs are genetically modified to express or highly express a growth factor, a galectin-1 molecule, an miRNA, or an siRNA, as has been disclosed herein.

Once the MSC-NTF conditioned media conditioned mediasample is provided, methods of isolating exosomes comprise a further step of isolating a fraction enriched with exosomes from the MSC-NTFs (purified exosomes). In some embodiments, a purified fraction of exosome is isolated from MSC-NTFs conditioned mediaconditioned media. In some embodiments, a purified fraction of exosome is isolated from MSC-NTFs conditioned media from which cell debris and large vesicles have been removed, e.g. by filtration. In some embodiments, a cell conditioned media is filtered through a 0.22 μm filter. Further filtration may in some embodiments, comprise use of tangential flow filtration (TFF). The collected filtrate comprises a purified fraction of exosomes.

In some embodiments, the purified fraction of exosomes is analyzed for MSC markers. In some embodiments, the purified fraction of exosomes is analyzed for MSC-NTF markers. NTF molecules expressed in MSC-NTF cells have been described in detail above. Any combination of these NTFs may be present in the purified fraction of exosomes. In some embodiments, the purified fraction of exosomes comprises, for example, but not limited to, any one of VEGF, HGF, LIF, G-CSF, BDNF, TSG-6, BMP2, or FGF2 or any combination thereof. In some embodiments, methods disclosed herein to produce an isolated MSC-NTF population of exosomes produces exosomes comprising an increased quantity of at least 2, 3, 4, 5, 6, 7, 8, 9, or 10 NTF. In some embodiments, methods disclosed herein to produce an isolated MSC-NTF population of exosomes produces exosomes comprising an increased quantity of at least 1 NTF. In some embodiments, methods disclosed herein to produce an isolated MSC-NTF population of exosomes produces exosomes comprising an increased quantity of at least 2 NTF. In some embodiments, methods disclosed herein to produce an isolated MSC-NTF population of exosomes produces exosomes comprising an increased quantity of at least 3 NTF.

In some embodiments, methods disclosed herein to produce an isolated MSC-NTF population of exosomes produces exosomes comprising an increased quantity of an NTF cargo protein comprising any NTF disclosed herein. In some embodiments, methods disclosed herein to produce an isolated MSC-NTF population of exosomes produces exosomes comprising an increased quantity of an NTF cargo protein comprising an LIF, a VEGFA, or a GDF15, or any combination thereof. In some embodiments, methods disclosed herein to produce an isolated MSC-NTF population of exosomes produces exosomes comprising an increased quantity of an NTF cargo protein comprising an LIF and a VEGFA. In some embodiments, methods disclosed herein to produce an isolated MSC-NTF population of exosomes produces exosomes comprising an increased quantity of an NTF cargo protein comprising an LIF and a GDF15. In some embodiments, methods disclosed herein to produce an isolated MSC-NTF population of exosomes produces exosomes comprising an increased quantity of an NTF cargo protein comprising VEGFA and a GDF15. In some embodiments, methods disclosed herein to produce an isolated MSC-NTF population of exosomes produces exosomes comprising an increased quantity of an NTF cargo protein comprising an LIF, a VEGFA, and a GDF15.

In some embodiments, additional cargo proteins may be increased in exosome population isolated from MSC-NTF cells using the methods described herein. For example, but not limited to, any of proteins IL36A, CCL7, MMP10, PIFG, CXCL8, LTA, LIF, CXCL1, CXCL6, MMP3, CHI3L1, IL11, FGF2, CXCL5, GAS1, JAML, TGFBR3, MEPE, IL6, PDGFA, CCL4, CCL21, IL13, VEGFA, CCL2, MIF, GDF15, PLAU, ANGPTL4, CTSB, BSG, CCL5, TPO, IL23, IL1RL1, SPP1, F11R, INHBA, and FAP, or any combination thereof. In some embodiments, additional cargo proteins may be increased in exosome population isolated from MSC-NTF cells using the methods described herein comprise an CXCL1 protein, or an IL13 protein. In some embodiments, additional cargo proteins may be increased in exosome population isolated from MSC-NTF cells using the methods described herein comprise an CXCL1 protein, and an IL13 protein.

In some embodiments, methods of producing MSC-NTF exosomes with an increased quantity of a cargo protein comprises a 2-fold-increase compared with isolated exosomes from control MSC cells. In some embodiments, an increased quantity of a cargo protein comprises a 3, 4, 5, 6, 7, 8, 9, 10, 11, 12, 13, 14, 15, 16, 17, 18, 19, 20, 21, 22, 23, 24, 25, 26, 27, 28, 29, or 30 fold-increase compared with isolated exosomes from control MSC cells. In some embodiments, methods of producing MSC-NTF exosomes with an increased quantity of a cargo protein comprises an increased quantity of a cargo protein comprises at least a 2-fold-increase compared with isolated exosomes from control MSC cells. In some embodiments, methods of producing MSC-NTF exosomes with an increased quantity of a cargo protein comprises an increased quantity of a cargo protein comprises at least a 3, 4, 5, 6, 7, 8, 9, 10, 11, 12, 13, 14, 15, 16, 17, 18, 19, 20, 21, 22, 23, 24, 25, 26, 27, 28, 29, or 30 fold-increase compared with isolated exosomes from control MSC cells. In some embodiments, methods of producing MSC-NTF exosomes with an increased quantity of a cargo protein comprises an increased quantity of a cargo protein comprises greater than a 30-fold-increase compared with isolated exosomes from control MSC cells. In some embodiments, methods of producing MSC-NTF exosomes with an increased quantity of a cargo protein comprises an increased quantity of a cargo protein comprises a 30, 31, 32, 33, 34, 35, 36, 37, 38, 39, 40, 41, 42, 43, 44, 45, 46, 47, 48, 49, or 50-fold-increase compared with isolated exosomes from control MSC cells. In some embodiments, methods of producing MSC-NTF exosomes with an increased quantity of a cargo protein comprises an increased quantity of a cargo protein comprises at least a 30, 31, 32, 33, 34, 35, 36, 37, 38, 39, 40, 41, 42, 43, 44, 45, 46, 47, 48, 49, or 50 fold-increase compared with isolated exosomes from control MSC cells.

In some embodiments, the purified fraction is analyzed for any one of the following markers: CD44, CD73, CD90, CD105, or a combination thereof, wherein these markers are present on MSCs and MSC-NTFs. In some embodiments, the purified fraction of exosomes is analyzed for a growth factor, a galectin-1 molecule, an miRNA, or an siRNA, or a combination thereof, wherein said MSC-NTFs were genetically modified to comprise the growth factor, an miRNA, an siRNA, or a nucleotide encoding a growth factor. In some embodiments, the purified fraction of exosomes is analyzed for a growth factor, a galectin-1 molecule, an miRNA, an siRNA, or any combination thereof, wherein said MSCs were genetically modified to comprise the growth factor, a galectin-1 molecule, an miRNA, an siRNA, or a combination thereof. In some embodiments, the purified fraction of exosome is analyzed for an exosome marker. In some embodiments, the purified fraction of exosome is analyzed for any one of exosome markers comprising (CD)9, CD63, CD9, CD61, CD81, ALIX, or tumor susceptibility gene (TSG)101, or a combination thereof.

In some embodiments, the purified fraction of exosome does not include markers not found on MSCs or MSC-NTFs. For example, in some embodiments, the purified fraction of exosomes does not include one or more of calnexin, CD34, CD45, CD19, CD5, CD20, CD11B, CD3, CD14, HLA-DR, and FMC7, or any combination thereof.

The miRNA that are present in increased amounts in MSC-NTF cells are described in detail above. The purified fraction of exosomes may include any combination of these miRNA, for example, but not limited to, miRNA selected from the group comprising miRNA (miR)-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, or miR-4324, or any combination thereof.

The miRNA that are present in decreased amounts in MSC-NTF cells are described in detail above. The purified fraction of exosomes may include any combination of these miRNA, for example, but not limited to, miRNA selected from the group comprising miRNA (miR)-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, or miR-4324, or any combination thereof.

In some embodiments, the purified fraction of exosomes comprises an increased amount of at least one miRNA and a decreased amount of at least one miRNA.

In some embodiments, a method of producing isolated modified MSC exosomes comprises a further step of collecting an exosome purified fraction comprising at least one exosome specific marker and at least one MSCs specific marker. In some embodiments, a method of producing isolated MSC-NTF exosomes comprises a further step of collecting an exosome purified fraction comprising at least one exosome specific marker and at least one MSC-NTFs specific marker.

In some embodiments, a method of producing a MSC-NTF cell-type specific exosome comprises providing a sample comprising differentiated MSCs that have been induced to secrete at least one neurotrophic factor (NTF) (labeled "MSC-NTF cells"), wherein the basal secretion of said at least one NTF is greater in said MSC-NTF cells compared with the basal secretion of said at least one NTF in a non-differentiated MSC; isolating an exosome purified fraction from said MSC-NTFs, wherein said exosome purified fraction comprises purified exosomes, and said purified exosomes are analyzed for at least one exosome specific marker, or for at least one MSC-NTF specific marker, or a combination thereof; and collecting the exosome purified fraction comprising the at least one exosome specific marker and the at least one MSC-NTF specific marker; thereby producing a MSC-NTF cell-type specific exosome.

In some embodiments, following collection of the exosome purified fraction, in vitro methods are used to load the exosomes with exogenous compounds, for example a growth factor, a galectin-1 molecule, a miRNA, an siRNA, or a combination thereof, as has been described herein in detail above.

In some embodiments, the exosomes of the purified fraction are loaded with a growth factor. In some embodiments, the exosomes of the purified fraction are loaded with IGF-1. In some embodiments the exosomes of the purified fraction are loaded with IGF-2. In some embodiments the exosomes of the purified fraction are loaded with GDF-5. In some embodiments, the methods of producing an MSC-NTF exosome comprise loading the purified fraction of exosomes with an IGF-1, an IGF-2, a GDF-5, or any combination thereof.

In some embodiments, the exosomes of the purified fraction are loaded with a galectin-1 molecule. In some embodiments, the modified MSC exosomes of the purified fraction are loaded with a galectin-1 molecule. In some embodiments, the MSC-NTF exosomes of the purified fraction are loaded with a galectin-1 molecule. In some embodiments, the methods of producing an MSC-NTF exosome comprise loading the purified fraction of exosomes with a galectin-1 molecule. In some embodiments, the methods of producing a modified MSC exosome comprise loading the purified fraction of exosomes with a galectin-1 molecule.

Thus, as disclosed herein, isolated exosome, may, in some embodiments, comprise any of NTF, a nucleic acid encoding an NTF, a growth factor, a galectin-1, miRNA, and siRNA, or any combination thereof, present in the MSC or MSC-NTF cells from which they were isolated. In some embodiments, the isolated exosome may, in addition, comprise growth factors, a galectin-1 molecule, an miRNA, or an siRNA, or any combination thereof, that were later loaded into the exosomes or were present in the genetically modified MSCs or MSC-NTFs from which the exosomes where isolated.

In some embodiments the exosomes of the purified fraction are loaded with an siRNA. In some embodiments, the siRNA comprises an MMP-9 siRNA or a portion thereof.

In some embodiments the exosomes of the purified fraction are loaded with an miRNA. In some embodiments, the miRNA comprises an miR-7 miRNA.

The technology provided herein further provides, in another aspect, a method of producing an isolated exosome population derived from MSC-NTF cells, wherein said exosome population comprises an increased quantity of at least one protein, compared to exosomes derived from control MSC. Isolated MSC-NTF exosome populations have been described in detail above. In some embodiments, any of the MSC-NTF exosome populations described herein, may be produced using the methods of production described below and in the Examples.

The technology provides, in some embodiments a method of producing an isolated exosome population, the method comprising the steps of: obtaining human MSCs, isolating adherent mononuclear cells from the MSCs, culturing the adherent mononuclear cells with a serum free DMEM medium containing dibutyryl cyclic adenosine monophosphate, human basic fibroblast growth factor, human platelet-derived growth factor, and of human heregulin-β1, and isolating an exosome from the serum free DMEM medium.

In some embodiments, when MSC are produced and isolated from bone marrow, peripheral blood, umbilical cord, or umbilical cord blood, said step of obtaining comprises separating human mononuclear cells from said bone marrow or said blood samples, followed by a step comprising isolating adherent MSC from the mononuclear population. In some embodiments, when said MSC are produced and isolated from adipocyte, dental pulp, placenta, synovial membrane, oral mucosa, periodontal ligament, or endometrium tissue samples, the step of obtaining comprises obtaining the tissue and dissociating it using physical and enzymatic methods well known in the art, followed by isolating adherent MSC from the total cell population.

In some embodiments, the isolated exosome population produced comprises an increased quantity of an NTF compared to exosomes isolated from control MSC. In some embodiments, the isolated exosome population produced comprises an increased quantity of an NTF and at least another protein compared to exosomes isolated from control MSC. In some embodiments, the NTF comprises a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and FGF2, or any combination thereof. In some embodiments, the at least another proteins comprises an IL36A, a CCL7, a MMP10, a PIFG, a CXCL8, a LTA, a CXCL6, an MMP3, a CHI3L1, an IL11, a FGF2, a CXCL5, a GAS1, a JAML, a TGFBR3, a MEPE, a IL6, a PDGFA, a CCL4, a CCL21, a CCL2, a MIF, a PLAU, an ANGPTL4, a CTSB, a BSG, a CCL5, a TPO, a IL23, a IL1RL1, a SPP1, a F11R, an INHBA, a FAP, a SPINT2, a IL36G, a TNFRSF10B or a TNFSF14, or any combination thereof.

In some embodiments, the isolated exosome population produced comprises an increased quantity of LIF protein compared to exosomes isolated from control MSC. In some embodiments, the isolated exosome population produced comprises an increased quantity of VEGFA protein compared to exosomes isolated from control MSC. In some embodiments, the isolated exosome population produced comprises an increased quantity of GDF15 protein compared to exosomes isolated from control MSC. In some embodiments, the isolated exosome population produced comprises an increased quantity of LIF and VEGFA proteins compared to exosomes isolated from control MSC. In some embodiments, the isolated exosome population produced comprises an increased quantity of LIF and GDF15 proteins compared to exosomes isolated from control MSC. In some embodiments, the isolated exosome population produced comprises an increased quantity of VEGFA and GDF15 proteins compared to exosomes isolated from control MSC.

In some embodiments, the isolated exosome population produced comprises an increased quantity of an NTF and at least another protein compared to exosomes isolated from control MSC. In some embodiments, the isolated exosome population produced comprises an increased quantity of an NTF comprising LIF, or VEGFA, or GDF15 proteins, or any combination thereof and at least another protein compared to exosomes isolated from control MSC. In some embodiments, the isolated exosome population produced comprises an increased quantity of an NTF and at least another protein comprising IL13 or CXCL1, or any combination thereof, compared to exosomes isolated from control MSC. In some embodiments, the isolated exosome population produced comprises an increased quantity of an NTF comprising LIF, or VEGFA, or GDF15 proteins, or any combination thereof and at least another protein comprising IL13 or CXCL1, or any combination thereof, compared to exosomes isolated from control MSC.

In certain embodiments, step (a) comprises collecting bone marrow samples into Heparin containing tubes from the posterior iliac crest of healthy adult human donors by bone marrow aspiration. In certain embodiments, step (b) comprises propagating the adherent mononuclear cells in low glucose DMEM supplemented with 200 mM L-Glutamine, 100 mM Sodium Pyruvate, 2 IU/ml Heparin and 10% platelet lysate. In certain embodiments, step (b) comprises isolating mononuclear cells from the MSCs and isolating adherent cells from the mononuclear cells. In certain embodiments, the serum free DMEM medium contains 0.1 to 10 mM of dibutyryl cyclic adenosine monophosphate, 2 to 200 ng/mL of human basic fibroblast growth factor, 0.5 to 50 ng/mL of human platelet-derived growth factor, and 5 to 500 ng/mL of human heregulin-β1. In certain embodiments, the serum free DMEM medium contains 1 mM of dibutyryl cyclic adenosine monophosphate, 20 ng/mL of human basic fibroblast growth factor, 5 ng/mL of human platelet-derived growth factor, and 50 ng/mL of human heregulin-β1 (S2M).

In certain embodiments, step (d) is performed 1 to 10 days after step (c). In certain embodiments, step (d) is performed 1 day after step (c). In certain embodiments, step (d) is performed 2 days after step (c). In certain embodiments, step (d) is performed 3 days after step (c). In certain embodiments, step (d) is performed 4 days after step (c). In certain embodiments, step (d) is performed 5 days after step (c). In certain embodiments, step (d) is performed 6 days after step (c). In certain embodiments, step (d) is performed 7 days after step (c). In certain embodiments, step (d) is performed 8 days after step (c). In certain embodiments, step (d) is performed 9 days after step (c). In certain embodiments, step (d) is performed 10 days after step (c).

In certain embodiments, step (d) comprises isolating the exosome from the serum free DMEM medium by Tangential Flow Filtration (TFF). In certain embodiments, step (d) comprises Tangential Flow Filtration (TFF) and Size Exclusion Chromatography (SEC).

In certain embodiments, the method further comprises loading the adherent mononuclear cells of step (c) or the exosomes isolated in step (d) with one or more cargo molecules.

In certain embodiments, the cargo molecule is selected from the group consisting of a small interfering RNA (siRNA), a micro RNA (miRNA), a growth factor, a neurotropic factor, and any combination thereof.

In certain embodiments, the cargo molecule is a small interfering RNA (siRNA). In certain embodiments, the cargo molecule is a micro RNA (miRNA). In certain embodiments, the cargo molecule is a growth factor. In certain embodiments, the cargo molecule is a neurotropic factor.

In certain embodiments, the isolated exosome described above is obtainable by a method comprising obtaining human MSCs, isolating mononuclear cells from the MSCs, isolating adherent cells from the mononuclear cells, culturing the mononuclear cells with a serum free DMEM medium containing 1 mM of dibutyryl cyclic adenosine monophosphate, 20 ng/mL of human basic fibroblast growth factor, 5 ng/mL of human platelet-derived growth factor, and 50 ng/mL of human heregulin-β1 for three days, and isolating an exosome from the serum free DMEM medium.

In certain embodiments, the isolated exosome described above is obtained by a method comprising obtaining human MSCs, isolating mononuclear cells from the MSCs, isolating adherent cells from the mononuclear cells, culturing the mononuclear cells with a serum free DMEM medium containing 1 mM of dibutyryl cyclic adenosine monophosphate, 20 ng/mL of human basic fibroblast growth factor, 5 ng/mL of human platelet-derived growth factor, and 50 ng/mL of human heregulin-β1 for three days, and isolating an exosome from the serum free DMEM medium.

Methods of Treatment

In some embodiments, disclosed herein is a method of treating a neurodegenerative disease in a subject in need thereof, the method comprising administering to said subject a therapeutically effective amount of an isolated modified MSC exosome. In some embodiments, a method of treating a neurodegenerative disease comprises administering to a subject a therapeutic composition of an MSC-NTF isolated exosome population, wherein these MSC-NTF isolated exosome populations have been described above in detail. In some embodiments, disclosed herein is a method of treating a neurodegenerative disease in a subject in need thereof, the method comprising administering to said subject a therapeutically effective amount of an isolated cell-type specific exosome, wherein said cell-type comprises differentiated MSCs (MSC) that have been induced to secrete at least one neurotrophic factor (NTF), termed MSC-NTF cells. In some embodiments, the basal secretion of said at least one NTF is greater in said MSC-NTFs compared with the basal secretion of said at least one NTF in a non-differentiated MSCs.

In some embodiments, said isolated modified MSC exosomes may be used in combination with an additional treatment or therapy used for treating neurodegenerative diseases in a subject. In some embodiments, said isolated cell-type specific exosome may be used in combination with an additional treatment or therapy used for treating neurodegenerative diseases in a subject. In some embodiments, an additional treatment comprises administration of MSC cells. In some embodiments, an additional treatment comprises administration of MSC-NTF cells. In certain embodiments, any additional treatment comprising administration of cells comprises separate administration of exosomes and cells. In certain embodiments, separate administration of exosomes and cells includes being comprised in separate compositions, being administered in separate time points, being administered into separate locations, and any combination thereof.

A skilled artisan would appreciate that in one embodiment, the term "administrating" and its grammatical equivalents, e.g., administration, may be used interchangeable herein with the term "transplanting" having all the same meanings and qualities. In some embodiments, transplanting is performed by injecting a composition described herein into a subject in need. In some embodiments, transplanting is performed by injecting an isolated cell-type specific exosome described herein into a subject in need.

In another embodiment, the neurodegenerative disease comprises Amyotrophic Lateral Sclerosis (ALS). In another embodiment, the neurodegenerative disease comprises frontotemporal dementia (FTD). In another embodiment, the neurodegenerative disease comprises Parkinson's disease (PD). In another embodiment, the neurodegenerative disease comprises Multiple System Atrophy (MSA). In another embodiment, the neurodegenerative disease comprises Huntington's disease. In another embodiment, the neurodegenerative disease comprises Alzheimer's disease. In another embodiment, the neurodegenerative disease comprises Rett Syndrome. In another embodiment, the neurodegenerative disease comprises lysosomal storage diseases. In another embodiment, the neurodegenerative disease comprises "white matter disease" or glial/demyelination disease, including Sanfilippo. In another embodiment, the neurodegenerative disease comprises Gaucher disease. In another embodiment, the neurodegenerative disease comprises Tay Sachs disease (beta hexosaminidase deficiency). In another embodiment, the neurodegenerative disease comprises multiple sclerosis (MS). In another embodiment, the neurodegenerative disease comprises neuromyelitis optica (NMO). In another embodiment, the neurodegenerative disease comprises NMO spectrum disease. In another embodiment, the neurodegenerative disease comprises brain injury or trauma caused by ischemia, accidents, or environmental insult. In another embodiment, the neurodegenerative disorder comprises stroke. In another embodiment, the neurodegenerative disorder comprises cerebral palsy (CP). In another embodiment, the neurodegenerative disease comprises autism or an autism spectrum disorder (ASD), or any combination thereof. In another embodiment, the neurodegenerative disease comprises spinal cord damage. In another embodiment, the neurodegenerative disease comprises ataxia. In another embodiment, the neurodegenerative disease comprises epilepsy.

In some embodiments, following administration of a purified exosome or composition thereof as described herein, a biological sample from the treated subject comprises increased levels of at least one neurotrophic factor compared with a biological sample from a control subject. In one embodiment, a control subject is a non-treated subject. In one embodiment, a control subject is subject receiving a placebo. In some embodiments, following administration of an isolated exosome or composition thereof as described herein, the biological sample comprises increased levels of at least one miRNA compared with a biological sample from a control subject. In some embodiments, a control biological sample comprises a sample obtained from a control subject receiving a placebo. In some embodiments, a biological sample comprises a sample obtained from the subject being treated, wherein the control biological sample was obtained prior to administration with an isolated exosome.

In some embodiments, the administration of purified exosomes or composition thereof, as described herein, results in an immunomodulatory effect in said subject. A skilled artisan would appreciate that the term "immunomodulatory effect" may encompass the modulation of the immune system in response to a stimulus, thus alleviating the detrimental effects of the disease. Thus, in some embodiments, treatment of a disease as disclosed herein comprises an immunomodulatory effect.

In some embodiments, an immunomodulatory effect comprises a decrease of CD4$^+$ T cell proliferation, or an induction of T-regulatory (T-reg) cells, or a decrease in IFN-gamma secretion, or a decrease in TNF alpha secretion, or a combination thereof.

Thus, in some embodiments, treatment of a neurodegenerative disease in a subject in need thereof, as disclosed herein, includes an immunomodulatory effect in the subject, for example but not limited to a decrease of CD4$^+$ T-cell proliferation, or an induction of T regulatory (T-reg) cells, or a decrease in IFN-gamma secretion, or a decrease in TNF alpha secretion, or a combination thereof.

In some embodiments, methods of administering purified exosomes or composition thereof provides an induction of regulatory T (T-reg) cells. In some embodiments, methods of administering purified exosomes or composition thereof provides decreased CD4$^+$ T-cell proliferation. In some embodiments, methods of administering purified exosomes or composition thereof provides decreased IFN-gamma secretion. In some embodiments, methods of administering purified exosomes or composition thereof provides decreased TNF-alpha secretion. In some embodiments, methods of administering purified exosomes or composition thereof provides a combination of immunomodulatory effects comprising an induction of regulatory T (T-reg) cells, a decrease of CD4$^+$ T-cell proliferation, a decrease of IFN-gamma secretion, or a decreased TNF-alpha secretion, or any combination thereof. In some embodiments, methods of administering purified exosomes or composition thereof provides a combination of immunomodulatory effects comprising an induction of regulatory T (T-reg) cells, a decrease of CD4$^+$ T-cell proliferation, a decrease of IFN-gamma secretion, and a decreased TNF-alpha secretion.

In some embodiments, biological samples comprises blood samples, serum samples, urine samples, or cerebrospinal fluid (CSF) samples. In some embodiments, an ex vivo control sample comprises MSC cells from the same subject that have not been induced to secrete increased levels of at least one NTF. In some embodiments, a control sample comprises isolated exosomes from non-differentiated MSC cells from the same subject that have not been induced to secrete increased levels of at least one NTF or have not been modified to comprise additional molecules.

A skilled artisan would appreciate that while isolated exosomes from MSCs and from MSC-NTFs may both contain the same at least one NTF, MSC-NTF cells have been induced to have increased secretion of an at least one NTF compared with the MSCs from which the MSC-NTF cells were derived. In some embodiments, an ex vivo control sample comprises undifferentiated MSCs from a subject to be treated. In some embodiments, a control sample is for ex-vivo analyses. In some embodiments, a control same is for in vivo analyses.

In some embodiments, an ex vivo control comprises isolated exosomes from MSC cells from the same donor/patient from which the modified MSC exosomes were derived, but no additional molecules have been loaded into said exosomes. In some embodiments, a control biological sample comprises isolated exosomes from MSC cells from the same donor/patient from which a genetically modified MSC was derived. In some embodiments, a control biological sample comprises isolated exosomes from MSC cells from the same donor/patient from which the MSC-NTF cells were derived. In some embodiments, a control biological sample comprises a sample obtained from a patient treated with an isolated exosome which was obtained prior to treatment. In some embodiments, a control sample comprises a sample from a non-treated patient. In some embodiments, a control sample comprises a sample from a patient treated with placebo.

In another embodiment, following said administration, a biological sample comprises increased levels of at least one neurotrophic factor (NTF). In some embodiments, said NTF is selected from the group comprising a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and FGF2, or any combination thereof.

In one embodiment, following said administration, a biological sample comprises decreased levels of at least one inflammatory factor or pro-apoptotic factor or factor that influence inflammatory factors, compared with a biological sample from a control subject. In another embodiment, the inflammatory factor or pro-apoptotic factor or factor that influence inflammatory factors is selected from the group comprising a Chitotriosidase 1 (CHIT1), a C-reactive protein (CRP), a monocyte chemotactic protein 1 (MCPJ), a stromal derived factor 1 (SDF-1), Macrophage Inflammatory protein (MIP-1), or a caspase 3 (CASP3), or any combination thereof. In another embodiment, following said administration, said biological sample comprises increased levels of at least one neurotrophic factor and decreased levels of at least one inflammatory factor or pro-apoptotic factor or factor that influence inflammatory factors compared with a biological sample from a control subject.

In some embodiments, an isolated modified MSC exosome or a composition thereof may be administered via any suitable method known to one of skilled in the art. In some embodiments, an isolated cell-type specific exosome or a composition thereof may be administered via any suitable method known to one of skilled in the art. Examples of such method include, but are not limited to, intrathecal, intramuscular, intradermal, intraperitoneal, intravenous, subcutaneous, and/oral routes. Administration may also include systemic or local administration of the composition disclosed herein.

The administration may also encompass surgically administering, implanting, inserting, or injecting the isolated modified MSC exosomes or the isolated cell-type specific exosomes, into a subject. The isolated modified MSC exosomes or the isolated cell-type specific exosomes can be located intrathecally, subcutaneously, intramuscularly, in the central nervous system (CNS), or located at another body location, which allow the exosomes to perform their intended function. Suitable sites for administration may be readily determined by a medical professional.

In one embodiment, the isolated modified MSC exosomes or the isolated cell-type specific exosomes (MSC-NTF exosomes) are administered intrathecally into the CSF of the subject. In another embodiment, the isolated modified MSC exosomes or the isolated cell-type specific exosomes are administered into a muscle of the subject. In a further embodiment, administration comprises administering to the cerebrospinal fluid of the subject. In still a further embodiment, administration comprises administering to the central nervous system of the subject. In another embodiment, administration comprises administering to the cerebrospinal fluid or the central nervous system, or any combination thereof, of the subject.

In some embodiments, administration to the CSF or CNS of the subject comprises administration of a therapeutically effective dose of purified modified MSC exosomes or purified MSC-NTF exosomes or a composition thereof.

A skilled artisan would appreciate that the term "central nervous system" may encompass the brain and the spinal cord. In some embodiments, administration comprises administering to the brain. In some embodiments, administration comprises administering to the spinal cord. In some embodiments, administration comprises administering to the brain and to the spinal cord.

In one embodiment, administration comprises intramuscular (IM) injection, or intrathecal (IT) injection, or intravenous (IV) injection, or a combination thereof.

In another embodiment, IM administration comprises multiple injections at the same time point. One skilled in the art would appreciate that multiple injections at the same time point may encompass injections given one following the other at a given time point. In another embodiment, IM administration comprises about 20 injections. In another embodiment, IM administration comprises about 21 injections. In another embodiment, IM administration comprises about 22 injections. In another embodiment, IM administration comprises about 23 injections. In another embodiment, IM administration comprises about 24 injections. In another embodiment, IM administration comprises about 25 injections. In another embodiment, IM administration comprises about 26 injections. In another embodiment, IM administration comprises about 27 injections. In another embodiment, IM administration comprises about 28 injections. In another embodiment, IM administration comprises about 29 injections. In another embodiment, IM administration comprises about 30 injections.

In some embodiments, administration comprises a therapeutically effective number of time points. In some embodiments, injections are administered every month. In some embodiments, injections are administered every two months. In some embodiments, injections are administered every three months. In some embodiments, injections are administered as needed. In some embodiments, multiple injections are provided at each administration. In some embodiment, 2-30 injections are provided at each administration. In some embodiment, 2-20 injections are provided at each administration. In some embodiment, 20-30 injections are provided at each administration. In some embodiment, 10-20 injections are provided at each administration. In some embodiment, 2, 3, 4, 5, 6, 7, 8, 9, 10, 11, 12, 13, 14, 15, 16, 17, 18, 19, 20, 21, 22, 23, 24, 25, 26, 27, 28, 29, or 30 injections are provided at each administration.

In one embodiment, an IT injection or IM injection comprises a therapeutically effective dose of isolated cell-type specific exosomes.

In one embodiment, administration comprises a single time point. One skilled in the art would appreciate that treatment may encompass follow-up administration of isolated modified MSC exosomes or isolated cell-type specific exosomes as described herein. In another embodiment, administration comprises at least two time points. In another embodiment, administration comprises two time points. The timing of administration of a second or further time point, may encompass analysis of biological samples taken from a subject and analyzed for NTF and/or inflammatory factors, as described herein. In some embodiment, administration comprising as many time points as necessary for therapeutic efficacy. In some embodiments, therapeutic efficacy may be determined based on analysis of secretion of at least one NTF and/or and at least one inflammatory factor or pro-apoptotic factor or factor that influence inflammatory factors, as described in detail herein.

In another embodiment, follow-up administration enhances the treatment of the neurodegenerative disease. In another embodiment, a repeat dose comprises a second administration at about 8 to 12 weeks following the initial treatment. In another embodiment, a repeat dose comprises a second administration at about 7 weeks. In another embodiment, a repeat dose comprises a second administration at about 8 weeks. In another embodiment, a repeat dose comprises a second administration at about 9 weeks. In another embodiment, a repeat dose comprises a second administration at about 10 weeks. In another embodiment, a repeat dose comprises a second administration at about 11 weeks. In another embodiment, a repeat dose comprises a second administration at about 12 weeks. In another embodiment, a repeat dose comprises a second administration at about 13 weeks. In another embodiment, a repeat dose comprises a second administration at about 14 weeks. In another embodiment, administration comprises repeat administrations at about at least three-time points. In another embodiment, administration comprises repeat administrations at about at least four-time points. In another embodiment, administration comprises repeat administrations at about at least five-time points. In another embodiment, administration comprises repeat administrations at more than 5 time points. In another embodiment, administration comprises repeat administrations at more than 10 time points. In another embodiment, administration comprises a repeat dose at follow-up time points for a duration of a disease or disorder.

The neurodegenerative disease or condition treated by the methods of use described herein, have been described above. In one embodiment, a neurodegenerative disease or condition treated by the methods of use described herein include, but is not limited to ALS, FTD, PD, MSA, SMA, MS, AD, Rett Syndrome, CP, ASD, and epilepsy.

In some embodiments, exosomes used in the treatment of ALS comprise an increased amount of IGF-1, IGF-2, a galectin-1 molecule, or an MMP-9 siRNA, or any combination thereof.

In some embodiments, treatment of a neurodegenerative disease or condition comprises use of an isolated modified MSC exosome comprising an MMP-9 targeted siRNA. In some embodiments, treatment of a neurodegenerative disease or condition comprises use of an isolated modified MSC exosome comprising an miR-7. In some embodiments, treatment of a neurodegenerative disease or condition comprises use of an isolated modified MSC exosome comprising IGF-1 or an IGF-2 or a galectin-1, or a combination thereof.

In some embodiments, treatment of a neurodegenerative disease or condition comprises use of an isolated MSC-NTF exosome comprising an MMP-9 targeted siRNA. In some embodiments, treatment of a neurodegenerative disease or condition comprises use of an isolated MSC-NTF exosome comprising a miR-7. In some embodiments, treatment of a neurodegenerative disease or condition comprises use of an isolated MSC-NTF exosome comprising IGF-1 or an IGF-2 or a galectin-1 molecule, or a combination thereof.

In some embodiments, exosomes used in the treatment of PD comprise an increased amount of GDF-5, a galectin-1 molecule, an miR-7, or an MMP-9 siRNA, or any combination thereof.

In some embodiments, the method comprises a step of detecting a biomarker associated with ALS, or a biomarker that identifies progression of ALS, or a combination thereof. In some embodiments, a biomarker associated with ALS is selected from the group comprising CHIT1, MCP-1, VEGF, HGF, LIF, miR19, miR146a, miR-34a, miR-376-a, or miR-132, or any combination thereof.

In some embodiments, general inflammatory markers are used to identify progression of neurodegenerative disease. In some embodiments, neuroinflammatory markers are used to identify progression of neurodegenerative disease. In some embodiments, general inflammatory markers are used to identify progression neurodegenerative diseases including any of [001] ALS, FTD, MSA, SMA, MS, PD, AD, Rett Syndrome, CP, ASD, and epilepsy. In some embodiments, neuroinflammatory markers are used to identify progression neurodegenerative diseases including any of ALS, FTD, MSA, SMA, MS, PD, AD, Rett Syndrome, CP, ASD, and epilepsy. In some embodiments, at least one general inflammatory marker is modulated in a neurodegenerative disease. In some embodiments, at least one general inflammatory marker is modulated in any of ALS, FTD, MSA, SMA, MS, PD, AD, Rett Syndrome, CP, ASD, and epilepsy. In some embodiments, at least one neuroinflammatory marker is modulated in a neurodegenerative disease. In some embodiments, at least one neuroinflammatory marker is modulated in any of ALS, FTD, MSA, SMA, MS, PD, AD, Rett Syndrome, CP, ASD, and epilepsy.

In some embodiments, a general inflammatory marker that is modulated in a neurodegenerative disease comprises a MHCII, a IBA-1, or CD163, or any combination thereof. In some embodiments, a general inflammatory marker selected from MHCII, IBA-1, and CD163, or a combination thereof, is modulated in ALS, FTD, MSA, SMA, MS, PD, AD, Rett Syndrome, CP, ASD, and epilepsy.

In some embodiments, a general inflammatory marker selected from MHCII, IBA-1, and CD163, or a combination thereof, is used to identify progression of a neurodegenerative disease, including ALS, FTD, MSA, SMA, MS, PD, AD, Rett Syndrome, CP, ASD, and epilepsy.

In some embodiments, methods of modulating a neurotrophic factor or an inflammatory factor or a pro-apoptotic factor or a factor that influence inflammatory factors in a subject, as described herein comprise administration of a therapeutically effective amount of an exosome or composition thereof as described herein, where the administration provides an immunomodulatory effect to the subject.

In some embodiments, an immunomodulatory effect comprises a decrease of $CD4^+$ T-cell proliferation, or an induction of T-regulatory (T-reg) cells, or a decrease in IFN-gamma secretion, or a decrease in TNF alpha secretion, or a combination thereof.

Thus, in some embodiments, methods of modulating a neurotrophic factor or an inflammatory factor or a pro-apoptotic factor or a factor that influences inflammatory factors in a subject in need thereof, as disclosed herein, includes providing an immunomodulatory effect in the subject, for example but not limited to a decrease of $CD4^+$ T-cell proliferation, or an induction of T-regulatory (T-reg) cells, or a decrease in IFN-gamma secretion, or a decrease in TNF alpha secretion, or a combination thereof.

In some embodiments, methods of administering purified exosomes or composition thereof provides an induction of regulatory T (T-reg) cells. In some embodiments, methods of administering purified exosomes or composition thereof provides decreased $CD4^+$ T-cell proliferation. In some embodiments, methods of administering purified exosomes or composition thereof provides decreased IFN-gamma secretion. In some embodiments, methods of administering purified exosomes or composition thereof provides decreased TNF-alpha secretion. In some embodiments, methods of administering purified exosomes or composition thereof provides a combination of immunomodulatory effects comprising an induction of regulatory T (T-reg) cells, a decrease of $CD4^+$ T-cell proliferation, a decrease of IFN-gamma secretion, or a decreased TNF-alpha secretion, or any combination thereof. In some embodiments, methods of administering purified exosomes or composition thereof provides a combination of immunomodulatory effects comprising an induction of regulatory T (T-reg) cells, a decrease of $CD4^+$ T-cell proliferation, a decrease of IFN-gamma secretion, and a decreased TNF-alpha secretion.

Neuroinflammatory disorders represent a broad spectrum of diverse disorders including encephalitis (infectious and autoimmune), demyelinating disorders, immune-mediated movement disorders, genetic autoinflammatory CNS disorders, vasculitis, and other miscellaneous disorders. Markers of neuroinflammatory disorders (neuroinflammatory biomarkers) include but are not limited to sCD27 receptor, chitinase 3-like-1 protein, and chitinase 3-like-2 protein. A skilled artisan would recognize that the term "chitinase 3-like-1 protein" may be used interchangeable with "YKL-40" or a "polypeptide expressed from CHI3L1", having all the same meanings and qualities.

In some embodiments, detecting a general inflammatory biomarker or a neuroinflammatory biomarker, or a combination thereof, measures whether administration of said isolated cell-type specific exosome reduces inflammation. In some embodiments, detecting a general inflammatory biomarker or a neuroinflammatory biomarker, or a combination thereof, measures whether administration of said isolated cell-type specific exosome reduces the number of α-synuclein inclusions in the cortex, or hippocampus, or amygdala, or a combination thereof. In some embodiments, detecting a general inflammatory biomarker or a neuroinflammatory biomarker, or a combination thereof, measures whether administration of said isolated cell-type specific exosome reduces development of α-synuclein inclusion-induced behavior defects. In some embodiments, detecting a general inflammatory biomarker or a neuroinflammatory biomarker, or a combination thereof, measures whether administration of said isolated modified MSC exosomes or isolated cell-type specific exosome alters the loss of dopaminergic terminals in TH+ and Nissl+ neurons.

In some embodiments, provided herein is a method for modulating a neurotrophic or an inflammatory factor or a pro-apoptotic factor or a factor that influence inflammatory factors in a subject, the method comprising administering to said subject a therapeutically effective amount of an isolated modified MSC exosome.

In some embodiments, provided herein is a method for modulating a neurotrophic or an inflammatory factor or a pro-apoptotic factor or a factor that influence inflammatory factors in a subject, the method comprising administering to said subject a therapeutically effective amount of an isolated cell-type specific exosome, wherein said cell-type comprises differentiated MSCs that have been induced to secrete at least one neurotrophic factor (NTF), MSC-NTF cells, wherein a basal secretion of said at least one NTF is greater in said MSC-NTF compared with a basal secretion of said at least one NTF in a non-differentiated MSC.

As used herein, the terms "treat" and "treatment" may encompass therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

The technology provided herein further provides, in another aspect, a method of treating a neurodegenerative disease in a subject in need thereof, the method comprising the step of administering to the subject a pharmaceutical composition comprising a therapeutically effective amount of an isolated exosome population derived from MSC NTF cells, as described in detail above.

In some embodiments, the isolated exosome population administered in a method of treating a neurodegenerative disease comprises an increased quantity of an NTF compared to exosomes isolated from control MSC. In some embodiments, the isolated exosome population administered in a method of treating a neurodegenerative disease comprises an increased quantity of an NTF and at least another protein compared to exosomes isolated from control MSC. In some embodiments, the NTF comprises a vascular endothelial growth factor (VEGF), a hepatocyte growth factor (HGF), a leukemia inhibitory factor (LIF), a glial derived neurotrophic factor (GDNF), a neurotrophin-3 (NT-3), a neurotrophin-4/5, a Neurturin (NTN), a Neurotrophin-4, a Persephin, artemin (ART), a ciliary neurotrophic factor (CNTF), an insulin growth factor-I (IGF-1), Growth and differentiation Factor (GDF-15), Granulocyte Stimulating factor (G-CSF), a Brain-derived neurotrophic factor (BDNF), a Tumor necrosis factor-inducible gene 6 protein (TSG-6; also known as TNF-stimulated gene 6 protein), Bone morphogenetic protein 2 (BMP2), and Fibroblast Growth Factor 2 (FGF2). In some embodiments, the at least another proteins comprises an IL36A, a CCL7, a MMP10, a PIFG, a CXCL8, a LTA, a CXCL6, an MMP3, a CHI3L1, an IL11, a FGF2, a CXCL5, a GAS1, a JAML, a TGFBR3, a MEPE, a IL6, a PDGFA, a CCL4, a CCL21, a CCL2, a MIF, a PLAU, an ANGPTL4, a CTSB, a BSG, a CCL5, a TPO, a IL23, a IL1RL1, a SPP1, a F11R, an INHBA, a FAP, a SPINT2, a IL36G, a TNFRSF10B or a TNFSF14, or any combination thereof.

In some embodiments, the isolated exosome population administered in a method of treating a neurodegenerative disease comprises an increased quantity of LIF protein compared to exosomes isolated from control MSC. In some embodiments, the isolated exosome population administered in a method of treating a neurodegenerative disease comprises an increased quantity of VEGFA protein compared to exosomes isolated from control MSC. In some embodiments, the isolated exosome population administered in a method of treating a neurodegenerative disease comprises an increased quantity of GDF15 protein compared to exosomes isolated from control MSC. In some embodiments, the isolated exosome population administered in a method of treating a neurodegenerative disease comprises an increased quantity of LIF and VEGFA proteins compared to exosomes isolated from control MSC. In some embodiments, the isolated exosome population administered in a method of treating a neurodegenerative disease comprises an increased quantity of LIF and GDF15 proteins compared to exosomes isolated from control MSC. In some embodiments, the isolated exosome population administered in a method of treating a neurodegenerative disease comprises an increased quantity of VEGFA and GDF15 proteins compared to exosomes isolated from control MSC.

In some embodiments, the isolated exosome population administered in a method of treating a neurodegenerative disease comprises an increased quantity of an NTF and at least another protein compared to exosomes isolated from control MSC. In some embodiments, the isolated exosome population administered in a method of treating a neurodegenerative disease comprises an increased quantity of an NTF comprising LIF, or VEGFA, or GDF15 proteins, or any combination thereof and at least another protein compared to exosomes isolated from control MSC. In some embodiments, the isolated exosome population administered in a method of treating a neurodegenerative disease comprises an increased quantity of an NTF and at least another protein comprising IL13 or CXCL1, or any combination thereof, compared to exosomes isolated from control MSC. In some embodiments, the isolated exosome population administered in a method of treating a neurodegenerative disease comprises an increased quantity of an NTF comprising LIF, or VEGFA, or GDF15 proteins, or any combination thereof and at least another protein comprising IL13 or CXCL1, or any combination thereof, compared to exosomes isolated from control MSC.

Also provided herein, in some embodiments, is a pharmaceutical composition comprising a therapeutically effective amount of an isolated exosome population derived from MSC-NTF cells as described in detail above.

In some embodiments, the pharmaceutical composition comprises an isolated exosome population comprising an increased quantity of an NTF compared to exosomes isolated from control MSC. In some embodiments, the pharmaceutical composition comprises an isolated exosome population comprising an increased quantity of an NTF and at least another protein compared to exosomes isolated from control MSC. In some embodiments, the NTF comprises a vascular endothelial growth factor (VEGF), a hepatocyte growth factor (HGF), a leukemia inhibitory factor (LIF), a glial derived neurotrophic factor (GDNF), a neurotrophin-3 (NT-3), a neurotrophin-4/5, a Neurturin (NTN), a Neurotrophin-4, a Persephin, artemin (ART), a ciliary neurotrophic factor (CNTF), an insulin growth factor-I (IGF-1), Growth and differentiation Factor (GDF-15), Granulocyte Stimulating factor (G-CSF), a Brain-derived neurotrophic factor (BDNF), a Tumor necrosis factor-inducible gene 6 protein (TSG-6; also known as TNF-stimulated gene 6 protein), Bone morphogenetic protein 2 (BMP2), and Fibroblast Growth Factor 2 (FGF2). In some embodiments, the at least another proteins comprises an IL36A, a CCL7, a MMP10, a PIFG, a CXCL8, a LTA, a CXCL6, an MMP3, a CHI3L1, an IL11, a FGF2, a CXCL5, a GAS1, a JAML, a TGFBR3, a MEPE, a IL6, a PDGFA, a CCL4, a CCL21, a CCL2, a MIF, a PLAU, an ANGPTL4, a CTSB, a BSG, a CCL5, a TPO, a IL23, a IL1RL1, a SPP1, a F11R, an INHBA, a FAP, a SPINT2, a IL36G, a TNFRSF10B or a TNFSF14, or any combination thereof.

In some embodiments, the pharmaceutical composition comprises an isolated exosome population comprising an increased quantity of LIF protein compared to exosomes isolated from control MSC. In some embodiments, the pharmaceutical composition comprises an isolated exosome population comprising an increased quantity of VEGFA protein compared to exosomes isolated from control MSC. In some embodiments, the pharmaceutical composition comprises an isolated exosome population comprising an increased quantity of GDF15 protein compared to exosomes isolated from control MSC. In some embodiments, the pharmaceutical composition comprises an isolated exosome population comprising an increased quantity of LIF and VEGFA proteins compared to exosomes isolated from control MSC. In some embodiments, the pharmaceutical composition comprises an isolated exosome population comprising an increased quantity of LIF and GDF15 proteins compared to exosomes isolated from control MSC. In some embodiments, the pharmaceutical composition comprises an isolated exosome population comprising an increased quantity of VEGFA and GDF15 proteins compared to exosomes isolated from control MSC.

In some embodiments, the pharmaceutical composition comprises an isolated exosome population comprising an increased quantity of an NTF and at least another protein compared to exosomes isolated from control MSC. In some embodiments, the pharmaceutical composition comprises an isolated exosome population comprising an increased quantity of an NTF comprising LIF, or VEGFA, or GDF15 proteins, or any combination thereof and at least another protein compared to exosomes isolated from control MSC. In some embodiments, the pharmaceutical composition comprises an isolated exosome population comprising an increased quantity of an NTF and at least another protein comprising IL13 or CXCL1, or any combination thereof, compared to exosomes isolated from control MSC. In some embodiments, the pharmaceutical composition comprises an isolated exosome population comprising an increased quantity of an NTF comprising LIF, or VEGFA, or GDF15 proteins, or any combination thereof and at least another protein comprising IL13 or CXCL1, or any combination thereof, compared to exosomes isolated from control MSC.

The technology provided herein further provides, in another aspect, a method of increasing the level of a protein in a cell, the method comprising the step of contacting the cell with an isolated exosome comprising the protein, wherein the protein comprises an NTF. In some embodiments, the method comprises contacting a cell with an isolated exosome population comprising an increased quantity of an NTF compared with exosomes isolated from control MSC. In some embodiments, the method comprises contacting a cell with an isolated exosome population comprising an increased quantity of a combination of NTFs compared with exosomes isolated from control MSC. In some embodiments, the NTF comprises a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and FGF2, or any combination thereof. In some embodiments, the NTF comprises a combination of a LIF, a GDF15, and a VEGFA. In some embodiments, the NTF comprises a combination of a LIF and a VEGFA. In some embodiments, the NTF comprises a combination of a a GDF15, and a VEGFA.

In some embodiments, the method comprises contacting a cell with an isolated exosome population comprising an increased quantity of an NTF and at least another protein compared with exosomes isolated from control MSC. In some embodiments, the at least another proteins comprises an IL36A, a CCL7, a MMP10, a PIFG, a CXCL8, a LTA, a CXCL6, an MMP3, a CHI3L1, an IL11, a FGF2, a CXCL5, a GAS1, a JAML, a TGFBR3, a MEPE, a IL6, a PDGFA, a CCL4, a CCL21, a CCL2, a MIF, a PLAU, an ANGPTL4, a CTSB, a BSG, a CCL5, a TPO, a IL23, a IL1RL1, a SPP1, a F11R, an INHBA, a FAP, a SPINT2, a IL36G, a TNFRSF10B or a TNFSF14, or any combination thereof. In some embodiments, the NTF comprises a combination of a LIF, a GDF15, and a VEGFA. In some embodiments, the NTF comprises a combination of a LIF and a VEGFA. In some embodiments, the NTF comprises a combination of a GDF15, and a VEGFA. In some embodiments, the NTF comprises a combination of a LIF, a GDF15, and a VEGFA, and the at least another protein comprises an IL13 or a CXCL1 protein. In some embodiments, the NTF comprises a combination of a LIF, a GDF15, and a VEGFA, and the at least another protein comprises an IL13 and a CXCL1 protein. In some embodiments, the NTF comprises a combination of a LIF and a VEGFA, and the at least another protein comprises an IL13 or/and a CXCL1 protein. In some embodiments, the NTF comprises a combination of a GDF15, and a VEGFA and the at least another protein comprises an IL13 and/or a CXCL1 protein.

In certain embodiments, the cell is within a human body. In certain embodiments, the cell is ex-vivo.

In certain embodiments, the protein further comprises the protein TNFSF14. In certain embodiments, the protein further comprises the protein IL36A. In certain embodiments, the protein further comprises the protein CCL7. In certain embodiments, the protein further comprises the protein MMP10. In certain embodiments, the protein further comprises the protein PIFG. In certain embodiments, the protein further comprises the protein CXCL8. In certain embodiments, the protein further comprises the protein LTA. In certain embodiments, the protein further comprises the protein LIF. In certain embodiments, the protein further comprises the protein CXCL1. In certain embodiments, the protein further comprises the protein CXCL6. In certain embodiments, the protein further comprises the protein MMP3. In certain embodiments, the protein further comprises the protein CHI3L1. In certain embodiments, the protein further comprises the protein IL11. In certain embodiments, the protein further comprises the protein FGF2. In certain embodiments, the protein further comprises the protein CXCL5. In certain embodiments, the protein further comprises the protein GAS1. In certain embodiments, the protein further comprises the protein JAML. In certain embodiments, the protein further comprises the protein TGFBR3. In certain embodiments, the protein further comprises the protein MEPE. In certain embodiments, the protein further comprises the protein IL6. In certain embodiments, the protein further comprises the protein PDGFA. In certain embodiments, the protein further comprises the protein CCL4. In certain embodiments, the protein further comprises the protein CCL21. In certain embodiments, the protein further comprises the protein IL13. In certain embodiments, the protein further comprises the protein VEGFA. In certain embodiments, the protein further comprises the protein CCL2. In certain embodiments, the protein further comprises the protein MIF. In certain embodiments, the protein further comprises the protein GDF15. In certain embodiments, the protein further comprises the protein PLAU. In certain embodiments, the protein further comprises the protein ANGPTL4. In certain embodiments, the protein further comprises the protein CTSB. In certain embodiments, the protein further comprises the protein BSG. In certain embodiments, the protein further comprises the protein CCL5. In certain embodiments, the protein further comprises the protein TPO. In certain embodiments, the protein further comprises the protein IL23. In certain embodiments, the protein further comprises the protein IL1RL1. In certain embodiments, the protein further comprises the protein SPP1. In certain embodiments, the protein further comprises the protein F11R. In certain embodiments, the protein further comprises the protein INHBA. In certain embodiments, the protein further comprises the protein FAP. In certain embodiments, the protein further comprises the proteins IL36A, CCL7, MMP10, PIFG, CXCL8, LTA, LIF, CXCL1, CXCL6, MMP3, CHI3L1, IL11, FGF2, CXCL5, GAS1, JAML, TGFBR3, MEPE, IL6, PDGFA, CCL4, CCL21, IL13, VEGFA, CCL2, MIF, GDF15, PLAU, ANGPTL4, CTSB, BSG, CCL5, TPO, IL23, IL1RL1, SPP1, F11R, INHBA, and FAP.

The technology provided herein further provides, in another aspect, a method of modulating the expression level of a gene in a cell, the method comprising the step of contacting the cell with any isolated isolated exosome population as described herein above, wherein the gene of which the expression level is modulated is selected from the group consisting of ENSG00000204711, EN5G00000134668, ENSG00000175899, EN5G00000278910, ENSG00000131095, EN5G00000102359, ENSG00000261371, ENSG00000091583, EN5G00000197632, EN5G00000113263, EN5G00000250993, EN5G00000259070, ENSG00000117318, ENSG00000266928, ENSG00000196639, ENSG00000164850, ENSG00000188404, ENSG00000105825, ENSG00000198796, ENSG00000165899, ENSG00000204277, ENSG00000142748, ENSG00000248461, ENSG00000188501, ENSG00000250538, ENSG00000136869, ENSG00000125968, ENSG00000131094, ENSG00000105559, ENSG00000135547, ENSG00000140853, ENSG00000134531, ENSG00000108691, ENSG00000235884, ENSG00000205403, ENSG00000267280, ENSG00000165985, ENSG00000172548, ENSG00000257446, ENSG00000180801, ENSG00000138798, ENSG00000116745, ENSG00000107984, ENSG00000122585, ENSG00000128283, ENSG00000089327, ENSG00000139155, ENSG00000183691, ENSG00000147041, ENSG00000184557, ENSG00000121068, ENSG00000101825, ENSG00000137834, ENSG00000087510, ENSG00000185149, ENSG00000163251, ENSG00000153976, ENSG00000099860, ENSG00000106366, ENSG00000128342, ENSG00000164488, ENSG00000177337, ENSG00000262001, ENSG00000131203, ENSG00000138316, ENSG00000167306, ENSG00000131724, ENSG00000142089, ENSG00000222041, ENSG00000152049, ENSG00000172965, ENSG00000203805, ENSG00000154274, ENSG00000177359, ENSG00000145623, ENSG00000213694, ENSG00000078081, ENSG00000138496, ENSG00000105974, ENSG00000119917, ENSG00000262484, ENSG00000197847, ENSG00000203688, ENSG00000221818, ENSG00000279232, ENSG00000260941, ENSG00000251161, ENSG00000131480, ENSG00000143355, ENSG00000258701, ENSG00000224420, ENSG00000099139, ENSG00000135248, ENSG00000204839, ENSG00000143110, ENSG00000179846, ENSG00000215475, ENSG00000170381, ENSG00000171786, ENSG00000280422, ENSG00000091536, ENSG00000130222, ENSG00000111644, ENSG00000180422, ENSG00000272449, ENSG00000262223, ENSG00000272549, ENSG00000107736, ENSG00000268041, ENSG00000233198, ENSG00000172232, ENSG00000260695, ENSG00000180549, ENSG00000260978, ENSG00000270393, ENSG00000162496, ENSG00000213981, ENSG00000237250, ENSG00000058335, ENSG00000272866, ENSG00000132692, ENSG00000275812, ENSG00000143858, ENSG00000197921, ENSG00000170989, ENSG00000237941, ENSG00000026508, ENSG00000109099, ENSG00000168874, ENSG00000175445, ENSG00000268089, ENSG00000122420, ENSG00000109846, ENSG00000106823, ENSG00000100311, ENSG00000267519, ENSG00000115844, ENSG00000197467, ENSG00000183230, ENSG00000121236, ENSG00000166106, ENSG00000182601, ENSG00000005059, ENSG00000135406, ENSG00000116132, ENSG00000138829, ENSG00000110852, ENSG00000080644, ENSG00000213654, ENSG00000196218, ENSG00000106327, ENSG00000144485, ENSG00000215595, ENSG00000182348, ENSG00000245904, ENSG00000089847, ENSG00000205038, ENSG00000276445, ENSG00000244151, ENSG00000162692, ENSG00000196104, ENSG00000133246, ENSG00000198105, ENSG00000197584, ENSG00000100346, ENSG00000244242, ENSG00000102057, ENSG00000100024, ENSG00000168952, ENSG00000115556, ENSG00000007372, ENSG00000038295, ENSG00000111218, ENSG00000172828, ENSG00000166359, ENSG00000099769, ENSG00000280229, ENSG00000131471, ENSG00000255031, ENSG00000169836, ENSG00000134595, ENSG00000188425, ENSG00000118729, ENSG00000234350, ENSG00000273064, ENSG00000179564, ENSG00000174611, ENSG00000100060, ENSG00000101203, ENSG00000129757, ENSG00000154080, ENSG00000165805, ENSG00000226476, ENSG00000018625, ENSG00000198732, ENSG00000148734, ENSG00000173673, ENSG00000231827, ENSG00000142494, ENSG00000112238, ENSG00000184221, ENSG00000177468, and any combination thereof.

In some embodiments, the cell is contacted with an isolated exosome comprising an increased quantity of an NTF compared to exosomes isolated from control MSC. In some embodiments, the cell is contacted with an isolated exosome comprising an increased quantity of an NTF and at least another protein compared to exosomes isolated from control MSC. In some embodiments, the NTF comprises a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and FGF2, or any combination thereof. In some embodiments, the at least another proteins comprises an IL36A, a CCL7, a MMP10, a PIFG, a CXCL8, a LTA, a CXCL6, an MMP3, a CHI3L1, an IL11, a FGF2, a CXCL5, a GAS1, a JAML, a TGFBR3, a MEPE, a IL6, a PDGFA, a CCL4, a CCL21, a CCL2, a MIF, a PLAU, an ANGPTL4, a CTSB, a BSG, a CCL5, a TPO, a IL23, a IL1RL1, a SPP1, a F11R, an INHBA, a FAP, a SPINT2, a IL36G, a TNFRSF10B or a TNFSF14, or any combination thereof.

In some embodiments, the cell is contacted with an isolated exosome comprising an increased quantity of LIF protein compared to exosomes isolated from control MSC. In some embodiments, the cell is contacted with an isolated exosome comprising an increased quantity of VEGFA protein compared to exosomes isolated from control MSC. In some embodiments, the cell is contacted with an isolated exosome comprising an increased quantity of GDF15 protein compared to exosomes isolated from control MSC. In some embodiments, the cell is contacted with an isolated exosome comprising an increased quantity of LIF and VEGFA proteins compared to exosomes isolated from control MSC. In some embodiments, the cell is contacted with an isolated exosome comprising an increased quantity of LIF and GDF15 proteins compared to exosomes isolated from control MSC. In some embodiments, the cell is contacted with an isolated exosome comprising an increased quantity of VEGFA and GDF15 proteins compared to exosomes isolated from control MSC.

In some embodiments, the cell is contacted with an isolated exosome comprising an increased quantity of an NTF and at least another protein compared to exosomes isolated from control MSC. In some embodiments, the cell is contacted with an isolated exosome comprising an increased quantity of an NTF comprising LIF, or VEGFA, or GDF15 proteins, or any combination thereof and at least another protein compared to exosomes isolated from control MSC. In some embodiments, the cell is contacted with an isolated exosome comprising an increased quantity of an NTF and at least another protein comprising IL13 or CXCL1, or any combination thereof, compared to exosomes isolated from control MSC. In some embodiments, the cell is contacted with an isolated exosome comprising an increased quantity of an NTF comprising LIF, or VEGFA, or GDF15 proteins, or any combination thereof and at least another protein comprising IL13 or CXCL1, or any combination thereof, compared to exosomes isolated from control MSC.

In certain embodiments, the cell is within a human body. In certain embodiments, the cell is ex-vivo.

In certain embodiments, the method comprises increasing the expression level of a gene selected from the group consisting of ENSG00000204711, ENSG00000134668, ENSG00000175899, ENSG00000131095, ENSG00000261371, ENSG00000197632, ENSG00000250993, ENSG00000117318, ENSG00000196639, ENSG00000188404, ENSG00000198796, ENSG00000204277, ENSG00000248461, ENSG00000250538, ENSG00000125968, ENSG00000105559, ENSG00000140853, ENSG00000108691, ENSG00000205403, ENSG00000165985, ENSG00000257446, ENSG00000138798, ENSG00000107984, ENSG00000128283, ENSG00000139155, ENSG00000147041, ENSG00000121068, ENSG00000137834, ENSG00000185149, ENSG00000153976, ENSG00000106366, ENSG00000026508, ENSG00000109099, ENSG00000168874, ENSG00000175445, ENSG00000268089, ENSG00000122420, ENSG00000109846, ENSG00000106823, ENSG00000100311, ENSG00000267519, ENSG00000115844, ENSG00000197467, ENSG00000183230, ENSG00000121236, ENSG00000166106, ENSG00000182601, ENSG00000005059, ENSG00000135406, ENSG00000116132, ENSG00000138829, ENSG00000110852, and any combination thereof.

In certain embodiments, the method comprises decreasing the expression level of a gene selected from the group consisting of ENSG00000262484, ENSG00000080644, ENSG00000197847, ENSG00000213654, ENSG00000203688, ENSG00000196218, ENSG00000221818, ENSG00000106327, ENSG00000279232, ENSG00000144485, ENSG00000260941, ENSG00000215595, ENSG00000251161, ENSG00000182348, ENSG00000131480, ENSG00000245904, ENSG00000143355, ENSG00000089847, ENSG00000258701, ENSG00000205038, ENSG00000224420, ENSG00000276445, ENSG00000099139, ENSG00000244151, ENSG00000135248, ENSG00000162692, ENSG00000204839, ENSG00000196104, ENSG00000143110, ENSG00000133246, ENSG00000278910, ENSG00000102359, ENSG00000091583, ENSG00000113263, ENSG00000259070, ENSG00000266928, ENSG00000164850, ENSG00000105825, ENSG00000165899, ENSG00000142748, ENSG00000188501, ENSG00000136869, ENSG00000131094, ENSG00000135547, ENSG00000134531, ENSG00000235884, ENSG00000267280, ENSG00000172548, ENSG00000180801, ENSG00000116745, ENSG00000122585, ENSG00000089327, ENSG00000183691, ENSG00000184557, ENSG00000101825, ENSG00000087510, ENSG00000163251, ENSG00000099860, ENSG00000128342, ENSG00000164488, ENSG00000177337, ENSG00000262001, ENSG00000131203, ENSG00000138316, ENSG00000167306, ENSG00000131724, ENSG00000142089, ENSG00000222041, ENSG00000152049, ENSG00000172965, ENSG00000203805, ENSG00000154274, ENSG00000177359, ENSG00000145623, ENSG00000213694, ENSG00000078081, ENSG00000138496, ENSG00000105974, ENSG00000119917, ENSG00000179846,
ENSG00000215475,
ENSG00000170381,
ENSG00000171786,
ENSG00000280422,
ENSG00000091536,
ENSG00000130222,
ENSG00000111644,
ENSG00000180422,
ENSG00000272449,
ENSG00000262223,
ENSG00000272549,
ENSG00000107736,
ENSG00000268041,
ENSG00000233198,
ENSG00000172232,
ENSG00000260695,
ENSG00000180549,
ENSG00000260978,
ENSG00000270393,
ENSG00000162496,
ENSG00000213981,
ENSG00000237250,
ENSG00000058335,
ENSG00000272866,
ENSG00000132692,
ENSG00000275812,
ENSG00000143858,
ENSG00000197921,
ENSG00000170989,
ENSG00000237941,
ENSG00000018625,
ENSG00000148734,
ENSG00000231827,
ENSG00000112238,
ENSG00000198105,
ENSG00000197584,
ENSG00000100346,
ENSG00000244242,
ENSG00000102057,
ENSG00000100024,
ENSG00000168952,
ENSG00000115556,
ENSG00000007372,
ENSG00000038295,
ENSG00000111218,
ENSG00000172828,
ENSG00000166359,
ENSG00000099769,
ENSG00000280229,
ENSG00000131471,
ENSG00000255031,
ENSG00000169836,
ENSG00000134595,
ENSG00000188425,
ENSG00000118729,
ENSG00000234350,
ENSG00000273064,
ENSG00000179564,
ENSG00000174611,
ENSG00000100060,
ENSG00000101203,
ENSG00000129757,
ENSG00000154080,
ENSG00000165805,
ENSG00000226476,
ENSG00000198732,
ENSG00000173673,
ENSG00000142494,
ENSG00000184221,
ENSG00000177468, and any combination thereof.

The technology provided herein further provides, in another aspect, a method of modulating a Kyoto Encyclopedia of Genes and Genomes (KEGG) pathway in a cell, the method comprising the step of contacting the cell with an isolated exosome population derived from MSC-NTF cells, as described in detail above, wherein the KEGG pathway is selected from the group consisting of hsa04510, hsa04512, hsa04115, hsa05200, hsa04110, hsa05222, hsa05224, hsa05100, hsa05412, hsa04151, hsa05205, hsa04141, hsa05215, hsa04933, hsa04520, hsa04390, hsa05161, hsa01521, hsa04210, hsa03460, hsa04142, and any combination thereof.

In some embodiments, the cell is contacted with an isolated exosome comprising an increased quantity of an NTF compared to exosomes isolated from control MSC. In some embodiments, the cell is contacted with an isolated exosome comprising an increased quantity of an NTF and at least another protein compared to exosomes isolated from control MSC. In some embodiments, the NTF comprises a VEGF, HGF, a LIF, a GDNF, a NT-3, a neurotrophin-4/5, a NTN, a Neurotrophin-4, a Persephin, ART, a CNTF, an IGF-1, a GDF-15, a G-CSF a BDNF, a TSG-6, BMP2, and FGF2, or any combination thereof. In some embodiments, the at least another proteins comprises an IL36A, a CCL7, a MMP10, a PIFG, a CXCL8, a LTA, a CXCL6, an MMP3, a CHI3L1, an IL11, a FGF2, a CXCL5, a GAS1, a JAML, a TGFBR3, a MEPE, a IL6, a PDGFA, a CCL4, a CCL21, a CCL2, a MIF, a PLAU, an ANGPTL4, a CTSB, a BSG, a CCL5, a TPO, a IL23, a IL1RL1, a SPP1, a F11R, an INHBA, a FAP, a SPINT2, a IL36G, a TNFRSF10B or a TNFSF14, or any combination thereof.

In some embodiments, the cell is contacted with an isolated exosome comprising an increased quantity of LIF protein compared to exosomes isolated from control MSC. In some embodiments, the cell is contacted with an isolated exosome comprising an increased quantity of VEGFA protein compared to exosomes isolated from control MSC. In some embodiments, the cell is contacted with an isolated exosome comprising an increased quantity of GDF15 protein compared to exosomes isolated from control MSC. In some embodiments, the cell is contacted with an isolated exosome comprising an increased quantity of LIF and VEGFA proteins compared to exosomes isolated from control MSC. In some embodiments, the cell is contacted with an isolated exosome comprising an increased quantity of LIF and GDF15 proteins compared to exosomes isolated from control MSC. In some embodiments, the cell is contacted with an isolated exosome comprising an increased quantity of VEGFA and GDF15 proteins compared to exosomes isolated from control MSC.

In some embodiments, the cell is contacted with an isolated exosome comprising an increased quantity of an NTF and at least another protein compared to exosomes isolated from control MSC. In some embodiments, the cell is contacted with an isolated exosome comprising an increased quantity of an NTF comprising LIF, or VEGFA, or GDF15 proteins, or any combination thereof and at least another protein compared to exosomes isolated from control MSC. In some embodiments, the cell is contacted with an isolated exosome comprising an increased quantity of an NTF and at least another protein comprising IL13 or CXCL1, or any combination thereof, compared to exosomes isolated from control MSC. In some embodiments, the cell is contacted with an isolated exosome comprising an increased quantity of an NTF comprising LIF, or VEGFA, or GDF15 proteins, or any combination thereof and at least another protein comprising IL13 or CXCL1, or any combination thereof, compared to exosomes isolated from control MSC.

In certain embodiments, the cell is within a human body. In certain embodiments, the cell is ex-vivo.

In certain embodiments, the KEGG pathway is hsa04510. In certain embodiments, the KEGG pathway is hsa04512. In certain embodiments, the KEGG pathway is hsa04115. In certain embodiments, the KEGG pathway is hsa05200. In certain embodiments, the KEGG pathway is hsa04110. In certain embodiments, the KEGG pathway is hsa05222. In certain embodiments, the KEGG pathway is hsa05224. In certain embodiments, the KEGG pathway is hsa05100. In certain embodiments, the KEGG pathway is hsa05412. In certain embodiments, the KEGG pathway is hsa04151. In certain embodiments, the KEGG pathway is hsa05205. In certain embodiments, the KEGG pathway is hsa04141. In certain embodiments, the KEGG pathway is hsa05215. In certain embodiments, the KEGG pathway is hsa04933. In certain embodiments, the KEGG pathway is hsa04520. In certain embodiments, the KEGG pathway is hsa04390. In certain embodiments, the KEGG pathway is hsa05161. In certain embodiments, the KEGG pathway is hsa01521. In certain embodiments, the KEGG pathway is hsa04210. In certain embodiments, the KEGG pathway is hsa03460. In certain embodiments, the KEGG pathway is hsa04142.

EXAMPLES

Example 1

Production, Purification, and Characterization of MSC-NTF Exosomes

Objective: To produce cell-type specific MSC-NTF exosomes. Although this example describes production of MSC-NTF exosomes, it is expected that MSC derived exosomes could be similarly isolated using the methods described herein and MSC or genetically modified MSC.

Methods:

Preparation of Differentiated Human BM-MSC (MSC-NTF) and Exosome Production & Purification Methods for isolation of human bone marrow-MSCs (BM-MSC) are well known in the art and fully described in International Patent Application Publication Nos. WO 2015/121859 and WO 2014/024183, which are incorporated herein, in their entirety.

Bone marrow samples (50-100 ml) were collected into Heparin-containing tubes from the posterior iliac crest of healthy adult human donors by bone marrow aspiration. Bone marrow aspirates were diluted 1:1 with DMEM and mononuclear cells were separated by density centrifugation (1000× G for 20 min), over Ficoll (Ficoll-Paque PREMIUM) containing tubes. The mononuclear cell fraction was collected and washed in DMEM. Cells were re-suspended in Growth Medium containing 10% Platelet lysate (PM; see below), counted by the Trypan blue exclusion dye and seeded at a concentration of up to 300,000 cells/cm$^2$ in 2-Chamber CellStacks. Flasks were incubated in a 37° C. humidified incubator with 5% $CO_2$.

PM growth medium consisted of Dulbecco's Modified Eagle's Medium low glucose (Sigma, Aldrich), supplemented with L-Glutamine solution 200 mM (Sigma, Aldrich), Sodium Pyruvate solution 100 mM (Sigma, Aldrich), 2 IU/ml Heparin (APP Pharmaceuticals), and 10% platelet lysate. 16-24 hours later PM medium was aspirated to remove non-adherent cells from the flask, adherent cells were washed gently with 10 ml of DMEM, and 30 ml of fresh PM were added to the flask. hMSC cells were allowed to proliferate for 12-15 days in PM medium, which was replaced two-three times a week. After 12-15 days or when the flask reached confluence. The cells were harvested by removing all growth medium and incubating in TrypLE™ solution (Invitrogen) (A recombinant enzyme replacing animal trypsin for the dissociation of adherent mammalian cells from plastic) for 5 min in a 37° C. incubator. Cells were then washed in DMEM, counted, and cryopreserved in 10% DMSO in PM at a concentration of 15×106 cells/ml/cryovial. Cryopreservation is in liquid nitrogen.

To avoid the need for repeated bone marrow aspirations, in some cases, MSC were cryopreserved at either passages P0, P1, or P2, and multiple fresh MSC-NTF cell doses were produced from the cryopreserved MSC, which were thawed and propagated prior to induction to MSC-NTF cells.

Thawed MSC cultures were resuspended in PM medium, and seeded in CellStacks (Cell culture flask chambers for cell culture scale-up) at a density of 2000 cells/cm$^2$ and differentiation was induced four days later by replacing the growth medium (PM) with a serum free DMEM medium containing 1 mM of dibutyryl cyclic adenosine monophosphate, 20 ng/ml of human basic fibroblast growth factor, 5 ng/ml of human platelet-derived growth factor, and 50 ng/mL of human heregulin-β1 (S2M) for three additional days.

Then, culture medium from the above differentiated cells (MSC-NTF cells) was then collected, and cell debris and large vesicles were removed by filtration through a 0.22-μm filter. The exosome containing filtrate was collected under sterile conditions and subjected to Tangential Flow Filtration (TFF; GE Healthcare Life Sciences).

Scale-Up MSC-NTF Cell Production and Exosome Production & Purification

For scaling-up exosomes manufacturing, secretion, and yield, thawed MSC cultures were resuspended in PM medium, and seeded in CellStacks for (several days') propagation. MSC were then harvested and re-seeded in a Cel-Cradle™ bioreactor bottle on BioNocII Macrocarriers (EscoVacciXcell, Singapore) at a density of 2,000-2,600 cells/cm$^2$ in 500 ml of PM for 4 days. PM was replaced after two days. In some embodiments, after four days PM was replaced with S2M for three days for inducing differentiation. At the end of the differentiation process the conditioned media was collected and cell debris and large vesicles were removed by filtration through a 0.22-μm filter.

The exosome containing filtrate was collected under sterile conditions and subjected to Tangential Flow Filtration (TFF; GE Healthcare Life Sciences). The yield of purified exosomes was in the range of about 3-4×10$^{11}$ which was up to about 4-5-fold the yield obtained from the process using CellStacks alone (about)7×10$^{10}$.

Independent of the method used for exosome production and purification, control exosomes were produced from MSC cells using DMEM with 10% exosomes depleted platelet lysate to avoid the possible confounding effect of platelet lysate derived exosomes. Platelet Lysate-derived exosomes were removed from the PL to avoid their confounding effects on the results.

Interestingly, the three-dimensional (3D) cell manufacturing process (on carriers in bioreactor bottles described above) led to an increased secretion of exosomes from the MSC-NTF cells, and an increased final purified yield of exosomes as compared to the exosomes purified from the 2D culture methods using CellStacks alone, about 3-4×10$^{11}$ purified exosomes versus about 7×10$^{10}$ purified exosomes, respectively. This is a significant difference in the number of exosomes purified from a conditioned media volume in which a similar number of cells was seeded.

Preparation of Platelet Lysate

Platelet lysate may be prepared using any method known in the art. For example, in one embodiment, a platelet lysate may be prepared using a freeze-thaw protocol as provided below.

Platelet Rich Plasma (PRP) may be from Blood Bank donations determined free of infectious agents (i.e. HIV, HTLV, HCV, HBsAg). PRP containing bags were stored at −80° C. and thawed in a 37° C. water bath. After thawing, the Platelet Rich Plasma of multiple donors was pooled, mixed and centrifuged at 14000× G for 10 minutes to remove platelet particles and membranes. The Platelet lysate supernatant was then collected and frozen at −80° C. until use. The Platelet lysate was tested for Endotoxin, Haemoglobin, pH, Total protein, Albumin, Osmolality Sterility and Mycoplasma.

Isolation of MSC-NTF Cell-Specific Exosomes

Tangential Flow Filtration (TFF)—either 100, 300, 500-kDa MWCO membranes were used (Spectrum Lab). The exosome-containing sample (filtrate) was continuously pumped through the fiber system and recirculated Small molecules, including free proteins not included within or associated with the membrane vesicles, were driven through the membrane pores, subsequently eluted as permeate, and eventually discarded. Molecules too large to pass through the pores, such as exosomes (or larger microvesicles), were kept in circulation as retentate. The sample was subjected to five rounds of diafiltration in order to further deplete the sample of contaminants smaller than the kDa MWCO membrane. During the last cycle of diafiltration, the sample was reduced to a volume of ~10 ml.

Size Exclusion Chromatography (SEC)—For high-purity exosomes, TFF was followed by SEC (Exo-Spin™ midi columns; Cell Guidance Systems Ltd, a modular system that provides purification of exosomes) according to manufacturer's instructions. Alternatively, SEC was not performed and a step of TFF was enough to isolate the exosomes.

In case of low recovery, field flow fractionation (FFF), which is based on laminar flow of particles in a solution, where a mixture of particles is propelled through a channel, perpendicular to the direction of flow, resulting in separation of the particles present in the suspension was used. Similar to SEC, FFF separation is dependent on exosomes hydrodynamic diameter, however, this method is unique as compared to other separation methods, since it can separate components over a wide colloidal size range.

Characterization of the purified exosomes was performed at several levels including quantification, phenotype and cargo content.

Nanoparticle Tracking Analysis

Amount and size of particles were measured using a ZetaView Nanoparticle Tracking Analyzer (ParticleMetrix) (Nanoparticle Tracking Analysis technology capable of characterizing reliably in water or physiological buffers), a laser scattering video microscope tracking the movement of individual nanoparticles under Brownian motion. Five exposures at 11 measurement positions were recorded for each sample. Particle size was calculated according to the Stokes-Einstein equation by the Zeta View software (Zeta View 8.02.28).

Transmission Electron Microscopy (TEM)

Exosomes were fixed in 2% paraformaldehyde and 2% glutaraldehyde, and loaded onto a 200 mesh Lacey Formvar carbon-coated grid (Ted Pella, Inc.) and immediately frozen in ethane (gas).

Western Blot Analysis

Protein samples of the exosomes are prepared by RIPA buffer with protease inhibitors. Western blot analysis is performed on exosome-specific markers such as CD9, CD63 and TSG101. Calnexin which is only expressed and localized to the cell endoplasmic reticulum and not present on exosomes, is tested as a negative marker.

miRNA Expression Analysis

Exosome total RNA is prepared using a mirVana™ miRNA Isolation Kit (Life technologies, Carlsbad, Calif.) (an miRNA Isolation Kit that uses a rapid procedure to isolate small RNAs from tissue and cells). The manufacturer's standard isolation procedure is followed.

Total exosome RNA is used for human NanoString nCounter miRNA assay (assays for analyzing the expression of up to 800 genes using a selection of pre-designed or custom panels) (Nanostring Technologies, Seattle, Wash., USA) according to the manufacturer's instructions. To validate the NanoString data, a qRT-PCR analysis is performed.

Protein Array

Protein samples of the exosomes are prepared by Cell Lysis Buffer (RayBiotech, Inc., GA), and subjected to RayBio Human Array Q440 (RayBiotech) (a life sciences company providing proteomic discovery tools) or similar array which quantitatively measures 440 human factors such as cytokines, chemokines, neurotrophic factors, and growth factors. The assay is performed according to the manufacturer instructions, or by employing the manufacturer service.

Results:

Exosomes Size and Quantification

Exosomes were isolated from conditioned media of MSC-NTF cells using the TFF method. The size and the total number of exosomes were analyzed using the ZetaView (Particle Metrix) and its corresponding software (ZetaView 8.02.28). Samples were diluted in PBS, were loaded into the ZetaView cell, and the instrument measured each sample at 11 different positions. The mean, median, (indicated as diameter) sizes, as well as the concentration of the sample, were calculated (see FIG. 1). The median was 132 nm±16, mean was 132.1 nm±15. For each measurement, the instrument pre-acquisition parameters were set to a temperature of 23° C. and a sensitivity of 75 (the optimal arbitrary measure recommend by the manufacturer).

Transmission Electron Microscopy (TEM) Analysis of Exosomes

After determining that the diameters of MSC-NTF-derived exosomes were within the expected range for exosomes (30-150 nm), their shape and integrity were confirmed using TEM imaging, which is a well-accepted technique for nanoparticle validation. Exosomes were fixed in 2% paraformaldehyde, and 2% glutaraldehyde, loaded onto 200 mesh Lacey Formvar carbon-coated grids (Ted Pella, Inc.) and immediately frozen in ethane (gas). Images presented in FIGS. 2A-2B show particles with the classic morphology of exosomes within the measured size range.

Exosomes Uptake by Neurons

A primary function of exosomes is their ability to deposit their cargo inside a recipient cell. In order to examine the ability of the exosomes to enter cells, exosomes were stained with two different fluorescent dyes: an RNA selective dye (SYTO®—a green fluorescent nucleic acid stain, RNASelect™—green fluorescent cell stain in a cell-permeant nucleic acid stain that selectively stains RNA; Life Technologies) or by membrane staining using Calcein AM (Life Technologies) which is non-fluorescent until it passively enters extracellular vesicles, after which it is activated and becomes fluorescent. To clear unbound dye, exosomes and controls were transferred to 10 kDa MWCO Amicons (Amicon Ultra-0.5 Centrifugal Filter Unit). As a control, dye was added to PBS without exosomes using the same protocol.

Figure 3B:
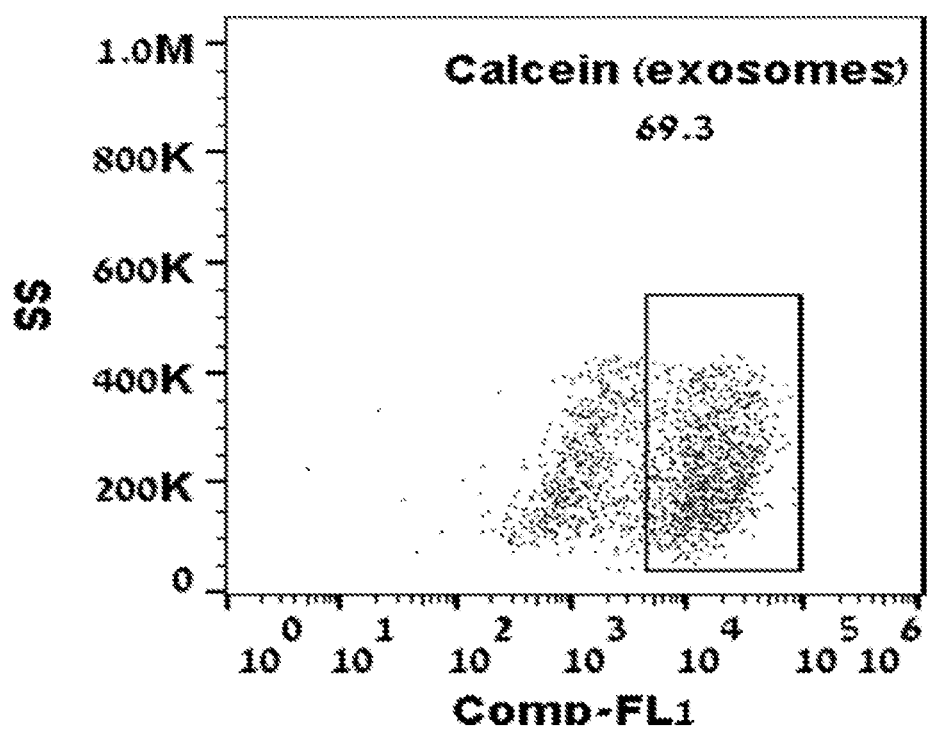

In order to assess exosomes uptake in recipient cells, iPSC motor neurons (carrying a TDP43 mutation) were incubated overnight with stained exosomes followed by FACS analysis and fluorescence microscopy, that confirmed uptake of the fluorescent exosomes in 70% of the cells (FIGS. 3A-3B).

Potency Assay: Immunomodulation

In order to evaluate the immunomodulatory potential of MSC-NTF derived exosomes, their effect on mitogen-induced T-cell proliferation was determined. Carboxyfluorescein succinimidyl ester (CFSE) pre-labeled pooled PBMCs were stimulated with the mitogen phytohemagglutinin (PHA) and cultured in 24-well plates ($1 \times 10^6$ PBMC/well) with increasing amounts of MSC-NTF derived exosomes for four days. The T-cell proliferation rate was determined by the reduction of CFSE intensity through cell divisions.

Further, the immunomodulatory effect of MSC-NTF derived exosomes on induction of T regulatory cells (T-regs) was also evaluated. PBMC were cultured in the presence or absence of MSC-NTF exosomes for three days, following which T-reg levels were determined by flow cytometry.

Figure 4A:
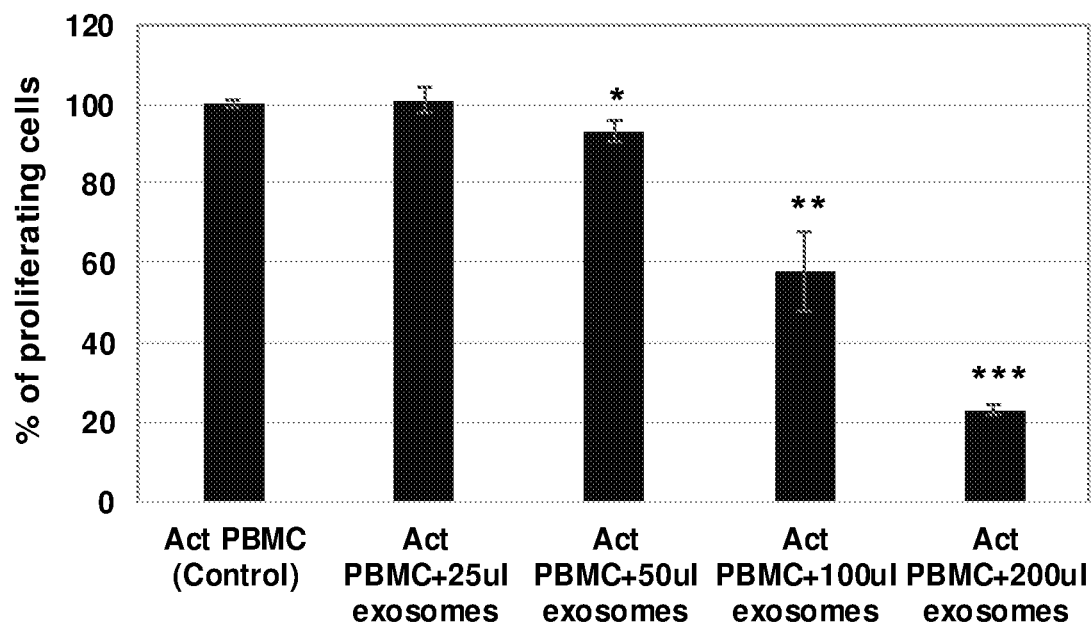
FIGS. 4A-4E present immunomodulatory effects of MSC-NTF exosomes. Activated PBMC were co-cultured with or without exosomes ($3.3 \times 10^{10}$/ml) for 96 hours and examined for CD4$^+$ T-cell proliferation after 96 hours (FIG. 4A), induction of IFN-γ secretion after 96 hours (FIG. 4B), and induction of TNF-alpha secretion after 96 hours (FIG. 4C). (*$p<0.05$; $p<0.01$; *$p<0.001$, n=3±SD).
Figure 4B:
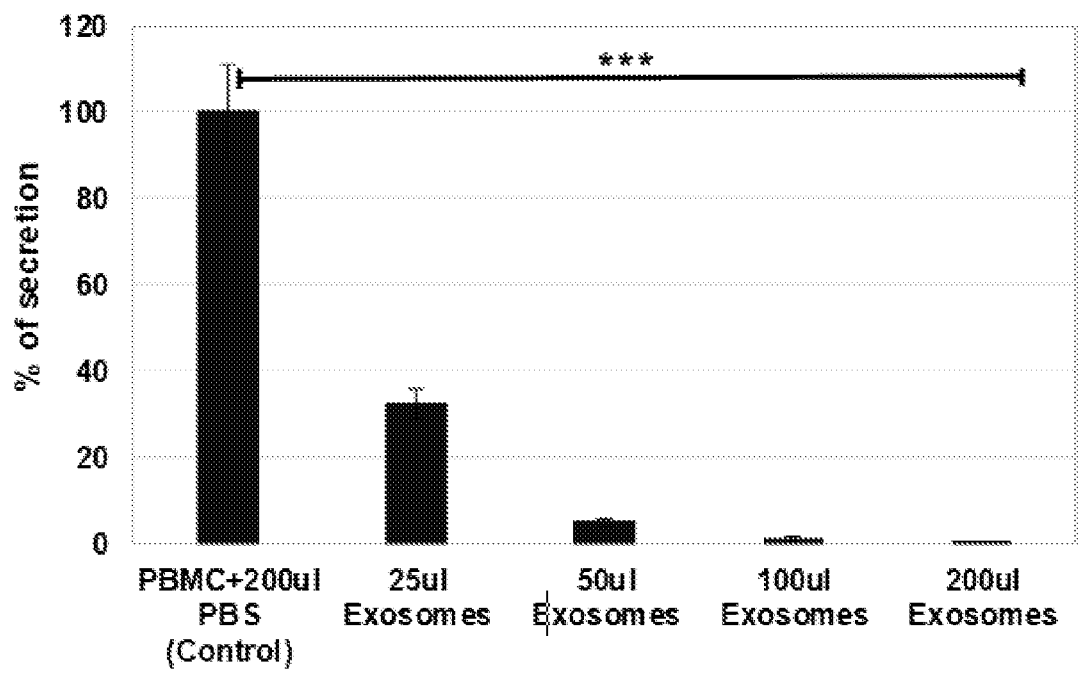
Figure 4C:
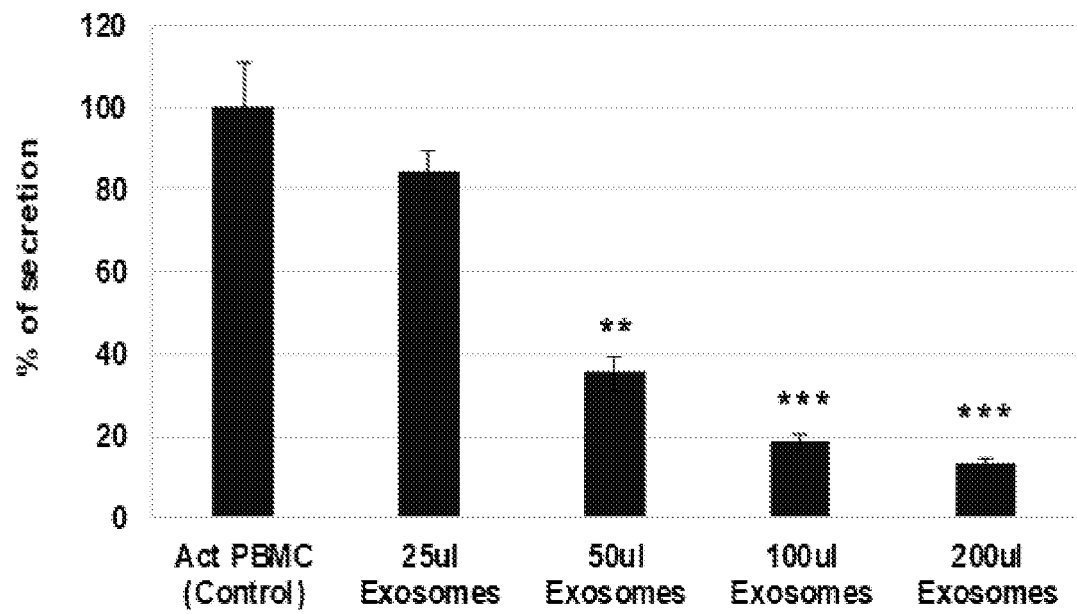
Figure 4D:
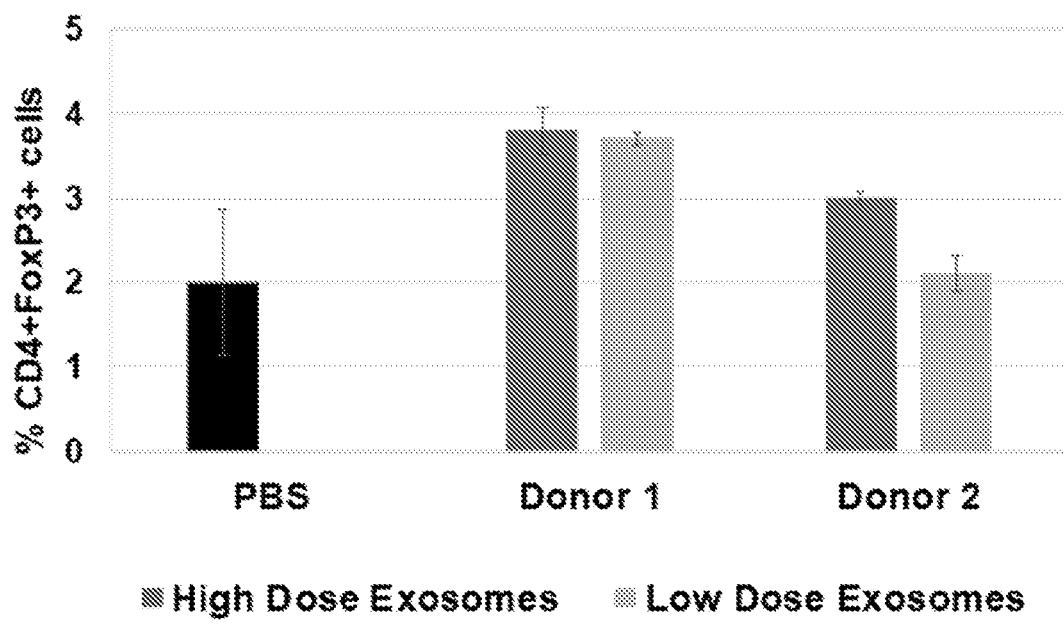
Figure 4E:
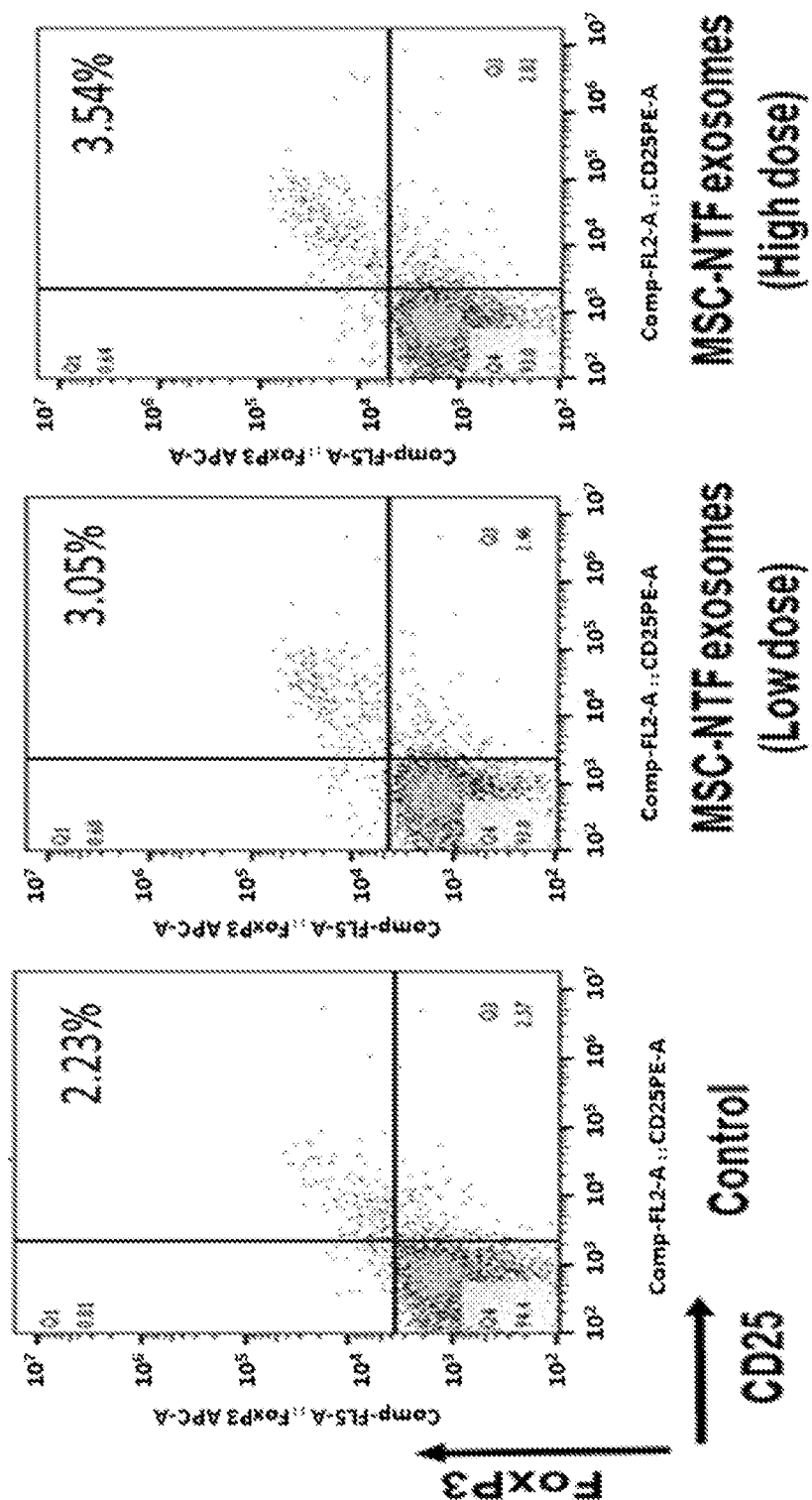

To assess immunomodulation potency of the purified exosomes, activated PBMC were co-cultured with or without exosomes ($3.3 \times 10^{10}$/ml) for 96 hours and examined for CD4+ T-cell proliferation (FIG. 4A), IFN-γ secretion (FIG. 4B), and TNF-alpha secretion (FIG. 4C). FIG. 4D illustrates a dose-dependent increase of T-reg levels in PBMCs from two different healthy donors which were co-cultured with MSC-NTF derived exosomes ($4.6 \times 10^9$ and $2.3 \times 10^9$) for 3 days, as determined by flow cytometry. FIG. 4E illustrates a dose-dependent correlation between MSC-NTF exosomes and the induction of CD4$^+$CD25$^+$FoxP3$^+$ (T-reg) cells from PBMCs from a single donor.

When PHA-induced PBMCs were cultured in the presence of MSC-NTF derived exosomes, a dose-dependent inhibition of T-cell proliferation (ranging from 93 to 23%), was observed, which correlated to the increasing amounts of exosomes (FIG. 4A) Similar range dose dependent inhibition of IFN γ (range 32-0.15%) and TNFα (range 13-84%) secretion was measured by ELISA. (FIGS. 4B, 4C). IFN γ and TNFα levels were measured after 96 hours incubation of MSC-NTF and exosomes.

Conclusion: exosomes can readily be isolated from MSC-NTF cells and found to have different attributes which make them beneficial for a variety of utilities. Importantly, these attributes have been demonstrated for isolated exosomes, without any effect from the producing MSC-NTF cells.

Example 2

Modification of MSC or MSC-NTF Exosome Cargo

Objective: To prepare modified MSC or MSC-NTF derived exosomes for use as nano-carriers for siRNA, miRNA, or proteins, thereby producing a targeted population of MSC-NTF derived exosomes. By encapsulating molecules within their membranes, exosomes can protect proteins or RNAs from degradation. Moreover, while serving as nano-carriers for a specific target, MSC or MSC-NTF derived exosomes still maintain their original therapeutic potential.

Using exosomes as nano-carriers for siRNA, miRNA, or protein delivery has striking advantages. For example, comparing delivery of siRNA and siRNA-loaded exosomes into neurons or into mice brain has shown better distribution and efficacy of the siRNA-loaded exosomes (Didiot et al., (2016) Exosome-mediated Delivery of Hydrophobically Modified siRNA for Huntingtin mRNA Silencing. Mol Ther. 24(10) 1836-1847; Alvarez-Erviti et al., (2011) Delivery of siRNA to the mouse brain by systemic injection of targeted exosome. Nat Biotechnol. 29:341-345).

Both Loss-of-Function and Gain-of-Function MSC or MSC-NTF derived exosomes are prepared.
Methods:
Loss of Function (Silencing)

Loading of synthetic siRNAs into naturally secreted extracellular vesicles has been shown to promote cellular uptake and target gene silencing in the recipient cell. Methods known in the art are used to load the MSC or MSC-NTF-derived exosomes with siRNA. For example, see methods presented in S El-Andaloussi et al., (2012) Exosome-medicated delivery of siRNA in vitro and in vivo. Nat Protoc. 7(12):2112-2126).

Several different siRNA sequences are designed to the coding sequence common to mouse and human MMP9. Exosomes are loaded with fluorescently tagged siRNA by electroporation and exosome loading and assessed using Qubit 3.0 flurometer (Thermo) following clearance of unloaded siRNAs by ultra-filtration. Exosomes mixed with siRNA without electroporation will serve as a control.

iPSC derived motor neurons are used to assess whether exosomes loaded with siRNAs are able to specifically deliver their cargo in vitro. Uptake are assessed using Fluorescence Microscope (Olympus) and Flow Cytometry, as shown above in Example 1. RT-PCR analysis are used to demonstrate whether delivery with targeted exosomes achieves comparable gene knockdown in the recipient cell.

Modified MSC or MSC-NTF-derived exosomes are functionally compared to control un-modified MSC or MSC-NTF and control MSC derived exosomes in functional models as described above.
Gain of Function (Over-Expression)

Proteins or miRNA are loaded into exosomes either directly or through genetic engineering of the donor MSC cells, as is well known in the art, whereby the cells synthesize a protein or peptide encoded by an inserted gene or nucleic acid sequence, and these proteins or peptides are subsequently secreted into the extracellular vesicles (exosomes).

Several different methods were suggested for protein loading directly into exosomes including incubation at room temperature, permeabilization with saponin, freeze-thaw cycles, sonication, or extrusion (See for example the methods presented in Haney et al., (2015) Exosomes as drug delivery vehicles for Parkinson's disease therapy. J Control Release, 10(207)18-30).

The efficiency of directly loading any of miRNA-7, GDF5, IGF-1 or IGF-2, or a combination thereof, into MSC or MSC-NTF-derived exosomes are performed by either permeabilization with saponin or sonication (two of the methods that were found to be most effective). Loaded with the miRNA or factor, exosomes are purified from free factor or miRNA using size exclusion chromatography (SEC; ExoSpin). Content of GDF5, IGF-1 or IGF-2 are measured using ELISA (R&D systems) and content of miRNA-7 are measured by RT-PCR.

If direct transfection of proteins into exosomes results in low efficiency, miRNA-7, GDF5, IGF-1 or IGF-2 are highly expressed in MSC cells using the XPack technology (SBI).

Modified MSC or MSC-NTF-derived exosomes are functionally compared to control un-modified MSC or MSC-NTF cells and control MSC derived exosomes in the functional models described above for Loss-of-Function exosomes.
Results:

It is expected that the above methods will produce specific Loss-of-Function and Gain-of-Function MSC or MSC-NTF-derived exosomes.

Conclusion: in addition to their natural intrinsic attributes, isolated exosomes can incorporate additional cargo molecules, e.g. within their membrane or inner volume, to either enhance a beneficial natural attribute or obtain a new beneficial attribute.

Example 3

In Vitro & In Vivo Characterization of Modified and Non-Modified MSC or MSC-NTF Exosomes Objective: To characterize the modified MSC or MSC-NTF derived exosomes for biological function in vitro and in vivo.
Methods:

Various biological functions of MSC, genetically modified MSC, MSC derived exosomes, modified MSC derived exosomes, MSC-NTF derived exosomes, and modified MSC-NTF derived exosomes including neuroprotection, suppression of inflammation, and improved functional recovery are evaluated in different models.

Exosomes Labeling and Uptake by Recipient Cells

A primary function of exosomes is their ability to deposit their cargo inside a recipient cell. In order to examine the ability of the modified exosomes to enter cells, the modified exosomes are labeled as in Example 1 for non-modified MSC-NTF derived exosomes, with two different fluorescent dyes: an RNA selective dye (SYTO® RNASelect™; Life Technologies) or by membrane labeling using Calcein AM (Life Technologies), which is non-fluorescent until it passively enters extracellular vesicles, after which it is activated and becomes fluorescent. The modified MSC or MSC-NTF derived exosomes are co-cultured with motor neurons for 3-24 hours and uptake is assessed using Fluorescence Microscopy (Olympus) and Flow Cytometry (FACS; FC500, Beckman Coulter).

In Vitro Immunomodulation

As neuro-inflammation is one of the striking hallmarks of ALS, the immunomodulatory potential of modified MSC, modified MSC-NTF derived, and control MSC derived exosomes is determined using an activated PBMC assay (as shown in FIGS. 4A-4E for non-modified MSC-NTF derived exosomes). Three parameters are tested: inhibition of proliferation of $CD4^+$ cells by a CFSE assay using FACS analysis, induction of $CD4^+CD25^+FoxP3^+$ T regulatory cells using FACS analysis, and inhibition of inflammatory cytokines such as IFN-γ and TNF-α using specific ELISA kits (R&D systems). Unpaired t-tests or ANOVA are performed for statistics analysis.

In Vitro Neuro Functional Assays in Different Cell Types

Human Neural Precursor Stem Cells

Cells are originated from either embryonic stem cells (Stem cell technologies) or iPSC (ATCC able to differentiate into immature or mature neurons, dopaminergic neurons and Glia cells, serve as a good assay for neurogenesis and neuroprotection.) These neural precursor stem cells are co-cultured with or without MSC, modified MSC derived exosomes, MSC-NTF derived exosomes, or modified-MSC-NTF derived exosomes.

The following parameters are studied:

A Gene and miRNA expression at different co-culture time points (Affimetrix GeneChip arrays, RT-PCR, a platform for accurate, sensitive, and comprehensive measurement of protein coding).

B. Neurite Extension (IncuCyte®, NeuroTrack™ Analysis Software)

Human DCX-GFP cells (ATCC) are Neural progenitor cells in which GFP is expressed under the Doublecortin (DCX), a cytoskeleton-associated protein that is expressed transiently in the course of adult neurogenesis, promotor. DCX-GFP cells were plated on CellMatrix coated 96 well plates at a cell density of 5,000 cells/well in expansion medium (ATCC). 24 h after plating, medium was changed to dopaminergic differentiation medium (ATCC, 100 µl/well) with or without the addition of 20 µl of PBS, or 20 µl MSC-NTF exosomes, or 10 µl exosomes +10 µl PBS or 1 µl MSC-NTF exosomes (exosome concentration: $1.1 \times 10^7$ exosomes/µl).

Figure 5A:
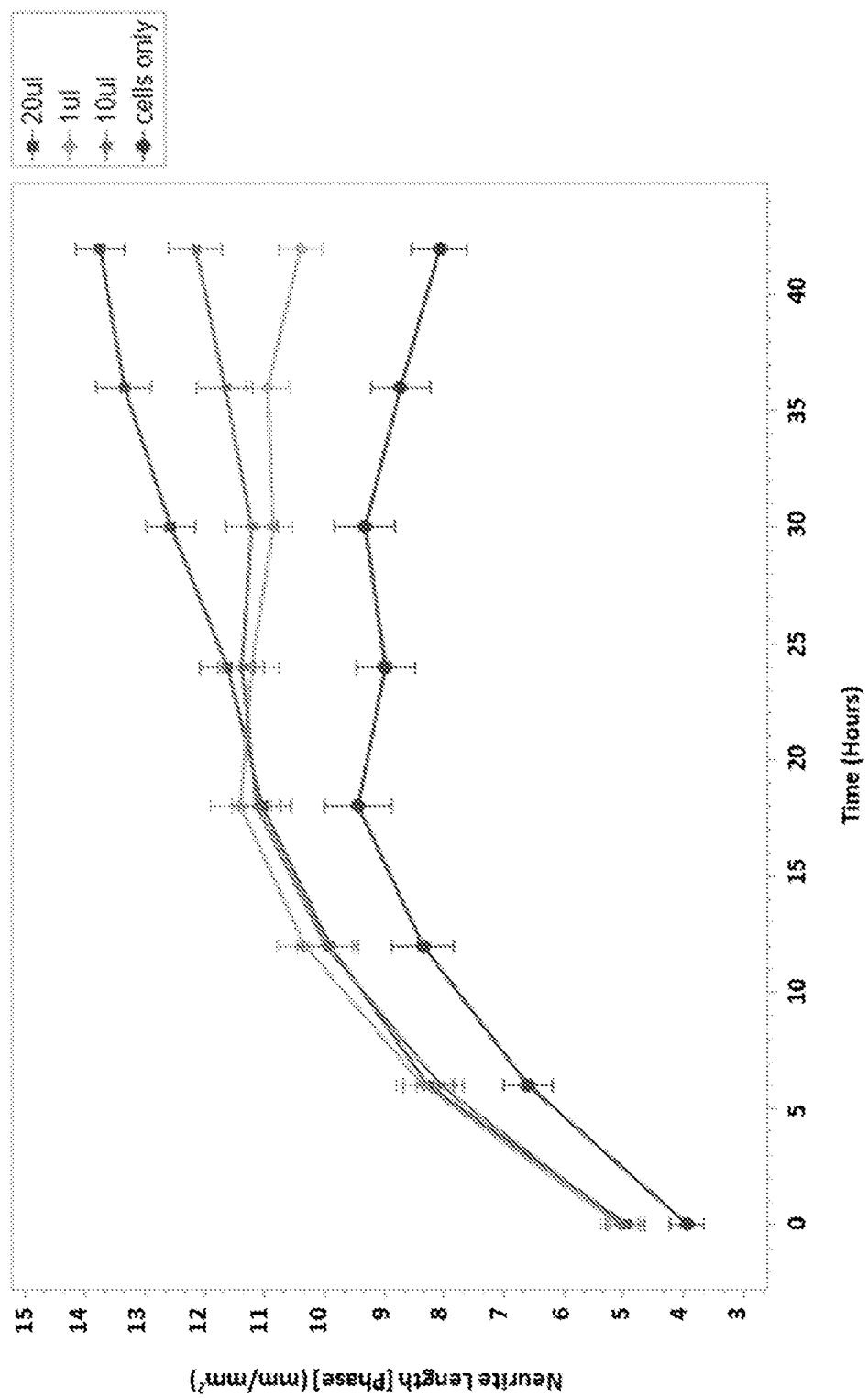
FIGS. 5A-5C present functional responses of neuronal cells to isolated exosomes.
Figure 5B:
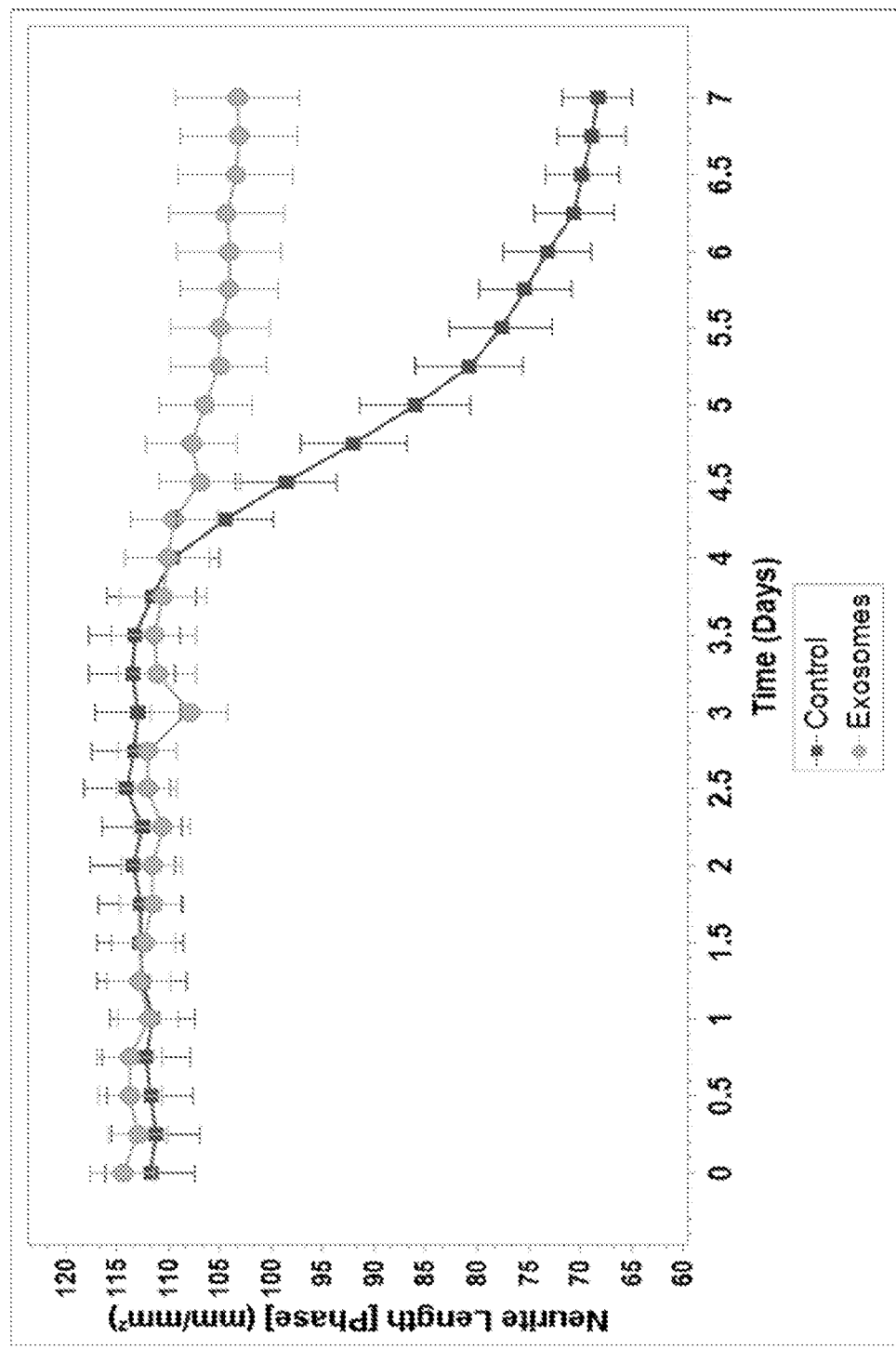
Figure 5C:
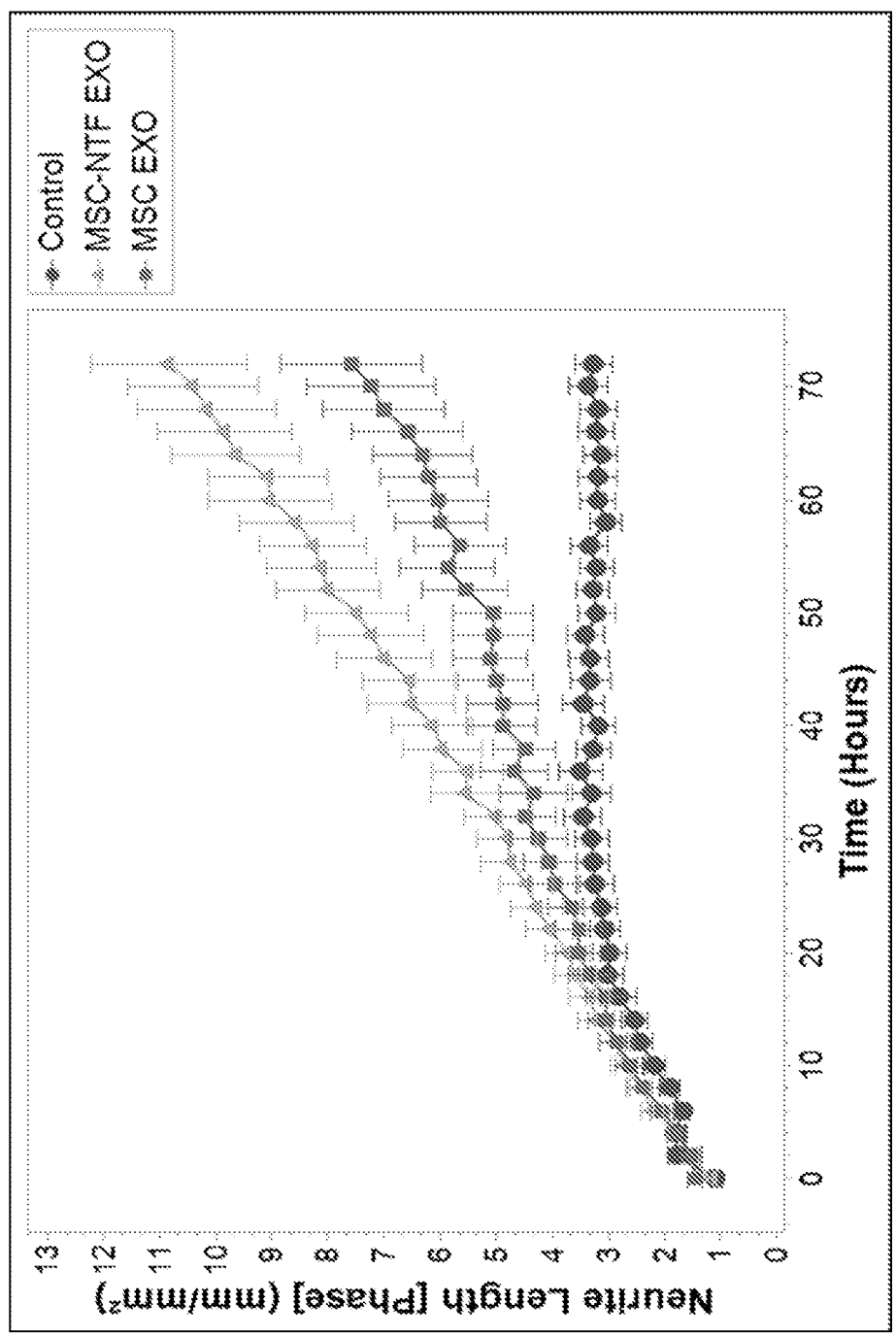

Neurite outgrowth was determined as the total length of individual neurites and was monitored using the IncuCyte S3 live imaging system (Essen Bioscience) at 6 hours intervals (FIG. 5A). FIG. 5B illustrates that MSC-NTF exosomes rescue neurons from neurotrophic-factor deprivation induced cell death. Neural progenitor cells derived from iPSCs (StemCell technologies Cat #70901) were differentiated into mature neurons for 14 days using neuron differentiation and maturation medium (Stemcell Technologies). On day 15 medium was changed to neurotrophic factor-deprived medium supplemented with MSC-NTF derived exosomes (2-4×109 particles) or PBS. Cells were maintained in culture for 7 additional days. Cells were imaged during this time at 6 hours intervals using Incucyte S3 live imaging system. Neurite length was calculated using the Neurotrack module. FIG. 5C illustrates that MSC-NTF exosomes induce neurite outgrowth. SH-SY5Y cells were seeded in 96 well plates, in DMEM F12 supplemented with 10% FBS at a cell density of 35000 cells/cm2. 24 hours later medium was replaced with serum free DMEM F12, and exosomes (~2×109 particles) were added to each well. Cell were imaged using the Incucyte S3 live imaging system at 2 hours intervals (Incucyte software for the process of acquiring, viewing, analyzing and sharing images of living cells). Neurite length was calculated by using the Neurotrack module (company for digital cognitive health solutions).

Conclusion: in similarity to MSC exosomes, MSC-NTF exosomes also have a neuroprotective effect. However, the neuroprotective effect of MSC-NTF exosomes is significantly superior compared to the neuroprotective effect of MSC exosomes.

A. $H_2O_2$ and 6-OHDA are used to evaluate Protection from neurotoxicity using the LDH release assay and the mitochondrial activity-MTS assay. Human neural progenitor cells (StemCell Technologies) are grown in neuron differentiation medium for 1 week, then plated on Poly-L-Ornithine (PLO) and laminin coated 96 well-plates at a cell density of 20,000 cells/well, and grown in neuron maturation medium (StemCell technologies). During neuron maturation cells are treated with 20 µl PBS, 20 µl of MSC-NTF exosomes, 10 µl of MSC-NTF exosomes or 1 µl of MSC-NTF exosomes (MSC-NTF exosome concentration: $4.5 \times 10^6$ exosomes/µl). After 5 days of neuron maturation medium is changed to F12 medium supplemented with increasing concentrations of $H_2O_2$ (10 µM, 20 µM, 40 µM or 60 µM). After 18h the MTS assay (Abcam) is performed to assess cell viability to determine the protective effect of MSC-NTF exosomes.

B. Exosomes are visualized and quantified by Fluorescent microscopy by using markers of neurons (Tuj1), microglia (IBA-1) and astrocytes (GFAP) as applicable.

iPSC-Derived Motor Neurons (MNs); Genetic and Sporadic Model for ALS

MNs from ALS patients' iPSCs have revealed specific disease-relevant phenotypes, thereby validating the use of this system to explore the molecular underpinnings of ALS and to develop new screening platforms for drug development. Using an ALS patient's MNs iPSCs platform, modified MSC derived exosomes, MSC-NTF derived exosomes, modified MSC-NTF derived exosomes, and control MSC derived exosomes are examined for their neuro-protective potential on iPSC-derived MNs bearing TDP-43 mutations (M337V and Q331K) and iPSC-derived MNs isogenic control (Cellular Dynamics). In addition, iPSC-derived motor neurons originating from C9ORF72 mutated and sporadic ALS (New York Stem Cell Foundation) patients are studied.

The following parameters are studied: A: Gene and miRNA expression at different culture time points (Affimetrix GeneChip arrays, RT-PCR); B: Physiological activity-Acetyl Choline secretion (Colorimetric assay); C: Evaluation of cell death (LDH release; Colorimetric assay); D: Staurosporine (STS) which is known to inhibit protein kinases and to induce apoptosis by activating caspase-3, is used to evaluate the sensitivity of the healthy vs mutated cells, comparing cytotoxicity (LDH release) and mitochondrial activity (MTS assay); and E: Visualization and quantification by Fluorescent microscopy by using markers of neurons (Tuj1), motor neurons (Isl-1), microglia (IBA-1) and astrocytes (GFAP) when applicable.

Primary Rat Neuronal Cultures; α-Synuclein Inclusion Model for PD

MSC, modified MSC derived exosomes, MSC-NTF derived exosomes, and modified MSC-NTF derived exosomes inhibition of α-synuclein inclusion formation in primary rat neuronal cultures and defects in neuronal function is determined as following: A: Primary rat neuronal cultures are prepared from Sprague-Dawley rats; B: Primary rat neuronal cultures are incubated with mouse alpha synuclein fibrils for a total of 2, 4, 7, 10, 14, 21 days with 3 different concentrations of control MSC, modified MSC, MSC-NTF, and modified MSC-NTF-derived exosomes, or no exosomes; C: Abundance of phosphorylated α-synuclein inclusions by immunofluorescence and by immunoblots of neurons sequentially extracted with 1% Tx-100 followed by 2% SDS are quantified; D: Calcium imaging with AAV-SynapsinI-GCamp6 is used to determine if exosomes prevent impairments in calcium signaling caused by the inclusions; and E: Determination of the results of intrathecal delivery of MSC, modified MSC, MSC-NTF, or modified MSC-NTF-derived exosomes towards the reduced formation of α-synuclein inclusions and dopamine neuron loss in the cortex, hippocampus and amygdala of rats is made.

In Vivo Studies

SOD-1 G93A Murine Model for ALS

SOD1 mutant mice develop a phenotype reminiscent of ALS in humans. Several studies have shown that MSC cells as well as MSC culture medium improve survival and motor function of mutant SOD1/G93A mice. Thus, B6SJL-TgN SOD1/G93A1 mice expressing a high copy number of mutant human SOD1 with a Gly93Ala substitution (SOD1/G93A) and B6SJL-TgN (SOD1)2 mice expressing wild-type human SOD1 (SOD1) (Jackson Laboratories) are used to assess the effect of modified MSC, MSC-NTF, modified MSC-NTF, and control MSC-derived exosomes on disease progression, onset of symptoms and life span.

Modified MSC, MSC-NTF, modified MSC-NTF, or control MSC-derived exosomes are administered either intrathecally or intranasally to maximize effect and avoid systemic side effects.

The effects of the different exosome populations on motor function are investigated by Rotarod, motor deficit scores and weighing, all of which are commonly used to evaluate SOD1/G93A animals (Weydt et al., (2003) Assesing disease onset and progression in the SOD1 mouse model of ALS. Neuroreport. 3; 14(7):1051-1054).

To visualize the distribution of exosomes in the spinal cord and brain parenchyma 6-48 hours after administration, modified MSC, MSC-NTF, modified MSC-NTF, or control MSC-derived exosomes are labeled with PKH26 or BODIPY TR ceramide dye. Serial sections through the entire brain and spinal cord are processed for immunofluorescence by using markers of neurons (neuronal nuclear antigen (NeuN)), microglia (IBA-1) and astrocytes (GFAP), using confocal microscopy (Olympus). Images are analyzed by using an Olympus image browser.

α-Synuclein Model for Parkinson's Disease (PD)

Sprague-Dawley rats with unilateral injections of sonicated mouse PFFs, monomeric α-synuclein, or PBS into the striatum are used to determine if intrathecal delivery of exosomes or modified exosomes (loaded) derived from control MSC, MSC, genetically modified MSC, MSC-NTF, or genetically modified-MSC-NTF cells, will reduce formation of α-synuclein inclusions and dopamine neuron loss in the cortex, hippocampus and amygdala of rats. Analysis may include: A. Immunohistochemistry with an antibody to phosphorylated α-synuclein and Nissl counterstaining and unbiased stereological counts of total number of cells and total number of phosphorylated α-synuclein inclusions in the cell bodies in the amygdala, substantia nigra pars compacta, striatum, hippocampus and cortex is performed; B. Immunohistochemistry for tyrosine hydroxylase in sections from the substantia nigra pars compacta. Perform stereology to count TH+ and Nissl+ neurons and immunofluorescence for dopamine transporter and TH in the striatum and quantify immunofluorescence signal to determine if there is a loss of dopaminergic terminals is performed; C. Behavior tests including open field test, cylinder test and ultrasonic vocalizations are performed to determine whether intrathecal delivery of MSC and MSC-NTF-derived exosomes reduces development of α-synuclein inclusion-induced behavioral defects; D. Immunofluorescence for MHCII, IBA-1, or CD163, or a combination thereof is used to determine whether intrathecal delivery of exosomes or modified exosomes (loaded) derived from MSC, genetically modified MSC, MSC-NTF, and modified MSC-NTF cells reduces inflammation caused by formation of α-synuclein inclusions in the cortex, hippocampus and amygdala of rats; and/or E Immunofluorescence for sCD27, chitinase 3-like-1 protein, chitinase 3-like-2 protein, or NfL, or a combination thereof is used to determine whether intrathecal delivery of exosomes or modified exosomes (loaded) derived from MSC, genetically modified MSC, MSC-NTF, and modified MSC-NTF cells reduces neuroinflammation caused by formation of α-synuclein inclusions in the cortex, hippocampus and amygdala of rats.

Conclusion: one of the beneficial attributes of exosomes isolated from MSC-NTF cells is their neuroprotective effect. This attribute can be utilized in fighting neurodegenerative diseases. Importantly, this attribute can be further augmented by loading the isolated exosomes with additional neuroprotective cargo molecules, as described in Example 2.

Example 4

Preparation of Differentiated Human BM-MSC (MSC-NTF) and Exosome Production & Purification Methods for isolation of human bone marrow-MSCs (BM-MSC) are well known in the art and fully described in e.g. International Patent Application Publication Nos. WO 2015/121859 and WO 2014/024183.

Bone marrow samples (50-100 ml) were collected into Heparin-containing tubes from the posterior iliac crest of healthy adult human donors by bone marrow aspiration. Bone marrow aspirates were diluted 1:1 with DMEM and mononuclear cells were separated by density centrifugation (1,000× G for 20 min), over Ficoll (Ficoll-Paque PREMIUM) containing tubes. The mononuclear cell fraction was collected and washed in DMEM. Cells were re-suspended in Growth Medium containing 10% Platelet lysate (PM; see below), counted by the Trypan blue exclusion dye and seeded at a concentration of up to 300,000 cells/cm$^2$ in 2-Chamber CellStacks. Flasks were incubated in a 37° C. humidified incubator with 5% $CO_2$.

PM growth medium consisted of Dulbecco's Modified Eagle's Medium low glucose (Sigma, Aldrich), supplemented with L-Glutamine solution 200 mM (Sigma, Aldrich), Sodium Pyruvate solution 100 mM (Sigma, Aldrich), 2 IU/ml Heparin (APP Pharmaceuticals), and 10% platelet lysate. 16-24 hours later PM medium was aspirated to remove non-adherent cells from the flask, adherent cells were washed gently with 10 ml of DMEM, and 30 ml of fresh PM were added to the flask. hMSC cells were allowed to proliferate for 12-15 days in PM medium, which was replaced two-three times a week. After 12-15 days or when the flask reached confluence. The cells were harvested by removing all growth medium and incubating in TrypLE™ solution (Invitrogen) for 5 min in a 37° C. incubator. Cells were then washed in DMEM, counted, and cryopreserved in 10% DMSO in PM at a concentration of $15 \times 10^6$ cells/ml/cryovial. Cryopreservation is in liquid nitrogen.

To avoid the need for repeated bone marrow aspirations, in some embodiments, MSC were cryopreserved at either passages P0, P1, or P2, and multiple fresh MSC-NTF cell doses were produced from the cryopreserved MSC, which were thawed and propagated prior to induction to MSC-NTF cells.

Thawed MSC cultures were resuspended in PM medium, and seeded in CellStacks at a density of 2000 cells/cm² and differentiation was induced four days later by replacing the growth medium (PM) with a serum free DMEM medium containing 1 mM of dibutyryl cyclic adenosine monophosphate, 20 ng/mL of human basic fibroblast growth factor, 5 ng/mL of human platelet-derived growth factor, and 50 ng/mL of human heregulin-β1 (S2M) for three additional days.

Then, culture medium from the above differentiated cells (MSC-NTF cells) was collected, and cell debris and large vesicles were removed by filtration through a 0.2-1.2-μm filter. The exosome containing filtrate was collected under sterile conditions and subjected to Tangential Flow Filtration (TFF; GE Healthcare Life Sciences).

Scale-Up MSC-NTF Cell Production and Exosome Production & Purification

For scaling-up exosomes manufacturing, secretion, and yield, thawed MSC cultures were resuspended in PM medium, and seeded in CellStacks for (several days') propagation. MSC were then harvested and re-seeded in a Cel-Cradle™ bioreactor bottle on BioNocII Macrocarriers (EscoVacciXcell, Singapore) at a density of 2,000-2,600 cells/cm² in 500 ml of PM for 4-6 days. PM was replaced after two days or circulated at a rate of 500-1500 ml/day using a perfusion system. In some embodiments, after four to six days PM was replaced with S2M for three or four days for inducing differentiation. At the end of the differentiation, or at multiple time points during the differentiation process the conditioned media was collected and cell debris and large vesicles were removed by filtration through a 0.2-1.2-μm filter. Multiple medium collections during the differentiation process increases the total exosome yield by up to 2-fold.

The exosome containing filtrate was collected under sterile conditions and subjected to Tangential Flow Filtration (TFF; GE Healthcare Life Sciences), with or without removing proteins from the solution using column-based size exclusion chromatography (SEC, GE Healthcare Life Sciences) or membrane chromatography. The yield of purified exosomes was in the range of about $3-4 \times 10^{11}$ which was up to about 4-5-fold the yield obtained from the process using CellStacks (about) $7 \times 10^{10}$.

Independent of the method used for exosome production and purification, control exosomes were produced from MSC cells using DMEM with 10% exosomes-depleted platelet lysate to avoid the possible confounding effect of platelet lysate derived exosomes.

In some instances, MSCs are expanded and differentiated into MSC-NTF cells in the Quantum cell expansion system. (Terumo BCT, USA) (The Quantum Cell Expansion System is an automated platform designed to simplify the open, labor-intensive tasks associated with manual cell culture).

Conditioned media are collected at the end of the differentiation process and are subjected to the above-mentioned exosome isolation procedures.

Exosomes Manufacturing Process:

Isolation of MSC-NTF Cell-Specific Exosomes

Tangential Flow Filtration (TFF)—either 100, 300, 500-kDa MWCO membranes were used (Spectrum Lab). The exosome-containing sample was continuously pumped through the fiber system and recirculated Small molecules, including free proteins not included within or associated with the membrane vesicles, were driven through the membrane pores, subsequently eluted as permeate, and eventually discarded. Molecules too large to pass through the pores, such as exosomes (or larger microvesicles), were kept in circulation as retentate. The sample was subjected to five rounds of diafiltration in order to further deplete the sample of contaminants smaller than the kDa MWCO membrane. During the last cycle of diafiltration, the sample was reduced to a volume of ~10 ml.

Size Exclusion Chromatography (SEC)—For high-purity exosomes, TFF was followed by SEC. Alternatively, SEC was not performed and a step of TFF was enough to isolate the exosomes.

Characterization of the purified exosomes was performed at several levels including quantification, phenotype and cargo content.

Figure 6:
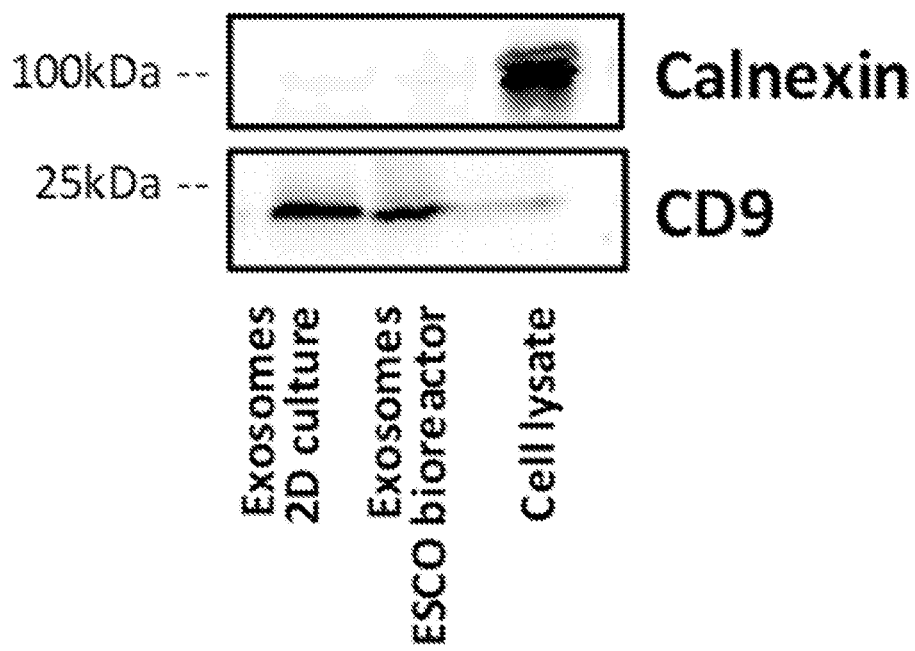
FIG. 6 shows the purity of exosomes isolated from 2D culture conditioned media of MSC-NTF cells and from bioreactor conditioned media of MSC-NTF cells, compared to MSC-NTF cell lysate, by Western-blot analysis for the exosome marker CD9 and the endoplasmic reticulum (ER) marker Calnexin.

MSC-NTF cell lysate (20 ug protein) and exosome lysates which were isolated from either 2D (CellStack) or bioreactor MSC-NTF conditioned media (20-40 ug protein) were analyzed by Western blot using mouse monoclonal antibodies to CD9 (diluted 1:500; Cat #CBL162 Merck) and Calnexin (diluted 1:500; MAB3126, Merck). Following incubation with HRP-conjugated goat anti-mouse IgG antibody (diluted 1:5000; Cat #AP308P, Merck) the membrane was developed using EZ-ECL solutions (Biological Industries). FIG. 6 illustrates the purity of exosomes produced by the different methods. Specifically, the high expression of the exosome marker CD9 and very low expression of the ER marker, Calnexin, in the exosome samples confirm the high purity of both exosome samples.

Exosomes isolated from MSC or MSC-NTF cells were analyzed for surface marker expression using the ExoView platform (Nanoview Diagnostics) which can detect nanoparticles bound to a chip surface through specific antibodies. Results illustrated in FIG. 7 indicate that both exosomes from MSC and MSC-NTF cells express the characteristic exosomal surface markers CD81, CD63 and CD9. The expression of MHCI or MHCII was low in both exosome populations. Mouse IgG was used as negative control.

In order to characterize the protein cargo in MSC-NTF derived exosomes and to compare their cargo with that of control MSC derived exosomes, an antibody array (Human Cytokine Array Q440, by Raybiotech) was used. This array can quantitively measure the expression of 440 proteins, including cytokines.

Figure 8:
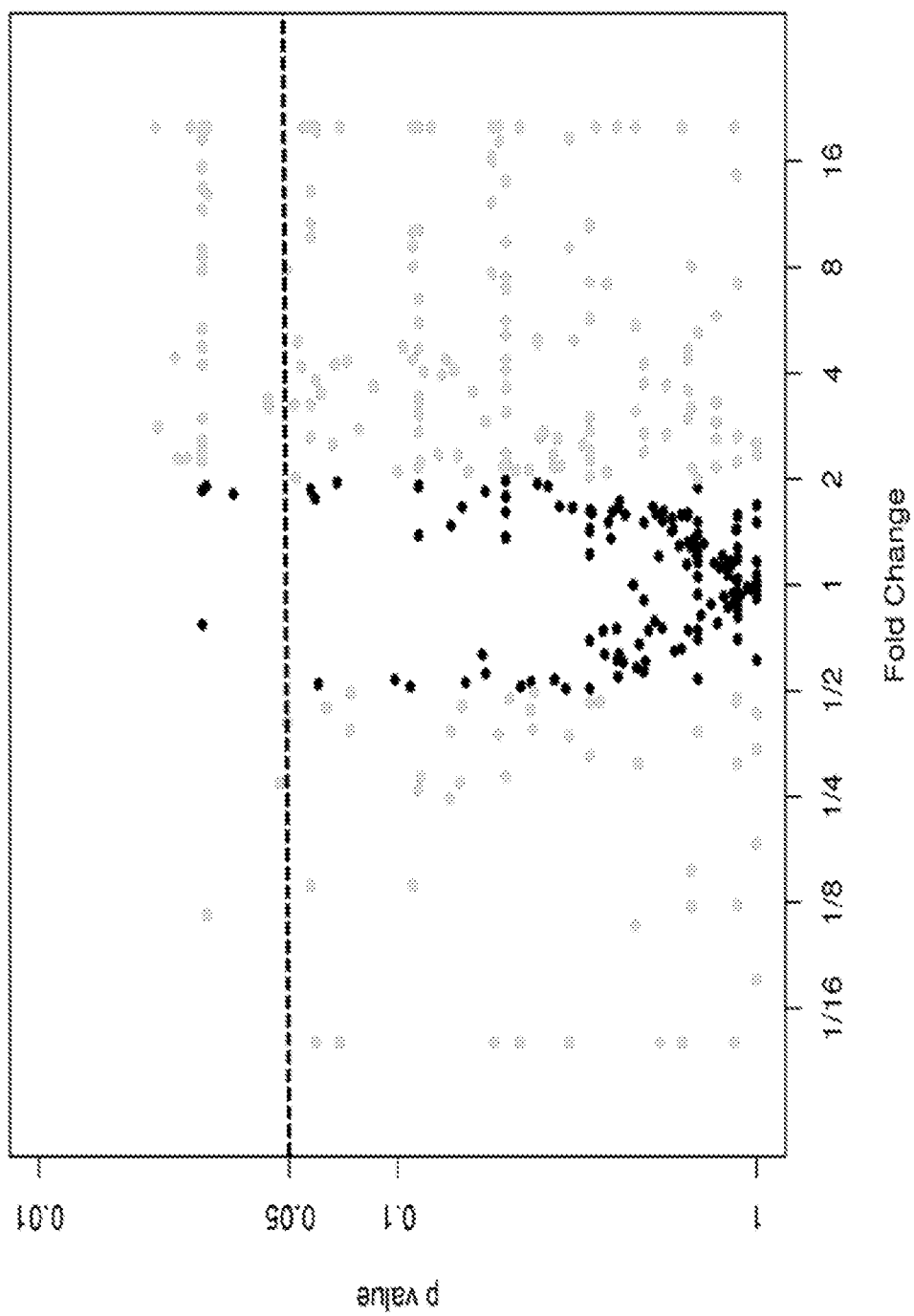
FIG. 8 is a Volcano plot of an antibody array data, comparing MSC and MSC-NTF derived exosomes. The data for all proteins is plotted as fold change (x axis) versus the p-value (y axis) in descending order. The threshold of a significant p-value (<0.05) is shown as dashed line. p-value was calculated using Wilcoxon or Student's t-test, depending on data distribution. Proteins of little change (0.5 to 2 fold) are marked as black spheres, proteins of large change (below 0.5 fold or above 2 fold) are marked as light green spheres.

Protein arrays of MSC (n=4) and MSC-NTF (n=4) derived exosomes showed that MSC-NTF derived exosomes had an increased content of 42 proteins (significance ($p<0.05$)) in compared with control MSC derived exosomes, while 4 proteins were significantly decreased in MSC-NTF derived exosomes. These proteins are listed in Table 1 and illustrated in FIG. 8.

TABLE 1

Proteins modulated in MSC-NTF derived exosomes vs. control MSC derived

| Protein | MSC derived exosomes (pg/ml) | MSC-NTF derived exosomes (pg/ml) | Fold Change |
|---|---|---|---|
| SPINT2 | 0 (0, 0) | 77.09 (10.37, 214.74) | 77090.77 |
| TNFSF14 | 0 (0, 2.53) | 29.52 (2.81, 48.8) | 29523.43 |
| IL36G | 0 (0, 0) | 10.37 (5.18, 89.58) | 10375.74 |
| TNFRSF10B | 0 (0, 0) | 4.44 (0.1, 19.19) | 4445.95 |
| IL36A | 9.18 (0, 202.26) | 2246.97 (403.46, 5107.29) | 244.89 |
| CCL7 | 1.47 (0.27, 2.9) | 94.43 (52.85, 293.11) | 64.12 |
| MMP10 | 0.69 (0, 4.02) | 43.8 (11.31, 108.93) | 63.61 |
| PIGF | 1.63 (0, 3.51) | 101.3 (49.95, 219.28) | 62.02 |
| CXCL8 | 2.03 (0.08, 3.99) | 123.49 (87.74, 290.65) | 60.86 |
| LTA | 3.38 (0, 61.46) | 176.43 (71.31, 511.73) | 52.25 |
| LIF | 1.35 (0, 2.7) | 69.29 (7.71, 227.81) | 51.5 |
| CXCL1 | 3.99 (0, 7.95) | 133.36 (44.16, 266.7) | 33.38 |
| CXCL6 | 31.63 (0.06, 34.95) | 861.22 (701.76, 1290.23) | 27.23 |
| MMP3 | 224.37 (0, 512.42) | 5592.18 (1711.54, 12122.95) | 24.92 |
| CHI3L1 | 111.84 (42.03, 220.77) | 2689.19 (845.91, 14301.22) | 24.04 |
| IL11 | 95.69 (17.64, 129.96) | 2130.81 (1320.08, 4939.7) | 22.27 |
| FGF2 | 50.04 (6.69, 70.06) | 1036.66 (520.24, 3264.96) | 20.72 |
| CXCL5 | 19.28 (2.98, 39.51) | 374.15 (193.66, 586.16) | 19.41 |
| GAS1 | 3.21 (2.01, 6.74) | 59.35 (22.96, 185.67) | 18.51 |
| JAML | 56.41 (0, 201.37) | 869.05 (255.68, 3425.15) | 15.41 |
| TGFBR3 | 44.75 (15.37, 88.77) | 602.39 (166.03, 1177.34) | 13.46 |
| MEPE | 1.17 (0, 3.42) | 15.08 (5.38, 41.83) | 12.86 |
| IL6 | 403.42 (142.77, 557.98) | 4705.22 (1772.24, 10752.01) | 11.66 |
| PDGFA | 33.55 (3.62, 58.16) | 301.62 (185.37, 797.11) | 8.99 |
| CCL4 | 7.05 (4.43, 16.03) | 59.97 (47.74, 193.62) | 8.5 |
| CCL21 | 178.02 (3.89, 187.1) | 1397.78 (744.39, 2053.74) | 7.85 |
| IL13 | 72.13 ± 93.76 | 563.96 ± 319.38 | 7.82 |
| VEGFA | 179.04 (114.64, 191.93) | 958.14 (344.01, 1518.78) | 5.35 |
| CCL2 | 62.82 (23.56, 87.13) | 298.13 (206.28, 776.84) | 4.75 |
| MIF | 186.63 ± 107.29 | 823.83 ± 324.6 | 4.41 |
| GDF15 | 13.99 (0.61, 21.25) | 59.09 (25.8, 892.19) | 4.22 |
| PLAU | 855.86 ± 614.4 | 2887.03 ± 1294.71 | 3.37 |
| ANGPTL4 | 2733.88 ± 3156.6 | 8730.48 ± 3478.53 | 3.19 |
| CTSB | 1294.9 (136.7, 2046.52) | 3848.03 (3450.95, 9848) | 2.97 |
| BSG | 271.93 ± 128.8 | 763.92 ± 252.65 | 2.81 |
| CCL5 | 564.6 (393.17, 952.69) | 1450.97 (1315.12, 4028.11) | 2.57 |
| TPO | 439.13 (361.36, 621.12) | 1053.65 (902.25, 2053.88) | 2.4 |
| IL23 | 264.05 ± 155.07 | 604.74 ± 170.89 | 2.29 |
| IL1RL1 | 74.18 ± 38.51 | 168.96 ± 49.02 | 2.28 |
| SPP1 | 4965.71 (4097.8, 5558.03) | 11205.31 (7999.76, 19980.46) | 2.26 |
| F11R | 44.97 ± 12.63 | 85.88 ± 23.08 | 1.91 |
| INHBA | 1940.18 (1342.74, 1995.82) | 3607.83 (2127.15, 5991.64) | 1.86 |
| FAP | 3405.6 ± 498.74 | 6176.57 ± 1596.01 | 1.81 |
| LYVE1 | 1321.54 (1241.35, 1499.62) | 1018.88 (511.04, 1227.35) | 0.77 |
| FRZB | 5472.27 ± 2107.87 | 2223.38 ± 1456.01 | 0.41 |
| CCL11 | 1.77 ± 0.83 | 0.49 ± 0.57 | 0.27 |
| C5a | 2476.45 (831.23, 4047.13) | 285.25 (0, 715.8) | 0.12 |

Exosomes

Table 1 provides as list of proteins (protein sample concentration 950 ug/ml) which were significantly (p<0.05) increased (>1) or decreased (<1) in MSC-NTF derived exosomes vs. control MSC derived exosomes (pg/ml, Mean±SD or median (min, max) depending on normality of data distribution). Mean±SD is provided for normal distribution data and median (min, max) for when normality is not assumed. Protein names are standard protein nomenclature.

Conclusion: A unique population of exosomes may be isolated from MSC-NTF cells compared to exosomes isolated from MSC cells. This unique population of exosomes carries a markedly different protein cargo profile. This difference makes MSC-NTF exosomes a different entity and a different therapeutic agent than MSC exosomes. Interestingly, increased cargo profiles were observed for protein candidates considered helpful in treating neurodegenerative conditions, including but not limited to neurotrophic factors LIF, GDF15, and VEGFA. Other cargo proteins considered helpful included but were not limited to CXCL1 and IL13.

Example 5

Protective Effect of MSC-NTF Exosomes in Parkinson's Disease

To study the protective effect of exosomes on the function of dopaminergic neurons in an animal model of Parkinson's disease (PD), MSC-NTF exosomes are evaluated in the AAV1/2 human A53T alpha synuclein (AAVhA53TaSyn) rat model of PD empirically determined to produce significant behavioral and dopaminergic nigrostriatal deficits between 3 and 6 weeks following surgical delivery (Koprich et al, PLoS One, 2011 Mar. 7; 6(3):e17698).

This model employs an AAV1/2 gene delivery system to deliver human mutated A53T-alpha-synuclein (AAV hA53T aSyn) to drive a unilateral synucleinopathy that models, in rat, the disease process responsible for dopaminergic degeneration in PD. With this model, over-expression of alpha synuclein throughout the nigrostriatal pathway and Lewy-like pathology develops. Moreover, this synucleinopathy produces a deficit of 35-45% in striatal dopamine and 35-40% in nigral dopamine neurons. To establish the model AAV hA53T aSyn vectors are administered unilaterally into the right substantia nigra (SN) by stereotaxis surgery on day 1 (D1).

Biodistribution Study

To pre-determine the in-vivo distribution of exosomes, in the alpha synuclein rat model of PD, 100 ul of MSC-NTF exosomes (about 109 particles) are stained with boron-dipyrromethene (BODIPY TR, 1 uM, Invitrogen) for 20 min at 37° C. Free dye is removed using Exosome spin column (MW 3000, Invitrogen). To confirm exosome staining, stained exosomes are added to the culture medium of SH-SY5Y cells for 4 hours, and washed once with PBS. Images are captured using the Incucyte S3 imaging system 24 hours after exosome addition. Control staining is performed without exosomes, using dye only, which is cleaned using the exosome spin column. 24 hours after exosome addition, a strong and specific fluorescent signal is observed in 100% of the cells, that is absent in control cells stained with dye only.

To assess the in-vivo biodistribution of exosomes, MSC-NTF exosomes fluorescently labeled with BODIPY, are injected in the rat alpha-synuclein model for three days (Days 7-10 from aSyn vectors administration) by iPrecio pumps (Primetech) adjusted to deliver the exosomes at a rate of 1 ul/hour. Six animals (female Sprague-Dawley rats) are injected with stained exosomes from MSC-NTF cells after AAV1/2 surgery, and 6 animals are injected with exosomes without AAV1/2 surgery to compare the biodistribution pattern of exosomes in a healthy animal. On D11, 24 h following the end of the 3-day infusion period of the exosomes, animals are sacrificed for postmortem analyses and for assessment of biodistribution.

Brain tissue sections of interest are first evaluated for the presence of the label and to determine whether the fluorescent label is within neurons and/or glia in the rat alpha synuclein model of Parkinson's disease.

Efficacy Study

The in-vivo protective effect of exosomes in the rat alpha synuclein model is evaluated in a 4-animal group study, 12 animals/group. One control group, is injected on day 1 with an empty vector, and three groups are injected with the AAV hA53T aSyn carrying vector. MSC and MSC-NTF exosomes (groups 3 and 4 respectively) are administered (i.c.v.) on days 7 (D7), D22 and D32 by iPrecio pumps (Primetech) adjusted to deliver exosomes continuously for 3 days at a rate of 1 ul/hour at each timepoint). The control groups are given sterile PBS.

Behavioral assessment is conducted in the cylinder test, to assess forelimb asymmetry, prior to surgery (baseline, D-3), 3 weeks following AAV administration (D21) and 6 weeks following AAV administration (D42).

Animals are killed on D43 for post mortem assessments including assessment of striatal dopamine and metabolite levels (via liquid chromatography-mass spectometry LC/MS), dopamine transporter (DAT) levels (by[11c]RTI-121 autoradiography), total striatal human (transgene-derived) alpha synuclein expression (by ELISA) and assessment of number of tyrosine hydroxylase positive (TH+ve) cells in the substantia nigra pars compacta (SNc). Additional parameters are then evaluated including, assessment of microglia activation and determining the ratio of TH+/pSer129 aSyn+ to TH+/pSer129aSyn− neurons in the SN by double label counting stereology.

Conclusion: MSC-NTF exosomes have at least two advantages as therapeutic agents in fighting e.g. Parkinson's disease. First, they have a pronounced neuroprotective effect, and second, due to their size, they readily cross the blood-brain bather, which allows their administration to be systematic, and not necessarily intra-cranial.

Example 6

Effects of MSC-NTF Exosomes by RNA Sequencing

To study genes and pathways that are regulated in neurons by MSC-NTF cells' exosomes, neural progenitor cells derived from iPSCs (Stemcell Technologies) were differentiated into mature neurons for 14 days using neuron differentiation and maturation medium (Stemcell Technologies Cat #70901). On day 15 medium was replaced with neurotrophic factor deprived medium, supplemented with exosomes ($2-4 \times 10^9$ particles) or with PBS. 3 days after treatment, total RNA was isolated using a mini RNA isolation kit (Zymo Research) from the cells. Next-generation sequencing (NGS) was performed using NextSeq500 (Illumina) A total of 3687 differentially expressed genes (DEGs) were identified (p-adj<0.05). The top upregulated genes, and top downregulated genes are summarized in Table 2 (p-adj<0.05)("NA"—Not available; "Novel transcript"—newly-identified transcript). The list of DEGs was analyzed for pathway enrichment using the WebGestalt tool. The enriched KEGG (Kyoto Encyclopedia of Genes and Genomes) pathways (in Homo sapiens (human)) showing a significant effect of exosomes on modulation of extracellular matrix and adhesion proteins is summarized in Table 3.

Table 2.

TABLE 2

The Top Upregulated Genes and Top Downregulated Genes.

| Genes* upregulated in exosomes vs. PBS | Gene symbol | Annotation |
| --- | --- | --- |
| "ENSG00000204711" | "C9orf135" | chromosome 9 open reading frame 135 [Source: HGNC Symbol; Acc: HGNC:31422] |
| "ENSG00000134668" | "SPOCD1" | SPOC domain containing 1 [Source: HGNC Symbol; Acc: HGNC:26338] |
| "ENSG00000175899" | "A2M" | alpha-2-macroglobulin [Source: HGNC Symbol; Acc: HGNC:7] |
| "ENSG00000278910" | NA | BRAF-activated non-protein coding RNA [Source: HGNC Symbol; Acc: HGNC:43877] |
| "ENSG00000131095" | "GFAP" | glial fibrillary acidic protein [Source: HGNC Symbol; Acc: HGNC:4235] |
| "ENSG00000102359" | "SRPX2" | sushi repeat containing protein X-linked 2 [Source: HGNC Symbol; Acc: HGNC:30668] |
| "ENSG00000261371" | "PECAM1" | platelet and endothelial cell adhesion molecule 1 [Source: HGNC Symbol; Acc: HGNC:8823] |

TABLE 2-continued

The Top Upregulated Genes and Top Downregulated Genes.

| | | |
|---|---|---|
| "ENSG00000091583" | "APOH" | apolipoprotein H [Source: HGNC Symbol; Acc: HGNC:616] |
| "ENSG00000197632" | "SERPINB2" | serpin family B member 2 [Source: HGNC Symbol; Acc: HGNC:8584] |
| "ENSG00000113263" | "ITK" | IL2 inducible T cell kinase [Source: HGNC Symbol; Acc: HGNC:6171] |
| "ENSG00000250993" | NA | novel transcript |
| "ENSG00000259070" | "LINC00639" | long intergenic non-protein coding RNA 639 [Source: HGNC Symbol; Acc: HGNC:27502] |
| "ENSG00000117318" | "ID3" | inhibitor of DNA binding 3 HLH protein [Source: HGNC Symbol; Acc: HGNC:5362] |
| "ENSG00000266928" | NA | novel transcript |
| "ENSG00000196639" | "HRH1" | histamine receptor H1 [Source: HGNC Symbol; Acc: HGNC:5182] |
| "ENSG00000164850" | "GPER1" | G protein-coupled estrogen receptor 1 [Source: HGNC Symbol; Acc: HGNC:4485] |
| "ENSG00000188404" | "SELL" | selectin L [Source: HGNC Symbol; Acc: HGNC:10720] |
| "ENSG00000105825" | "TFPI2" | tissue factor pathway inhibitor 2 [Source: HGNC Symbol; Acc: HGNC:11761] |
| "ENSG00000198796" | "ALPK2" | alpha kinase 2 [Source: HGNC Symbol; Acc: HGNC:20565] |
| "ENSG00000165899" | "OTOGL" | otogelin like [Source: HGNC Symbol; Acc: HGNC:26901] |
| "ENSG00000204277" | "LINC01993" | long intergenic non-protein coding RNA 1993 [Source: HGNC Symbol; Acc: HGNC:52826] |
| "ENSG00000142748" | "FCN3" | ficolin 3 [Source: HGNC Symbol; Acc: HGNC:3625] |
| "ENSG00000248461" | "LINC02119" | long intergenic non-protein coding RNA 2119 [Source: HGNC Symbol; Acc: HGNC:52975] |
| "ENSG00000188501" | "LCTL" | lactase like [Source: HGNC Symbol; Acc: HGNC:15583] |
| "ENSG00000250538" | "LOC107986321" | novel transcript |
| "ENSG00000136869" | "TLR4" | toll like receptor 4 [Source: HGNC Symbol; Acc: HGNC:11850] |
| "ENSG00000125968" | "ID1" | inhibitor of DNA binding 1 HLH protein [Source: HGNC Symbol; Acc: HGNC:5360] |
| "ENSG00000131094" | "C1QL1" | complement C1q like 1 [Source: HGNC Symbol; Acc: HGNC:24182] |
| "ENSG00000105559" | "PLEKHA4" | pleckstrin homology domain containing A4 [Source: HGNC Symbol; Acc: HGNC:14339] |
| "ENSG00000135547" | "HEY2" | hes related family bHLH transcription factor with YRPWmotif2 [Source: HGNC Symbol; Acc: HGNC:4881] |
| "ENSG00000140853" | "NLRC5" | NLR family CARD domain containing 5 [Source: HGNC Symbol; Acc: HGNC:29933] |
| "ENSG00000134531" | "EMP1" | epithelial membrane protein 1 [Source: HGNC Symbol; Acc: HGNC:3333] |
| "ENSG00000108691" | "CCL2" | C-C motif chemokine ligand 2 [Source: HGNC Symbol; Acc: HGNC:10618] |
| "ENSG00000235884" | "LINC00941" | long intergenic non-protein coding RNA 941 [Source: HGNC Symbol; Acc: HGNC:48635] |
| "ENSG00000205403" | "CFI" | complement factor I [Source: HGNC Symbol; Acc: HGNC:5394] |
| "ENSG00000267280" | "TBX2-AS1" | TBX2 antisense RNA 1 [Source: HGNC Symbol; Acc: HGNC:50355] |
| "ENSG00000165985" | "C1QL3" | complement C1q like 3 [Source: HGNC Symbol; Acc: HGNC:19359] |
| "ENSG00000172548" | "NIPAL4" | NIPA like domain containing 4 [Source: HGNC Symbol; Acc: HGNC:28018] |
| "ENSG00000257446" | "ZNF878" | zinc finger protein 878 [Source: HGNC Symbol; Acc: HGNC:37246] |
| "ENSG00000180801" | "ARSJ" | arylsulfatase family member J [Source: HGNC Symbol; Acc: HGNC:26286] |
| "ENSG00000138798" | "EGF" | epidermal growth factor [Source: HGNC Symbol; Acc: HGNC:3229] |
| "ENSG00000116745" | "RPE65" | RPE65 retinoid isomerohydrolase [Source: HGNC Symbol; Acc: HGNC:10294] |
| "ENSG00000107984" | "DKK1" | dickkopf WNT signaling pathway inhibitor 1 [Source: HGNC Symbol; Acc: HGNC:2891] |
| "ENSG00000122585" | "NPY" | neuropeptide Y [Source: HGNC Symbol; Acc: HGNC:7955] |
| "ENSG00000128283" | "CDC42EP1" | CDC42 effector protein 1 [Source: HGNC Symbol; Acc: HGNC:17014] |
| "ENSG00000089327" | "FXYD5" | FXYD domain containing ion transport regulator 5 [Source: HGNC Symbol; Acc: HGNC:4029] |
| "ENSG00000139155" | "SLCO1C1" | solute carrier organic anion transporter family member 1C1 [Source: HGNC Symbol; Acc: HGNC:13819] |

TABLE 2-continued

The Top Upregulated Genes and Top Downregulated Genes.

| | | |
|---|---|---|
| "ENSG00000183691" | "NOG" | noggin [Source: HGNC Symbol; Acc: HGNC:7866] |
| "ENSG00000147041" | "SYTL5" | synaptotagmin like 5 [Source: HGNC Symbol; Acc: HGNC:15589] |
| "ENSG00000184557" | "SOCS3" | suppressor of cytokine signaling 3 [Source: HGNC Symbol; Acc: HGNC:19391] |
| "ENSG00000121068" | "TBX2" | T-box2 [Source: HGNC Symbol; Acc: HGNC:11597] |
| "ENSG00000101825" | "MXRA5" | matrix remodeling associated 5 [Source: HGNC Symbol; Acc: HGNC:7539] |
| "ENSG00000137834" | "SMAD6" | SMAD family member 6 [Source: HGNC Symbol; Acc: HGNC:6772] |
| "ENSG00000087510" | "TFAP2C" | transcription factor AP-2 gamma [Source: HGNC Symbol; Acc: HGNC:11744] |
| "ENSG00000185149" | "NPY2R" | neuropeptide Y receptor Y2 [Source: HGNC Symbol; Acc: HGNC:7957] |
| "ENSG00000163251" | "FZD5" | frizzled class receptor 5 [Source: HGNC Symbol; Acc: HGNC:4043] |
| "ENSG00000153976" | "HS3ST3B1" | heparan sulfate-glucosamine 3-sulfotransferase 3A1 [Source: HGNC Symbol; Acc: HGNC:5196] |
| "ENSG00000099860" | "GADD45B" | growth arrest and DNA damage inducible beta [Source: HGNC Symbol; Acc: HGNC:4096] |
| "ENSG00000106366" | "SERPINE1" | serpin family E member 1 [Source: HGNC Symbol; Acc: HGNC:8583] |
| "ENSG00000128342" | "LIF" | LIF interleukin 6 family cytokine [Source: HGNC Symbol; Acc: HGNC:6596] |
| "ENSG00000026508" | "CD44" | CD44 molecule (Indian blood group) [Source: HGNC Symbol; Acc: HGNC:1681] |
| "ENSG00000164488" | "DACT2" | 110emaphorin binding antagonist of beta catenin 2 [Source: HGNC Symbol; Acc: HGNC:21231] |
| "ENSG00000109099" | "PMP22" | peripheral myelin protein 22 [Source: HGNC Symbol; Acc: HGNC:9118] |
| "ENSG00000177337" | NA | DLGAP1 antisense RNA 1 [Source: HGNC Symbol; Acc: HGNC:31676] |
| "ENSG00000168874" | "ATOH8" | atonal bHLH transcription factor 8 [Source: HGNC Symbol; Acc: HGNC:24126] |
| "ENSG00000262001" | NA | DLGAP1 antisense RNA 2 [Source: HGNC Symbol; Acc: HGNC:28146] |
| "ENSG00000175445" | "LPL" | lipoprotein lipase [Source: HGNC Symbol; Acc: HGNC:6677] |
| "ENSG00000131203" | "IDO1" | indoleamine 2 3-dioxygenase 1 [Source: HGNC Symbol; Acc: HGNC:6059] |
| "ENSG00000268O89" | "GABRQ" | gamma-aminobutyric acid type A receptor theta subunit [Source: HGNC Symbol; Acc: HGNC:14454] |
| "ENSG00000138316" | "ADAMTS14" | ADAM metallopeptidase with thrombospondin type 1 motif 14 [Source: HGNC Symbol; Acc: HGNC:14899] |
| "ENSG00000122420" | "PTGFR" | prostaglandin F receptor [Source: HGNC Symbol; Acc: HGNC:9600] |
| "ENSG00000167306" | "MYO5B" | myosin VB [Source: HGNC Symbol; Acc: HGNC:7603] |
| "ENSG00000109846" | "CRYAB" | crystallin alpha B [Source: HGNC Symbol; Acc: HGNC:2389] |
| "ENSG00000131724" | "IL13RA1" | interleukin 13 receptor subunit alpha 1 [Source: HGNC Symbol; Acc: HGNC:5974] |
| "ENSG00000106823" | "ECM2" | extracellular matrix protein 2 [Source: HGNC Symbol; Acc: HGNC:3154] |
| "ENSG00000142089" | "IFITM3" | interferon induced transmembrane protein 3 [Source: HGNC Symbol; Acc: HGNC:5414] |
| "ENSG00000100311" | "PDGFB" | platelet derived growth factor subunit B [Source: HGNC Symbol; Acc: HGNC:8800] |
| "ENSG00000222041" | "CYTOR" | cytoskeleton regulator RNA [Source: HGNC Symbol; Acc: HGNC:28717] |
| "ENSG00000267519" | "LOC284454" | novel transcript |
| "ENSG00000152049" | "KCNE4" | potassium voltage-gated channel subfamily E regulatory subunit 4 [Source: HGNC Symbol; Acc: HGNC:6244] |
| "ENSG00000115844" | "DLX2" | distal-less homeobox 2 [Source: HGNC Symbol; Acc: HGNC:2915] |
| "ENSG00000172965" | "CYTOR" | MIR4435-2 host gene [Source: HGNC Symbol; Acc: HGNC:35163] |
| "ENSG00000197467" | "COL13A1" | collagen type XIII alpha 1 chain [Source: HGNC Symbol; Acc: HGNC:2190] |
| "ENSG00000203805" | "PLPP4" | phospholipid phosphatase 4 [Source: HGNC Symbol; Acc: HGNC:23531] |
| "ENSG00000183230" | "CTNNA3" | catenin alpha 3 [Source: HGNC Symbol; Acc: HGNC:2511] |
| "ENSG00000154274" | "C4orf19" | chromosome 4 open reading frame 19 [Source: HGNC Symbol; Acc: HGNC:25618] |
| "ENSG00000121236" | "TRIM6" | tripartite motif containing 6 [Source: HGNC Symbol; Acc: HGNC:16277] |

TABLE 2-continued

The Top Upregulated Genes and Top Downregulated Genes.

| | | |
|---|---|---|
| "ENSG00000177359" | "OVOS2" | alpha-2-macroglobulin like 1 pseudogene [Source: NCBI gene; Acc: 144203] |
| "ENSG00000166106" | "ADAMTS15" | ADAM metallopeptidase with thrombospondin type 1 motif 15 [Source: HGNC Symbol; Acc: HGNC: 16305] |
| "ENSG00000145623" | "OSMR" | oncostatin M receptor [Source: HGNC Symbol; Acc: HGNC:8507] |
| "ENSG00000182601" | "HS3ST4" | heparan sulfate-glucosamine 3-sulfotransferase 4 [Source: HGNC Symbol; Acc: HGNC:5200] |
| "ENSG00000213694" | "S1PR3" | sphingosine-1-phosphate receptor 3 [Source: HGNC Symbol; Acc: HGNC:3167] |
| "ENSG00000005059" | "MCUB" | mitochondrial calcium uniporter dominant negative beta subunit [Source: HGNC Symbol; Acc: HGNC:26076] |
| "ENSG00000078081" | "LAMP3" | lysosomal associated membrane protein 3 [Source: HGNC Symbol; Acc: HGNC:14582] |
| "ENSG00000135406" | "PRPH" | peripherin [Source: HGNC Symbol; Acc: HGNC:9461 ] |
| "ENSG00000138496" | "PARP9" | poly(ADP-ribose) polymerase family member 9 [Source: HGNC Symbol; Acc: HGNC:24118] |
| "ENSG00000116132" | "PRRX1" | paired related homeobox 1 [Source: HGNC Symbol; Acc: HGNC:9142] |
| "ENSG00000105974" | "CAV1" | caveolin 1 [Source: HGNC Symbol; Acc: HGNC:1527] |
| "ENSG00000138829" | "FBN2" | fibrillin 2 [Source: HGNC Symbol; Acc: HGNC:3604] |
| "ENSG00000119917" | "IFIT3" | interferon induced protein with tetratricopeptide repeats 3 [Source: HGNC Symbol; Acc: HGNC:5411] |
| "ENSG00000110852" | "CLEC2B" | C-type lectin domain family 2 member B [Source: HGNC Symbol; Acc: HGNC:2053] |

| Genes downregulated in exosomes vs. PBS (p-adj < 0.05) | gene symbol | Annotation |
|---|---|---|
| "ENSG00000262484" | "CCER2" | coiled-coil glutamate rich protein 2 [Source: HGNC Symbol; Acc: HGNC:44662] |
| "ENSG00000080644" | "CHRNA3" | cholinergic receptor nicotinic alpha 3 subunit [Source: HGNC Symbol; Acc: HGNC:1957] |
| "ENSG00000197847" | "SLC22A20P" | solute carrier family 22 member 20 pseudogene [Source: HGNC Symbol; Acc: HGNC:29867] |
| "ENSG00000213654" | "GPSM3" | G protein signaling modulator 3 [Source: HGNC Symbol; Acc: HGNC: 13945] |
| "ENSG00000203688" | "LINC02487" | long intergenic non-protein coding RNA 2487 [Source: HGNC Symbol; Acc: HGNC:53466] |
| "ENSG00000196218" | "RYR1" | ryanodine receptor 1 [Source: HGNC Symbol; Acc: HGNC:10483] |
| "ENSG00000221818" | "EBF2" | early B cell factor 2 [Source: HGNC Symbol; Acc: HGNC:19090] |
| "ENSG00000106327" | "TFR2" | transferrin receptor 2 [Source: HGNC Symbol; Acc: HGNC:11762] |
| "ENSG00000279232" | NA | novel transcript antisense to RGMB |
| "ENSG00000144485" | "HES6" | hes family bHLH transcription factor 6 [Source: HGNC Symbol; Acc: HGNC: 18254] |
| "ENSG00000260941" | "LINC00622" | long intergenic non-protein coding RNA 622 [Source: HGNC Symbol; Acc: HGNC:44251] |
| "ENSG00000215595" | "C20orf202" | chromosome 20 open reading frame 202 [Source: HGNC Symbol; Acc: HGNC:37254] |
| "ENSG00000251161" | NA | novel transcript |
| "ENSG00000182348" | "ZNF804B" | zinc finger protein 804B [Source: HGNC Symbol; Acc: HGNC:21958] |
| "ENSG00000131480" | "AOC2" | amine oxidase copper containing 2 [Source: HGNC Symbol; Acc: HGNC:549] |
| "ENSG00000245904" | NA | uncharacterized LOC101928617 [Source: NCBI gene; Acc: 101928617] |
| "ENSG00000143355" | "LHX9" | LIM homeobox 9 [Source: HGNC Symbol; Acc: HGNC:14222] |
| "ENSG00000089847" | "ANKRD24" | ankyrin repeat domain 24 [Source: HGNC Symbol; Acc: HGNC:29424] |
| "ENSG00000258701" | "LINC00638" | long intergenic non-protein coding RNA 638 [Source: HGNC Symbol; Acc: HGNC:28325] |
| "ENSG00000205038" | "PKHD1L1" | PKHD1 like 1 [Source: HGNC Symbol; Acc: HGNC:20313] |
| "ENSG00000224420" | "ADM5" | adrenomedullin 5 (putative) [Source: HGNC Symbol; Acc: HGNC:27293] |
| "ENSG00000276445" | NA | novel transcript |
| "ENSG00000099139" | "PCSK5" | proprotein convertase subtilisin/kexin type 5 [Source: HGNC Symbol; Acc: HGNC:8747] |
| "ENSG00000244151" | NA | novel transcript |
| "ENSG00000135248" | "FAM71F1" | family with sequence similarity 71 member F1 [Source: HGNC Symbol; Acc: HGNC:30704] |

TABLE 2-continued

The Top Upregulated Genes and Top Downregulated Genes.

| | | |
|---|---|---|
| "ENSG00000162692" | "VCAM1" | vascular cell adhesion molecule 1 [Source: HGNC Symbol; Acc: HGNC:12663] |
| "ENSG00000204839" | "MROH6" | maestro heat like repeat family member 6 [Source: HGNC Symbol; Acc: HGNC:27814] |
| "ENSG00000196104" | "SPOCK3" | SPARC (osteonectin) cwcv and kazal like domains proteoglycan 3 [Source: HGNC Symbol; Acc: HGNC:13565] |
| "ENSG00000143110" | "C1orf162" | chromosome 1 open reading frame 162 [Source: HGNC Symbol; Acc: HGNC:28344] |
| "ENSG00000133246" | "PRAM1" | PML-RARA regulated adaptor molecule 1 [Source: HGNC Symbol; Acc: HGNC:30091] |
| "ENSG00000179846" | "NKPD1" | NTPase KAP family P-loop domain containing 1 [Source: HGNC Symbol; Acc: HGNC:24739] |
| "ENSG00000198105" | "ZNF248" | zinc finger protein 248 [Source: HGNC Symbol; Acc: HGNC:13041] |
| "ENSG00000215475" | "SIAH3" | siah E3 ubiquitin protein ligase family member 3 [Source: HGNC Symbol; Acc: HGNC:30553] |
| "ENSG00000197584" | "KCNMB2" | potassium calcium-activated channel subfamily M regulatory beta subunit 2 [Source: HGNC Symbol; Acc: HGNC:6286] |
| "ENSG00000170381" | "SEMA3E" | 11 Semaphoring 3E [Source: HGNC Symbol; Acc: HGNC:10727] |
| "ENSG00000100346" | "CACNA1I" | calcium voltage-gated channel subunit alpha1 I [Source: HGNC Symbol; Acc: HGNC:1396] |
| "ENSG00000171786" | "NHLH1" | nescient helix-loop-helix 1 [Source: HGNC Symbol; Acc: HGNC:7817] |
| "ENSG00000244242" | "IFITM10" | interferon induced transmembrane protein 10 [Source:HGNC Symbol;Acc:HGNC:40022] |
| "ENSG00000280422" | NA | TEC |
| "ENSG00000102057" | "KCND1" | potassium voltage-gated channel subfamily D member 1 [Source: HGNC Symbol; Acc: HGNC:6237] |
| "ENSG00000091536" | "MYO15A" | myosin XVA [Source: HGNC Symbol; Acc: HGNC:7594] |
| "ENSG00000100024" | "UPB1" | beta-ureidopropionase 1 [Source: HGNC Symbol; Acc: HGNC:16297] |
| "ENSG00000130222" | "GADD45G" | growth arrest and DNA damage inducible gamma [Source: HGNC Symbol; Acc: HGNC:4097] |
| "ENSG00000168952" | "STXBP6" | syntaxin binding protein 6 [Source: HGNC Symbol; Acc: HGNC:19666] |
| "ENSG00000111644" | "ACRBP" | acrosin binding protein [Source: HGNC Symbol; Acc: HGNC:17195] |
| "ENSG00000115556" | "PLCD4" | phospholipase C delta 4 [Source: HGNC Symbol; Acc: HGNC:9062] |
| "ENSG00000180422" | "LINC00304" | long intergenic non-protein coding RNA 304 [Source: HGNC Symbol; Acc: HGNC:26713] |
| "ENSG00000007372" | "PAX6" | paired box 6 [Source: HGNC Symbol; Acc: HGNC:8620] |
| "ENSG00000272449" | NA | novel transcript |
| "ENSG00000038295" | "TLL1" | tolloid like 1 [Source: HGNC Symbol; Acc: HGNC:11843] |
| "ENSG00000262223" | NA | uncharacterized LOC100130370 [Source: NCBI gene; Acc: 100130370] |
| "ENSG00000111218" | "PRMT8" | protein arginine methyltransferase 8 [Source: HGNC Symbol; Acc: HGNC:5188] |
| "ENSG00000272549" | "LINC02538" | long intergenic non-protein coding RNA 2538 [Source: HGNC Symbol; Acc: HGNC:53571] |
| "ENSG00000172828" | "CES3" | carboxylesterase 3 [Source: HGNC Symbol; Acc: HGNC:1865] |
| "ENSG00000107736" | "CDH23" | cadherin related 23 [Source: HGNC Symbol; Acc: HGNC:13733] |
| "ENSG00000166359" | "WDR88" | WD repeat domain 88 [Source: HGNC Symbol; Acc: HGNC:26999] |
| "ENSG00000268041" | "LOC390937" | Ets2 repressor factor-like [Source: NCBI gene; Acc: 390937] |
| "ENSG00000099769" | "IGFALS" | insulin like growth factor binding protein acid labile subunit [Source: HGNC Symbol; Acc: HGNC:5468] |
| "ENSG00000233198" | "RNF224" | ring finger protein 224 [Source: HGNC Symbol; Acc: HGNC:41912] |
| "ENSG00000280229" | NA | TEC |
| "ENSG00000172232" | "AZU1" | azurocidin 1 [Source: HGNC Symbol; Acc: HGNC:913] |
| "ENSG00000131471" | "AOC3" | amine oxidase copper containing 3 [Source: HGNC Symbol; Acc: HGNC:550] |
| "ENSG00000260695" | NA | novel transcript |
| "ENSG00000255031" | NA | novel transcript antisense to CHKA |
| "ENSG00000180549" | "FUT7" | fucosyltransferase 7 [Source: HGNC Symbol; Acc: HGNC:4018] |

TABLE 2-continued

The Top Upregulated Genes and Top Downregulated Genes.

| | | |
|---|---|---|
| "ENSG00000169836" | "TACR3" | tachykinin receptor 3 [Source: HGNC Symbol; Acc: HGNC:11528] |
| "ENSG00000260978" | NA | MKRN3 antisense RNA 1 |
| "ENSG00000134595" | "SOX3" | SRY-box3 [Source: HGNC Symbol; Acc: HGNC:11199] |
| "ENSG00000270393" | NA | POM121 transmembrane nucleoporin (POM121) pseudogene |
| "ENSG00000188425" | "NANOS2" | nanos C2HC-type zinc finger 2 [Source: HGNC Symbol; Acc: HGNC:23292] |
| "ENSG00000162496" | "DHRS3" | dehydrogenase/reductase 3 [Source: HGNC Symbol; Acc: HGNC:17693] |
| "ENSG00000118729" | "CASQ2" | calsequestrin 2 [Source: HGNC Symbol; Acc: HGNC:1513] |
| "ENSG00000213981" | NA | novel transcript antisense to MYO3B |
| "ENSG00000234350" | NA | novel transcript (FLJ13453) |
| "ENSG00000237250" | "LOC100130331" | POTE ankyrin domain family member F pseudogene [Source: NCBI gene; Acc: 100130331] |
| "ENSG00000273064" | NA | novel transcript |
| "ENSG00000058335" | "RASGRF1" | Ras protein specific guanine nucleotide releasing factor 1 [Source: HGNC Symbol; Acc: HGNC:9875] |
| "ENSG00000179564" | "LSMEM2" | leucine rich single-pass membrane protein 2 [Source: HGNC Symbol; Acc: HGNC:26781] |
| "ENSG00000272866" | NA | novel transcript |
| "ENSG00000174611" | "KY" | kyphoscoliosis peptidase [Source: HGNC Symbol; Acc: HGNC:26576] |
| "ENSG00000132692" | "BCAN" | brevican [Source: HGNC Symbol; Acc: HGNC:23059] |
| "ENSG00000100060" | "MENG" | MFNG O-fucosylpeptide 3-beta-N-acetylglucosaminyltransferase [Source: HGNC Symbol; Acc: HGNC:7038] |
| "ENSG00000275812" | NA | novel transcript antisense to SRMS |
| "ENSG00000101203" | "COL20A1" | collagen type XX alpha 1 chain [Source: HGNC Symbol; Acc: HGNC:14670] |
| "ENSG00000143858" | "SYT2" | synaptotagmin 2 [Source: HGNC Symbol; Acc: HGNC:11510] |
| "ENSG00000129757" | "CDKN1C" | cyclin dependent kinase inhibitor 1C [Source: HGNC Symbol; Acc: HGNC:1786] |
| "ENSG00000197921" | "HES5" | hes family bHLH transcription factor 5 [Source: HGNC Symbol; Acc: HGNC:19764] |
| "ENSG00000154080" | "CHST9" | carbohydrate sulfotransferase 9 [Source: HGNC Symbol; Acc: HGNC:19898] |
| "ENSG00000170989" | "S1PR1" | sphingosine-1-phosphate receptor 1 [Source: HGNC Symbol; Acc: HGNC:3165] |
| "ENSG00000165805" | "C12orf50" | chromosome 12 open reading frame 50 [Source: HGNC Symbol; Acc: HGNC:26665] |
| "ENSG00000237941" | "KCNQ1DN" | KCNQ1 downstream neighbor [Source: HGNC Symbol; Acc: HGNC:13335] |
| "ENSG00000226476" | "LINC01748" | long intergenic non-protein coding RNA 1748 [Source: HGNC Symbol; Acc: HGNC:52535] |
| "ENSG00000018625" | "ATP1A2" | ATPase Na+/K+ transporting subunit alpha 2 [Source: HGNC Symbol; Acc: HGNC:800] |
| "ENSG00000198732" | "SMOC1" | SPARC related modular calcium binding 1 [Source: HGNC Symbol; Acc: HGNC:20318] |
| "ENSG00000148734" | "NPFFR1" | neuropeptide FF receptor 1 [Source: HGNC Symbol; Acc: HGNC:17425] |
| "ENSG00000173673" | "HES3" | hes family bHLH transcription factor 3 [Source: HGNC Symbol; Acc: HGNC:26226] |
| "ENSG00000231827" | "LOC343052" | immunoglobulin superfamily DCC subclass member 3 pseudogene [Source: NCBI gene; Acc: 343052] |
| "ENSG00000142494" | "SLC47A1" | solute carrier family 47 member 1 [Source: HGNC Symbol; Acc: HGNC:255 88] |
| "ENSG00000112238" | "PRDM13" | PR/SET domain 13 [Source: HGNC Symbol; Acc: HGNC: 13998] |
| "ENSG00000184221" | "OLIG1" | oligodendrocyte transcription factor 1 [Source: HGNC Symbol; Acc: HGNC: 16983] |
| "ENSG00000177468" | "OLIG3" | oligodendrocyte transcription factor 3 [Source: HGNC Symbol; Acc: HGNC: 18003] |

*Ensembl Gene ID identifier for a gene as per the Ensembl (European Bioinformatics Institute and the Wellcome Trust Sanger Institute) database.

TABLE 3

Effect of Exosomes on Modulation of Extracellular Matrix and Adhesion Proteins.

| ID | Name | #Gene | FDR |
|---|---|---|---|
| hsa04510 | Focal adhesion | 51 | 1.81E−04 |
| hsa04512 | ECM-receptor interaction | 27 | 1.81E−04 |
| hsa04115 | p53 signaling pathway | 24 | 1.81E−04 |
| hsa05200 | Pathways in cancer | 83 | 1.81E−04 |
| hsa04110 | Cell cycle | 35 | 1.97E−04 |
| hsa05222 | Small cell lung cancer | 25 | 2.41E−03 |
| hsa05224 | Breast cancer | 36 | 2.67E−03 |
| hsa05100 | Bacterial invasion of epithelial cells | 23 | 2.82E−03 |
| hsa05412 | Arrhythmogenic right ventricular cardiomyopathy (ARVC) | 22 | 3.12E−03 |
| hsa04151 | PI3K-Akt signaling pathway | 66 | 8.89E−03 |
| hsa05205 | Proteoglycans in cancer | 44 | 8.89E−03 |
| hsa04141 | Protein processing in endoplasmic reticulum | 37 | 1.12E−02 |
| hsa05215 | Prostate cancer | 23 | 1.47E−02 |
| hsa04933 | AGE-RAGE signaling pathway in diabetic complications | 25 | 1.53E−02 |
| hsa04520 | Adherens junction | 20 | 1.53E−02 |
| hsa04390 | Hippo signaling pathway | 34 | 1.68E−02 |
| hsa05161 | Hepatitis B | 32 | 2.52E−02 |
| hsa01521 | EGFR tyrosine kinase inhibitor resistance | 20 | 4.24E−02 |
| hsa04210 | Apoptosis | 30 | 4.51E−02 |
| hsa03460 | Fanconi anemia pathway | 15 | 4.55E−02 |
| hsa04142 | Lysosome | 27 | 4.55E−02 |

Conclusion: Exosomes isolated from MSC-NTF cells carry a unique protein cargo profile and have unique beneficial biological attributes. This tool can now be harnessed in a variety of applications, such as modulating gene expression levels and biological pathways in target cells of interest. Such cellular effects may result in beneficial therapeutic effects in human patients.

While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the disclosure.

What is claimed is:

1. A pharmaceutical composition comprising an isolated exosome population derived from mesenchymal stem cells secreting-neurotrophic factors (MSC-NTF cells), said isolated exosomes comprising an increased quantity of at least one cargo protein, wherein said at least one cargo protein comprises a neurotrophic factor (NTF), compared with the quantity of said at least one cargo protein in an isolated exosome population derived from control non-differentiated MSCs, wherein said NTF comprises a leukemia inhibitory factor (LIF) protein, a vascular endothelial growth factor A (VEGFA) protein, or a growth differentiation factor 15 (GDF15) protein, or any combination thereof,
wherein said MSC-NTF cells are cultured in a three-dimensional (3D) bioreactor in no shear stress, and propagated in Dulbecco's Modified Eagle's Medium (DMEM) comprising platelet lysate,
wherein said exosomes are purified by removing the culture media from the three-dimensional (3D) bioreactor, filtered using a 1.2 µM filter and Tangential Flow Filtration (TFF), and further filtered through a 0.22 µM filter.

2. The pharmaceutical composition comprising an isolated exosome population of claim 1, wherein said at least one cargo protein comprises an NTF and at least one additional protein.

3. The pharmaceutical composition comprising an isolated exosome population of claim 2, wherein said additional protein comprises a chemokine (C-X-C Motif) Ligand 1 (CXCL1) protein or an interleukin 13 (IL13) protein, or a combination thereof.

4. The pharmaceutical composition comprising an isolated exosome population of claim 3, wherein the quantity of LIF protein is increased at least 50-fold, or the quantity of CXCL1 protein is increased at least 30-fold, or the quantity of IL13 protein is increased at least 5-fold, or the quantity of VEGFA is increased at least 5-fold, or the quantity of GDF15 is increased at least 2-fold, or any combination thereof, compared with an isolated exosome population derived from control non-differentiated MSCs.

5. The pharmaceutical composition comprising an isolated exosome population of claim 2, wherein the at least one additional protein comprises an Interleukin-36 alpha (IL36A), a Chemokine (C-C motif) ligand 7 (CCL7), a matrix metalloproteinase-10 (MMP10), a Placental growth factor (PlFG), a chemokine (C-X-C motif) ligand 8 (CXCL8), a Lymphotoxin Alpha (LTA), a chemokine (C-X-C motif) ligand 6 (CXCL6), a matrix metalloproteinase-3 (MMP3), a Chitinase 3 Like 1 (CHI3L1), an Interleukin 11 (IL11), a basic fibroblast growth factor (FGF2), a C-X-C motif chemokine 5 (CXCL5), a Growth Arrest Specific 1 (GAS1), a Junction Adhesion Molecule Like (JAML), a Transforming Growth Factor Beta Receptor 3 (TGFBR3), a Matrix Extracellular Phosphoglycoprotein (MEPE), an Interleukin 6 (IL6), a Platelet Derived Growth Factor Subunit A (PDGFA), a C-C Motif Chemokine Ligand 4 (CCL4), a C-C Motif Chemokine Ligand 21 (CCL21), a C-C Motif Chemokine Ligand 2 (CCL2), a Macrophage Migration Inhibitory Factor (MIF), a Plasminogen Activator, an Urokinase (PLAU), an Angiopoietin Like 4 (ANGPTL4), a Cathepsin B (CTSB), a Basigin (BSG), a C-C Motif Chemokine Ligand 5 (CCL5), a Thyroid Peroxidase (TPO), an Interleukin 23 (IL23), an Interleukin 1 Receptor Like 1 (IL1RL1), a Secreted Phosphoprotein 1 (SPP1), a F11 Receptor (F11R), an Inhibin Subunit Beta A (INHBA), a Familial adenomatous polyposis (FAP), a Serine Peptidase Inhibitor, a Kunitz Type 2 (SPINT2), an Interleukin 36 Gamma (IL36G), a TNF Receptor Superfamily Member 10b (TNFRSF10B) or a TNF Superfamily Member 14 (TNFSF14) protein, or any combination thereof.

6. The pharmaceutical composition comprising an isolated exosome population of claim 1, wherein the isolated exosome population further comprises one or more markers selected from the group consisting of cluster of differentiation (CD) 9, CD29, CD63, CD81, CD44, CD49, CD73, CD90, CD105, CD61, CD271, Programmed Cell Death 6 Interacting Protein (PDCD6IP or ALIX), tumor susceptibility gene (TSG) 101, and any combination thereof;
or is devoid of one or more markers selected from the group consisting of CD3, CD5, CD14, CD19, CD20, CD34, CD45, CD11B, calnexin, human leukocyte antigen-antigen D related (HLA-DR), and any combination thereof; or
any combination thereof.

7. The pharmaceutical composition comprising an isolated exosome population of claim 1, wherein the MSCs are selected from the group consisting of bone marrow MSCs, adipocyte MSCs, dental pulp MSCs, placenta MSCs, synovial membrane MSCs, peripheral blood MSCs, oral mucosa MSCs, periodontal ligament MSCs, endometrium MSCs, umbilical cord MSCs, and umbilical cord blood MSCs.

8. The pharmaceutical composition comprising an isolated exosome population of claim 1, wherein the isolated exosome population further comprises one or more neurotrophic factors (NTF) selected from the group consisting of a hepatocyte growth factor (HGF), a granulocyte stimulating factor (G-CSF), a brain-derived neurotrophic factor (BDNF), a tumor necrosis factor-inducible gene 6 protein (TSG-6), a bone morphogenetic protein 2 (BMP2), and a fibroblast growth factor 2 (FGF2), and any combination thereof.

9. The pharmaceutical composition comprising an isolated exosome population of claim 1, wherein the isolated exosome population further comprises one or more miRNA molecules selected from the group consisting of miRNA (miR)-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, and miR-4324, and any combination thereof; or wherein the isolated exosome population is devoid of one or more miRNA molecule selected from the group consisting of miR-503, miR-3659, miR-3529-3p, miR-320b, miR-1275, miR-3132, miR-320a, miR-495, miR-181b-5p, miR-222-3p, miR-424-5p, miR-4284, miR-574-5p, miR-143-3p, miR-106a-5p, miR-455-3p, miR-20a-5p, miR-145-5p, miR-324-3p, miR-130b-3p, miR-1305, and miR-140-3p, and any combination thereof; or any combination thereof.

* * * * *